US 10,850,077 B2

United States Patent
Terliuc et al.

(10) Patent No.: US 10,850,077 B2
(45) Date of Patent: Dec. 1, 2020

(54) CONTROLLED FURLING BALLOON ASSEMBLY

(71) Applicant: SMART MEDICAL SYSTEMS LTD., Ra'Anana (IL)

(72) Inventors: Gad Terliuc, Ra'Anana (IL); Gilad Luria, Givataim (IL)

(73) Assignee: SMART MEDICAL SYSTEMS LTD., Raanana (IL)

( * ) Notice: Subject to any disclaimer, the term of this patent is extended or adjusted under 35 U.S.C. 154(b) by 325 days.

(21) Appl. No.: 15/328,906

(22) PCT Filed: Jul. 23, 2015

(86) PCT No.: PCT/IL2015/050765
§ 371 (c)(1),
(2) Date: Jan. 25, 2017

(87) PCT Pub. No.: WO2016/016883
PCT Pub. Date: Feb. 4, 2016

(65) Prior Publication Data
US 2017/0216568 A1 Aug. 3, 2017

Related U.S. Application Data

(60) Provisional application No. 61/999,457, filed on Jul. 28, 2014.

(51) Int. Cl.
*A61M 25/10* (2013.01)
*A61B 1/00* (2006.01)
(Continued)

(52) U.S. Cl.
CPC ... *A61M 25/10184* (2013.11); *A61B 1/00082* (2013.01); *A61B 1/00135* (2013.01);
(Continued)

(58) Field of Classification Search
CPC ...... A61M 25/1035; A61M 2025/1004; A61M 25/10; A61M 2025/1081;
(Continued)

(56) References Cited

U.S. PATENT DOCUMENTS 4,261,339 A * 4/1981 Hanson ............... A61M 25/0111
600/18
4,531,512 A * 7/1985 Wolvek ................. A61M 25/10
600/18
(Continued)

FOREIGN PATENT DOCUMENTS

EP 0256683 A2 2/1988
JP 2011520515 A 7/2001
(Continued)

OTHER PUBLICATIONS

PCT/IL2015/50765, International Search Report, dated Feb. 4, 2016.
(Continued)

*Primary Examiner* — George J Ulsh
*Assistant Examiner* — Andrew P. Restaino
(74) *Attorney, Agent, or Firm* — Alphapatent Associates, Ltd; Daniel J. Swirsky

(57) ABSTRACT

A user-operable controlled furling balloon assembly including a furlable balloon sheath, an elongate furling driving element which is retractable and rotatable about an elongate axis thereof relative to a base element for furling the furlable balloon sheath about the elongate axis, the furlable balloon sheath surrounding the elongate furling driving element and coupled at a first end thereof to the elongate furling driving element and at a second end thereof to the base element and a furling/retraction controlling assembly coupled to the elongate furling driving element and to the base element for limiting an extent of retraction of the elongate furling
(Continued)

driving element to be a function of an extent of furling of the balloon sheath, thereby limiting a maximum outer diameter of the balloon sheath when furled and preventing stacking of the balloon sheath.

3 Claims, 48 Drawing Sheets

(51) Int. Cl.
*A61B 1/32* (2006.01)
*A61M 29/02* (2006.01)

(52) U.S. Cl.
CPC ............... *A61B 1/32* (2013.01); *A61M 29/02* (2013.01); *A61M 2025/1004* (2013.01); *A61M 2025/1081* (2013.01); *A61M 2025/1084* (2013.01)

(58) Field of Classification Search
CPC .... A61M 2025/1084; A61M 25/10184; A61M 29/02; A61M 2525/1002; A61M 2525/1006; A61M 2025/1068; A61M 25/1038; A61B 1/00082; A61B 1/00135; A61B 1/32; A61B 25/1038
USPC .......................................................... 606/192
See application file for complete search history.

(56) References Cited

U.S. PATENT DOCUMENTS

| | | | |
|---|---|---|---|
| 4,608,984 A * | 9/1986 | Fogarty | A61M 25/104 |
| | | | 604/913 |
| 4,681,092 A | 7/1987 | Cho et al. | |
| 5,181,911 A | 1/1993 | Shturman | |
| 5,662,703 A | 9/1997 | Yurek et al. | |
| 6,013,092 A | 1/2000 | Dehdashtian et al. | |
| 7,963,911 B2 | 6/2011 | Turliuc | |
| 8,192,426 B2 | 6/2012 | Stern et al. | |
| 8,257,074 B1 | 9/2012 | Stupecky | |
| 8,727,970 B2 | 5/2014 | Terliuc et al. | |
| 9,119,532 B2 | 9/2015 | Terliuc et al. | |
| 9,427,142 B2 | 8/2016 | Terliuc et al. | |
| 9,596,979 B2 | 3/2017 | Terliuc et al. | |
| 9,661,994 B2 | 5/2017 | Terliuc et al. | |
| 10,052,014 B2 | 8/2018 | Terliuc et al. | |
| 2001/0016725 A1 * | 8/2001 | Valley | A61B 17/00234 |
| | | | 604/509 |
| 2009/0024087 A1 * | 1/2009 | Kennedy, II | A61M 25/10 |
| | | | 604/99.01 |
| 2009/0187069 A1 | 7/2009 | Terliuc et al. | |
| 2009/0287058 A1 | 11/2009 | Terliuc | |
| 2009/0287203 A1 | 11/2009 | Mazzone et al. | |
| 2010/0076402 A1 | 3/2010 | Mazzone et al. | |
| 2010/0217185 A1 | 8/2010 | Terliuc et al. | |
| 2014/0088362 A1 | 3/2014 | Terliuc et al. | |
| 2015/0273191 A1 * | 10/2015 | Terliuc | A61B 1/00082 |
| | | | 604/99.01 |
| 2015/0335229 A1 | 11/2015 | Terliuc | |
| 2016/0022120 A1 | 1/2016 | Terliuc et al. | |
| 2016/0095508 A1 | 4/2016 | Terliuc et al. | |
| 2017/0027415 A1 | 2/2017 | Terliuc et al. | |
| 2017/0027433 A1 | 2/2017 | Terliuc | |
| 2017/0100017 A1 | 4/2017 | Terliuc et al. | |
| 2017/0203080 A1 | 7/2017 | Terliuc et al. | |
| 2017/0360282 A1 | 12/2017 | Terliuc et al. | |
| 2018/0333043 A1 | 11/2018 | Terliuc et al. | |

FOREIGN PATENT DOCUMENTS

| | | |
|---|---|---|
| JP | 2004223080 A | 8/2004 |
| JP | 2011234746 | 11/2011 |
| JP | 2012527941 A | 11/2012 |
| WO | 2005/074377 A2 | 8/2005 |
| WO | 2007/017854 A2 | 2/2007 |
| WO | 2007/135665 A2 | 11/2007 |
| WO | 2008/004228 A2 | 1/2008 |
| WO | 2008/142685 A2 | 11/2008 |
| WO | 2009/122395 A2 | 10/2009 |
| WO | 2010/046891 A2 | 4/2010 |
| WO | 2010/137025 A2 | 12/2010 |
| WO | 2011/111040 A2 | 9/2011 |
| WO | 2012/120492 A1 | 9/2012 |
| WO | 2014/068569 A2 | 5/2014 |

OTHER PUBLICATIONS

PCT/IL2015/50765, Written Opinion, dated Feb. 4, 2016.
PCT/IL2015/50765, International Preliminary Report on Patentability, dated Jan. 31, 2017.

* cited by examiner

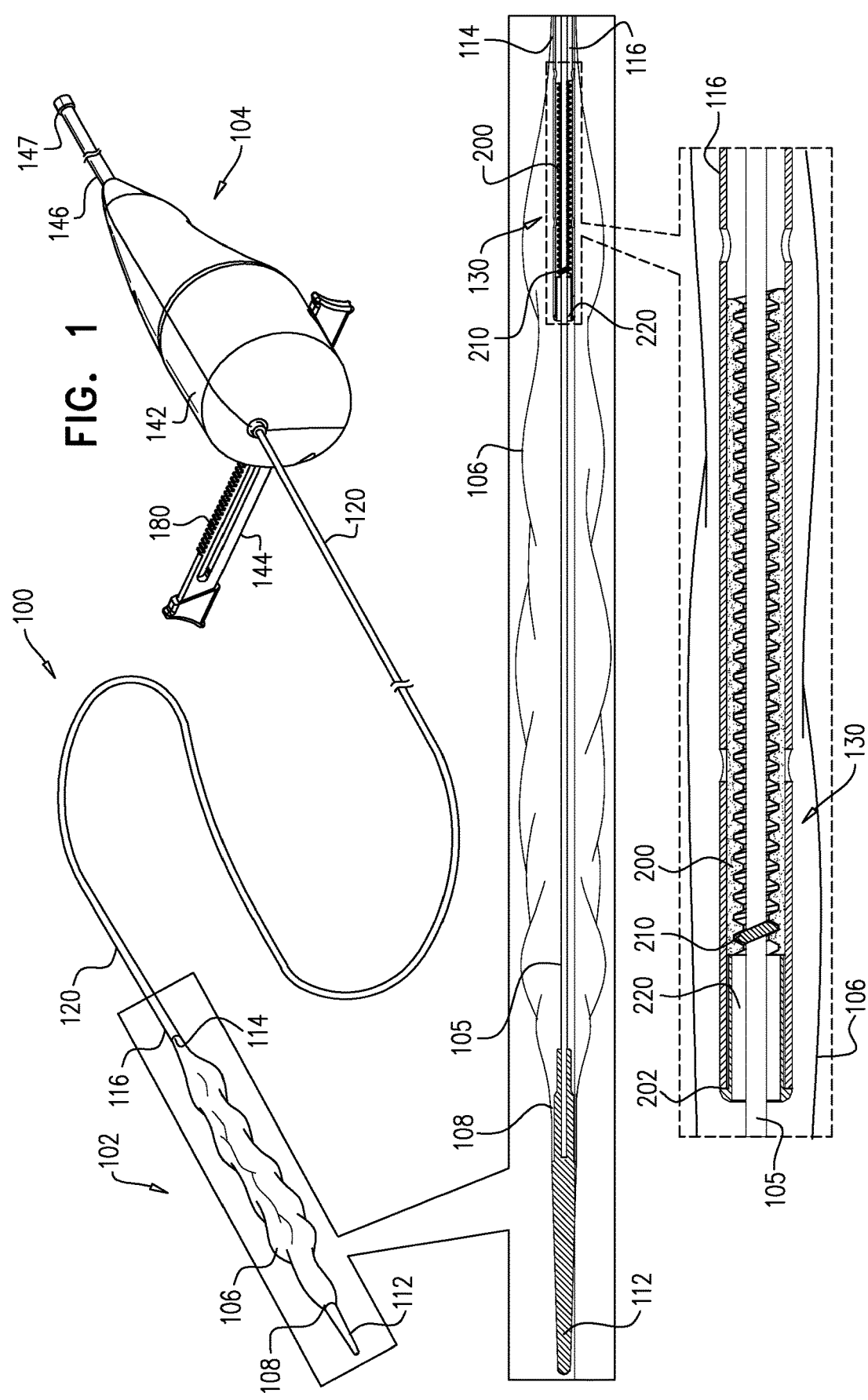

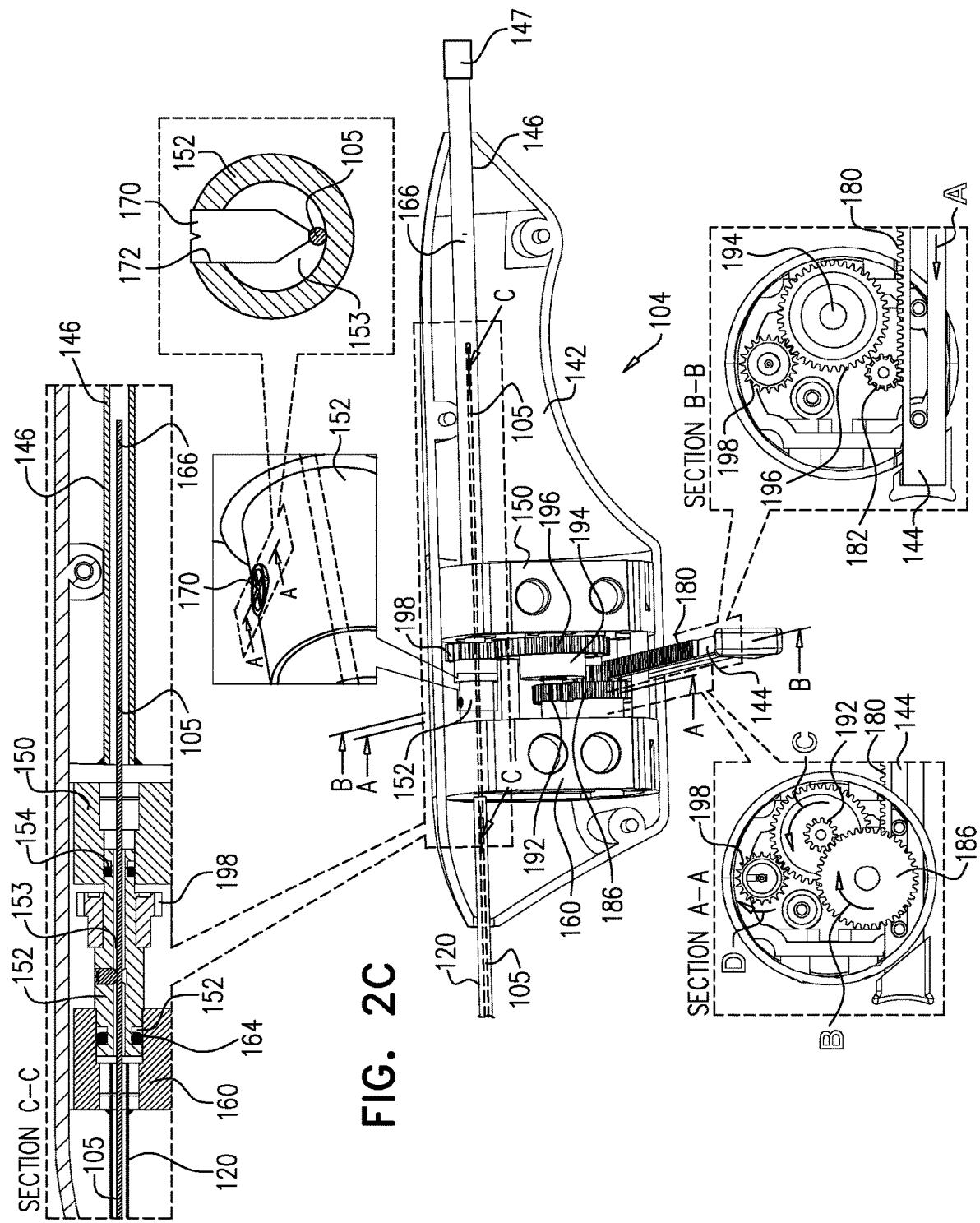

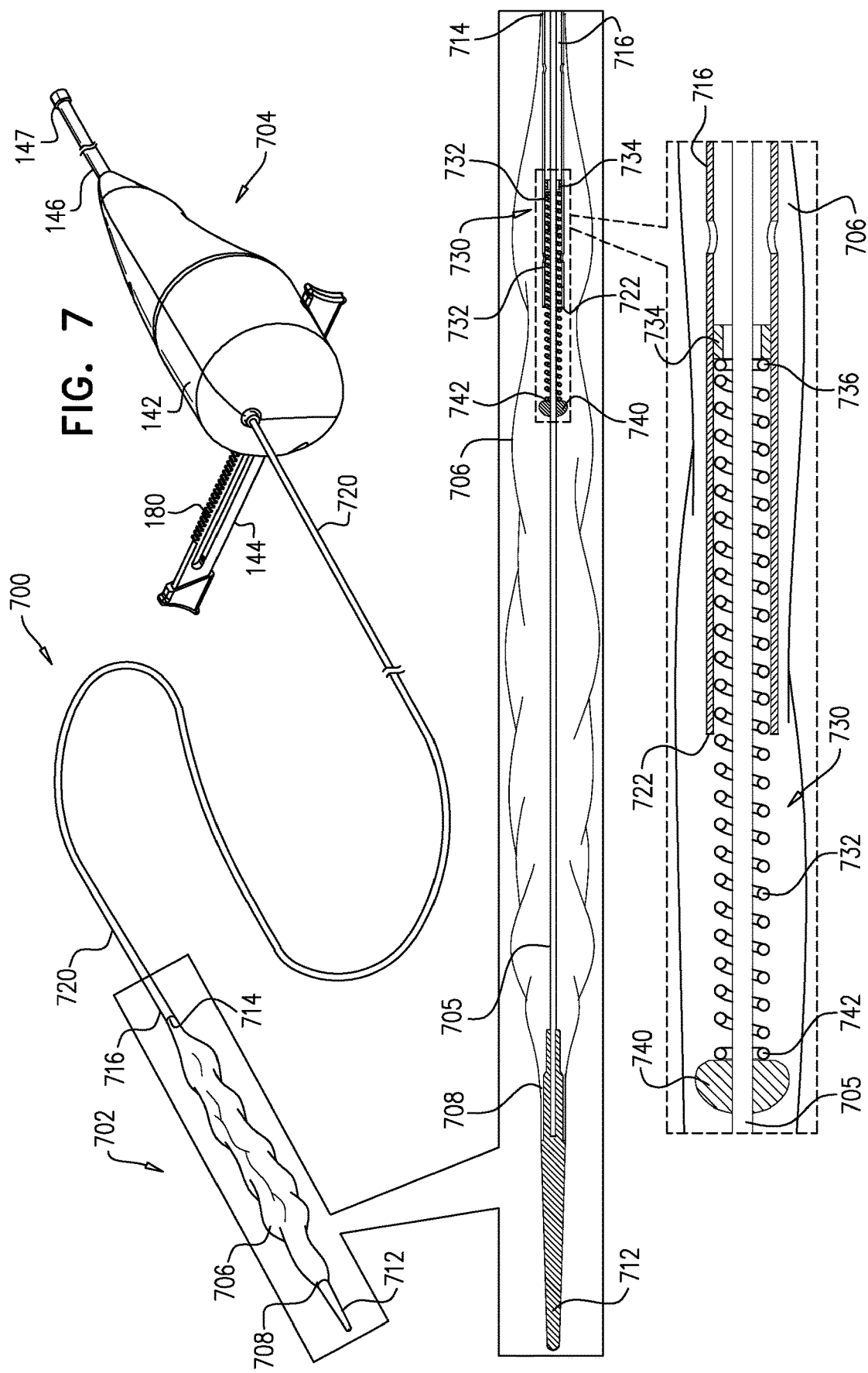

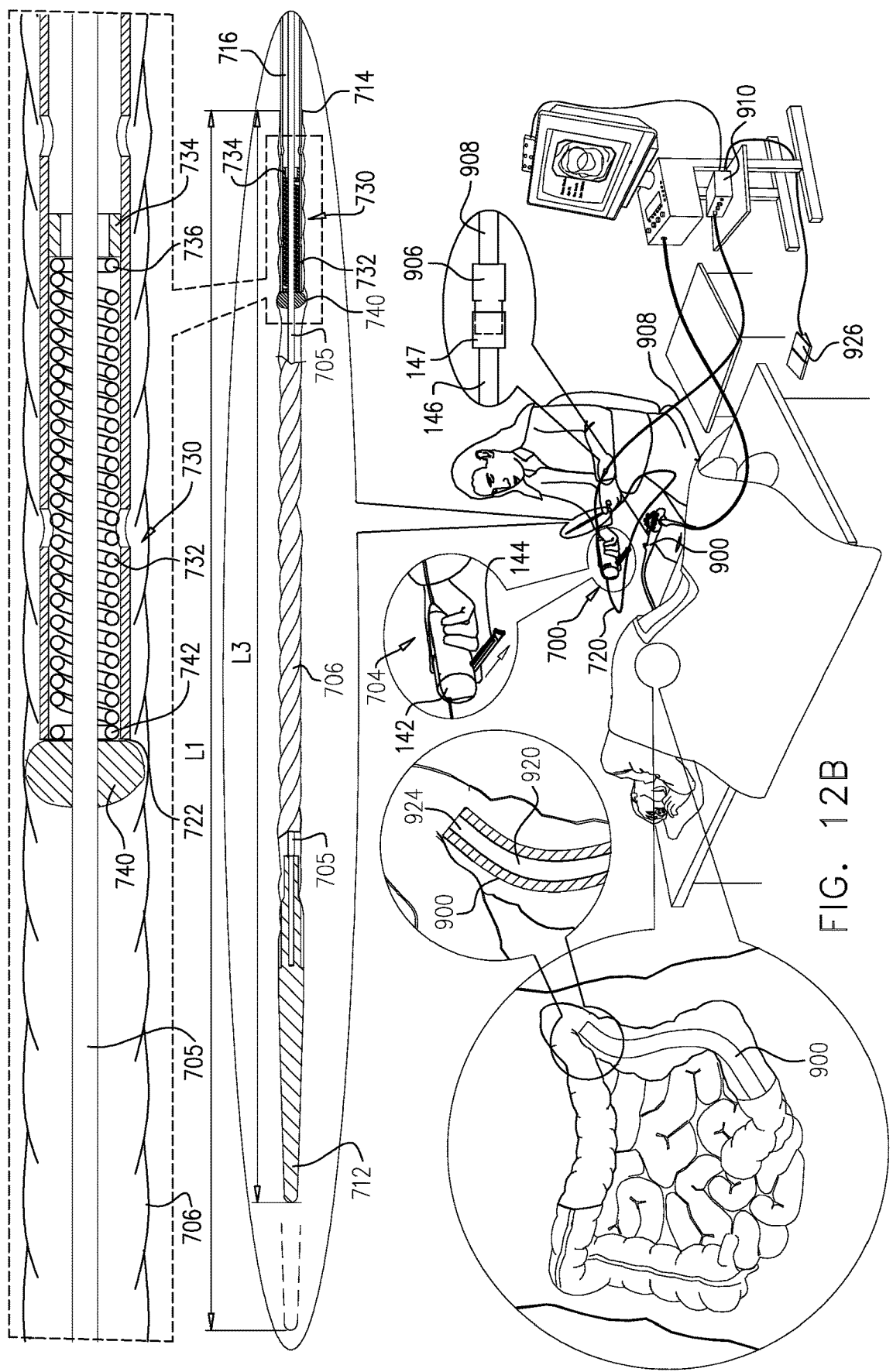

CONTROLLED FURLING BALLOON ASSEMBLY

CROSS-REFERENCE TO RELATED APPLICATIONS

This application is a U.S. National Phase Application under 35 U.S.C. 371 of International Application No. PCT/IL2015/050765, which has an international filing date of Jul. 23, 2015, and which claims the priority benefit of U.S. Provisional Patent Application Ser. No. 61/999,457, filed Jul. 28, 2014 and entitled "Rotatable Balloon With Longitudinal Movement", the disclosure of which is hereby incorporated by reference in its entirety.

Reference is also made to applicant's Published PCT Patent Applications WO2005/074377; WO2007/017854; WO2007/135665; WO2008/004228; WO2008/142685; WO2009/122395; WO2010/046891; WO2010/137025; WO2011/111040; WO/2012/120492; WO/2014/068569 and WO2014/188402, the disclosures of which are hereby incorporated by reference.

FIELD OF THE INVENTION

The present invention relates to endoscope systems generally.

BACKGROUND OF THE INVENTION

Various types of endoscope systems and anchoring assemblies for endoscopes are known.

SUMMARY OF THE INVENTION

The present invention seeks to provide improved anchoring assemblies for operation with elongate articles such as endoscopes.

There is thus provided in accordance with a preferred embodiment of the present invention a user-operable controlled furling balloon assembly including a furlable balloon sheath, an elongate furling driving element which is retractable and rotatable about an elongate axis thereof relative to a base element for furling the furlable balloon sheath about the elongate axis, the furlable balloon sheath surrounding the elongate furling driving element and coupled at a first end thereof to the elongate furling driving element and at a second end thereof to the base element and a furling/retraction controlling assembly coupled to the elongate furling driving element and to the base element for limiting an extent of retraction of the elongate furling driving element to be a function of an extent of furling of the balloon sheath, thereby limiting a maximum outer diameter of the balloon sheath when furled and preventing stacking of the balloon sheath.

Preferably, the furling/retraction controlling assembly includes a cam element fixed to the elongate furling driving element and a cam path defining element which establishes a predetermined relationship between rotation of the elongate furling driving element and the retraction of the elongate furling driving element. Additionally, the cam path defining element defines an elongate spiral cam path. Additionally or alternatively, the predetermined relationship is effective to prevent at least one of premature retraction of the elongate furling driving element, which would lead to bunching of the balloon sheath, excessive retraction of the elongate furling driving element, which would lead to bunching of the balloon sheath and insufficient retraction of the elongate furling driving element, which would lead to bowing of the elongate furling driving element.

In accordance with a preferred embodiment of the present invention the furling/retraction controlling assembly includes an elongate spring resiliently urging the elongate furling driving element against retraction relative to the base element and thereby establishing a relationship between rotation of the elongate furling driving element and the retraction of the elongate furling driving element. Additionally, the relationship is effective to prevent at least one of premature retraction of the elongate furling driving element, which would lead to bunching of the balloon sheath, excessive retraction of the elongate furling driving element, which would lead to bunching of the balloon sheath and insufficient retraction of the elongate furling driving element, which would lead to bowing of the elongate furling driving element.

Preferably, the base element is a catheter tube.

In accordance with a preferred embodiment of the present invention the user-operable controlled furling balloon assembly also includes a manually-controllable furling control assembly including a housing and a manually-manipulatable linear driving element, manually linearly positionable relative to the housing for controlling the extent of furling of the furlable balloon sheath. Additionally, linear displacement of the manually-manipulatable linear driving element in a first linear direction provides furling of the furlable balloon sheath and linear displacement of the manually-manipulatable linear driving element in a second linear direction, opposite the first linear direction, provides unfurling of the furlable balloon sheath.

Preferably, the manually-controllable furling control assembly also includes a first rotary gear having a first and a second circular gear train, a second rotary gear having a first and a second circular gear train and a third rotary gear which is fixed to the elongate furling driving element for rotation together therewith, the manually-manipulatable linear driving element includes a linear gear train engaging the first circular gear train of the first rotary gear, the second circular gear train of the first rotary gear operatively engages the first circular gear train of the second rotary gear and the second circular gear train of the second rotary gear operatively engages the third rotary gear.

In accordance with a preferred embodiment of the present invention the user-operable controlled furling balloon assembly also includes a tip element coupling the balloon sheath to the elongate furling driving element and a longitudinal extent along the elongate furling driving element from a rearward end of the balloon sheath to a forward end of the tip element is a first length when the balloon sheath is unfurled, a second length, less than the first length, when the balloon sheath is partially furled and a third length, less than the first length and less than the second length, when the balloon sheath is fully furled.

There is also provided in accordance with another preferred embodiment of the present invention a method for controlled furling of a balloon including providing a balloon including an elongate furling driving element which is retractable and rotatable about an elongate axis thereof relative to a base element for furling the balloon about the elongate axis and a furlable balloon sheath surrounding the elongate furling driving element and coupled at a first end thereof to the elongate furling driving element and at a second end thereof to the base element and furling the balloon and retracting the elongate furling driving element relative to the base element in a mutually controlled manner whereby an extent of retraction of the elongate furling element is a predetermined function of an extent of furling of the balloon sheath, thereby limiting a maximum outer diameter of the balloon sheath and preventing stacking of the balloon sheath.

Preferably, the furling the balloon and retracting the elongate furling driving element relative to the base element in a mutually controlled manner includes establishing a predetermined relationship between rotation of the elongate furling driving element and the retraction of the elongate furling driving element. Additionally, the predetermined relationship is effective to prevent at least one of premature retraction of the elongate furling driving element, which would lead to bunching of the balloon sheath, excessive retraction of the elongate furling driving element, which would lead to bunching of the balloon sheath and insufficient retraction of the elongate furling driving element, which would lead to bowing of the elongate furling driving element.

In accordance with a preferred embodiment of the present invention the furling the balloon and retracting the elongate furling driving element relative to the base element in a mutually controlled manner includes resiliently urging the elongate furling driving element against retraction relative to the base element and thereby establishing a relationship between rotation of the elongate furling driving element and the retraction of the elongate furling driving element. Additionally, the relationship is effective to prevent at least one of premature retraction of the elongate furling driving element, which would lead to bunching of the balloon sheath, excessive retraction of the elongate furling driving element, which would lead to bunching of the balloon sheath and insufficient retraction of the elongate furling driving element, which would lead to bowing of the elongate furling driving element.

Preferably, the base element is a catheter tube.

In accordance with a preferred embodiment of the present invention the method for controlled furling of a balloon also includes controlling the extent of furling of the furlable balloon sheath by manually manipulating a linear driving element. Additionally, the manually manipulating a linear driving element includes linearly displacing the linear driving element in a first linear direction to provide furling of the furlable balloon sheath and linearly displacing the linear driving element in a second linear direction, opposite the first linear direction to provide unfurling of the furlable balloon sheath.

BRIEF DESCRIPTION OF THE DRAWINGS

The present invention will be understood and appreciated more fully from the following detailed description, taken in conjunction with the drawings in which:

FIG. 1 is a simplified illustration of a user-operable controlled furling balloon assembly constructed and operative in accordance with a preferred embodiment of the present invention including a configured furl balloon assembly and a furling control assembly;

FIG. 2C is a simplified partially cut away illustration of the furling control assembly of FIGS. 1 and 2B;

FIGS. 6A, 6B, 6C, 6D, 6E, 6F, 6G, 6H, 6I, 6J, 6K, 6L, 6M, 6N, 6O and 6P are simplified pictorial illustrations of operation of an endoscope system including the user-operable controlled furling balloon assembly of FIGS. 1-5C in accordance with a preferred embodiment of the present invention;

FIG. 7 is a simplified illustration of a user-operable controlled furling balloon assembly constructed and operative in accordance with another preferred embodiment of the present invention including a configured furl balloon assembly and a furling control assembly;

FIGS. 12A, 12B, 12C, 12D, 12E, 12F, 12G, 12H, 12I, 12J, 12K, 12L, 12M, 12N, 12O and 12P are simplified pictorial illustrations of operation of an endoscope system including the user-operable controlled furling balloon assembly of FIGS. 7-11C in accordance with a preferred embodiment of the present invention.

DETAILED DESCRIPTION OF PREFERRED EMBODIMENTS

The terms "endoscope" and "endoscopy" are used throughout in a manner somewhat broader than their customary meaning and refer to apparatus and methods which operate within body cavities, passageways and the like, such as, for example, the small intestine and the large intestine. Although these terms normally refer to visual inspection, as used herein they are not limited to applications which employ visual inspection and refer as well to apparatus, systems and methods which need not necessarily involve visual inspection.

The term "forward" refers to the remote end of an endoscope, accessory or tool furthest from the operator or to a direction facing such remote end.

The term "rearward" refers to the end portion of an endoscope, accessory or tool closest to the operator, typically outside an organ or body portion of interest or to a direction facing such end portion.

Figure 2A:
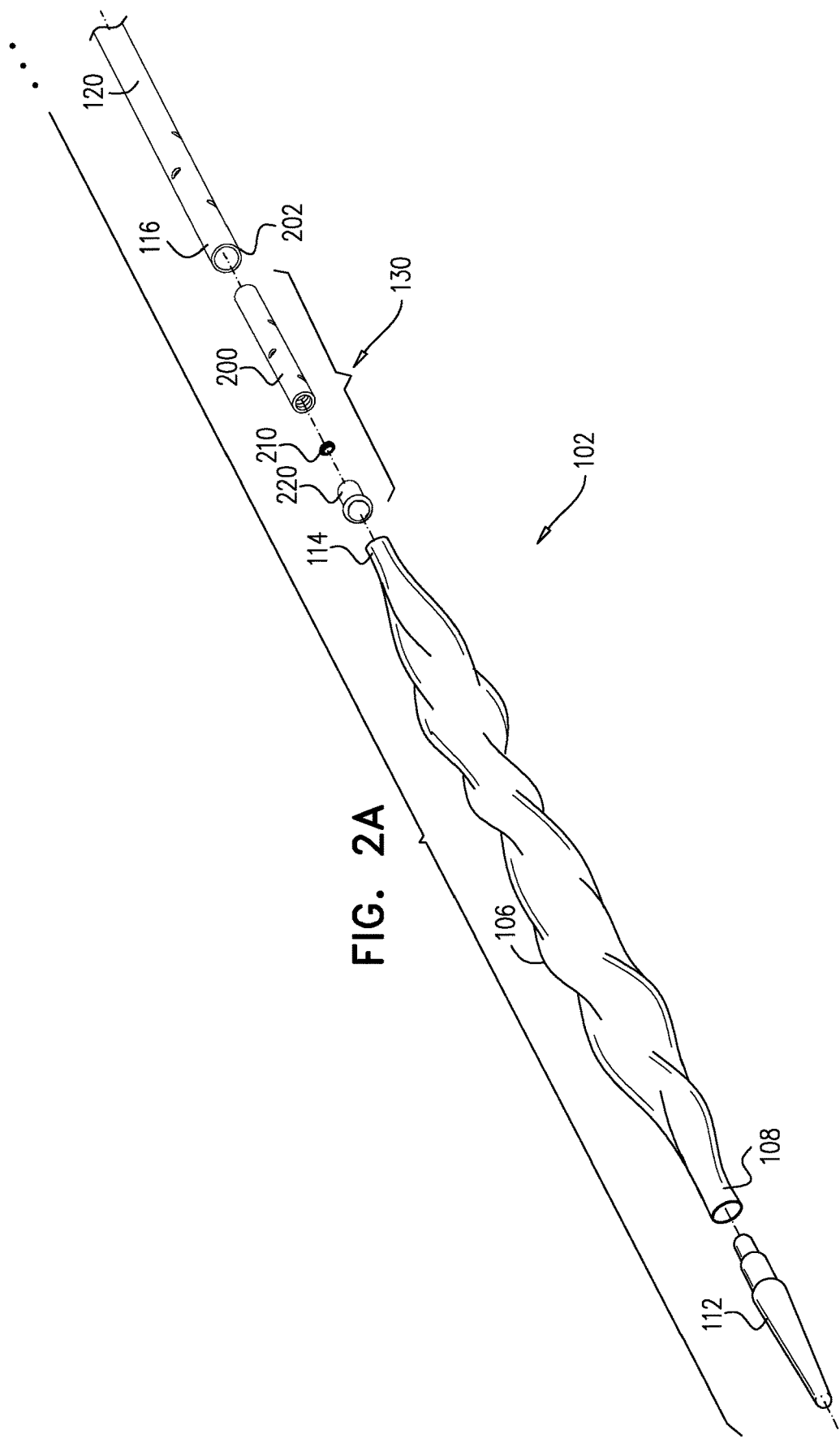
FIG. 2A is a simplified exploded view illustration of the configured furl balloon assembly of FIG. 1.
Figure 2B:
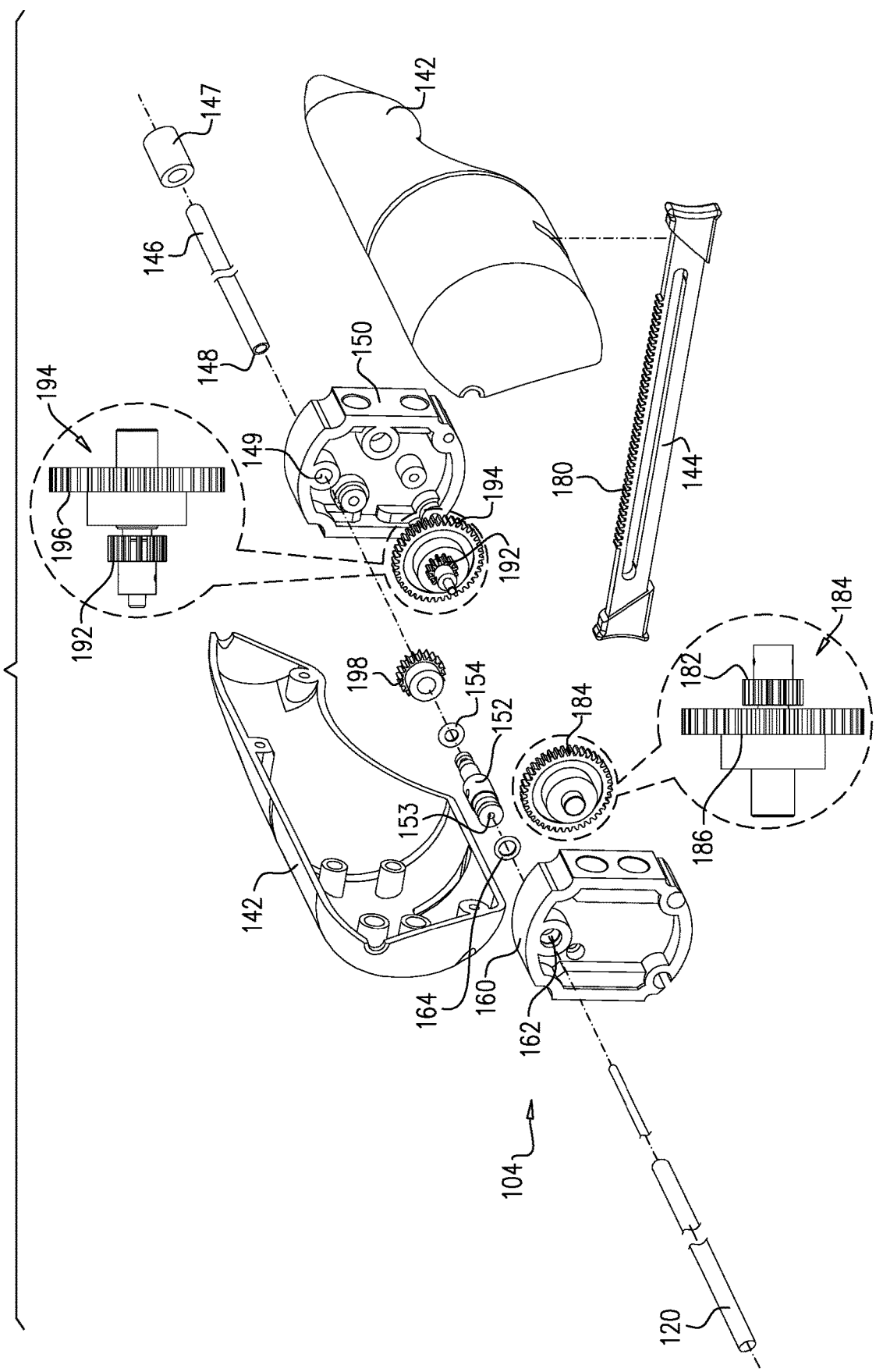
FIG. 2B is a simplified exploded view illustration of the furling control assembly of FIG. 1.

Reference is now made to FIG. 1, which is a simplified partially pictorial, partially sectional, illustration of a user-operable controlled furling balloon assembly 100, associatable with an endoscope in accordance with a preferred embodiment of the present invention, including a configured furl balloon assembly 102 and a manually-controllable furling control assembly 104, to FIG. 2A, which is a simplified exploded view illustration of the configured furl balloon assembly 102 of FIG. 1, to FIG. 2B, which is a simplified exploded view illustration of the furling control assembly 104 of FIG. 1, and to FIG. 2C, which is a simplified partially cut away illustration of the furling control assembly 104 of FIGS. 1 and 2B.

In accordance with a preferred embodiment of the present invention, the user-operable controlled furling balloon assembly 100 includes an elongate furling driving element 105, preferably in the form of a wire, preferably formed of stainless steel, which is retractable and rotatable about an elongate axis thereof.

As seen in FIG. 2A, the configured furl balloon assembly 102 preferably includes a furlable balloon sheath 106, which surrounds a forward portion of the elongate furling driving element 105 (FIG. 1) and is coupled at a forward end 108 thereof via a tip element 112 to the elongate furling driving element 105 (FIG. 1) and at a rearward end 114 thereof to a forward portion 116 of a catheter tube 120.

The configured furl balloon assembly 102 also comprises a furling/retraction controlling assembly 130, which is fixedly coupled to the catheter tube 120, at forward portion 116 thereof, for limiting an extent of retraction of the elongate furling driving element 105 (FIG. 1) to be a function of an extent of furling of the balloon sheath 106, thereby limiting a maximum outer diameter of the balloon sheath 106 when furled and preventing stacking of the balloon sheath 106.

As seen in FIGS. 1, 2B and 2C, manually-controllable furling control assembly 104 preferably comprises a housing 142 and a manually-manipulatable linear driving element 144, which may be manually linearly positioned relative to housing 142 for controlling the extent of furling of furlable balloon sheath 106 (FIGS. 1 and 2A).

Mounted onto housing 142 is an inflation/deflation connection tube 146, having at a rearward end thereof a bayonet connector end piece 147 for removable connection to a balloon inflation/deflation device (not shown), preferably a SPARK 2C, commercially available from Smart Medical Systems Ltd. of Raanana, Israel. A forward end 148 of inflation/deflation connection tube 146 is sealingly coupled to an aperture 149 in a rearward bulkhead element 150.

A nipple element 152 having an axial throughgoing passageway 153 is rotatably mounted onto bulkhead element 150 at aperture 149, preferably via a sealing ring 154. Passageway 153 communicates with the interior of inflation/deflation tube 146.

A forward-facing portion of nipple element 152 is rotatably mounted onto a forward bulkhead element 160 at an aperture 162 thereof, preferably by means of a sealing ring 164. A rearward end of catheter tube 120 is fixedly and sealingly engaged with aperture 162 in forward bulkhead element 160. In this manner the interior of connection tube 146 sealingly communicates with the interior of catheter tube 120.

Elongate furling driving element 105, as noted above, typically a stainless steel wire, typically extends from a rearward end 166 thereof lying within connection tube 146, through aperture 149 in rearward bulkhead element 150 and through passageway 153 in nipple element 152.

Elongate furling driving element 105 is preferably fixed to nipple element 152 by a set screw 170 which sealingly extends through a threaded aperture 172 in nipple element 152 and tightly engages elongate furling driving element 105 against a wall of passageway 153. It is appreciated that nipple 152 and elongate furling driving element 105 thus are restricted to move together rotationally and cannot move longitudinally relative to the furling control assembly 104.

Elongate furling driving element 105 extends forwardly from nipple 152, through aperture 162 in forward bulkhead element 160 and through catheter tube 120 and forwardly therebeyond through balloon sheath 106 to tip element 112.

Operation of the furling control assembly 104 for controlled furling and unfurling of balloon sheath 110 will now be briefly described with particular reference to FIGS. 2B and 2C. Manually-manipulatable linear driving element 144 is shown in a fully-unfurled operative orientation and is seen to include on a top-facing surface thereof a linear gear train 180.

Linear gear train 180 operatively engages a first circular gear train 182 of a rotary gear 184, having a second circular gear train 186. Second circular gear train 186 of rotary gear 184 operatively engages a first circular gear train 192 of a rotary gear 194, having a second circular gear train 196. Second circular gear train 196 operatively engages a rotary gear 198, which surrounds and is fixedly attached to nipple 152 for rotation together therewith.

It is thus appreciated that that linear displacement of manually-manipulatable linear driving element 144 in a linear direction A (FIG. 2C) causes rotation of rotary gear 184 in a rotational direction B and consequent rotation of rotary gear 194 in a rotational direction C, resulting in rotation of nipple 152 in a rotational direction D, thereby providing furling.

Figure 3A:
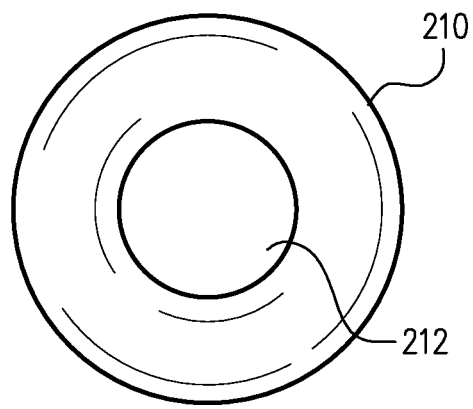
FIGS. 3A, 3B and 3C are simplified illustrations of a cam element useful in the configured furl balloon assembly of FIG. 2A.
Figure 3B:
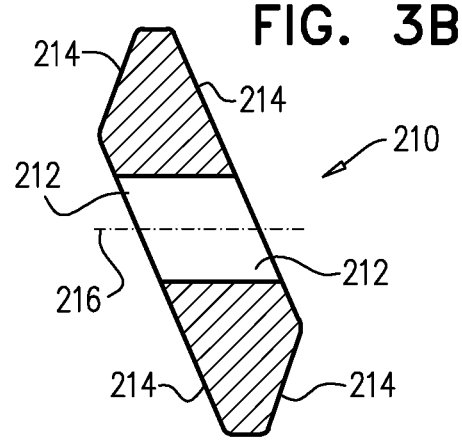
Figure 3C:
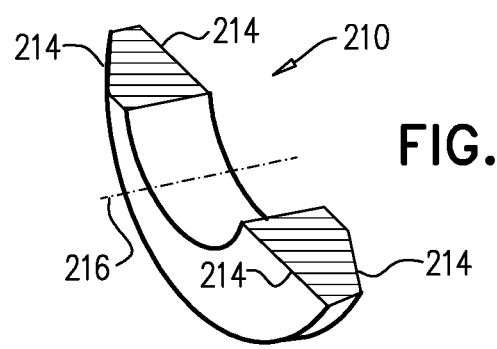
Figure 4A:
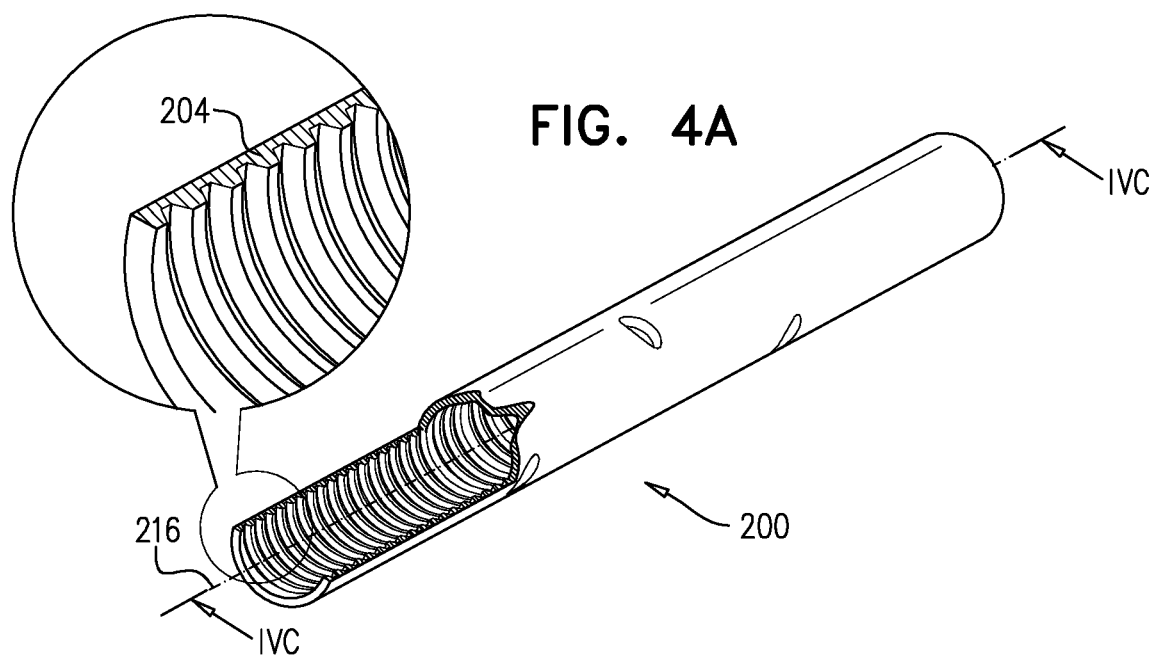
FIGS. 4A, 4B and 4C are simplified illustrations of a cam path defining element useful in the configured furl balloon assembly of FIG. 2A, FIG. 4C being a sectional view taken along lines IVC-IVC of FIG. 4A.
Figure 4B:
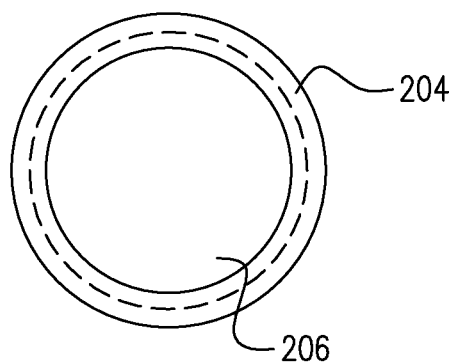
Figure 4C:
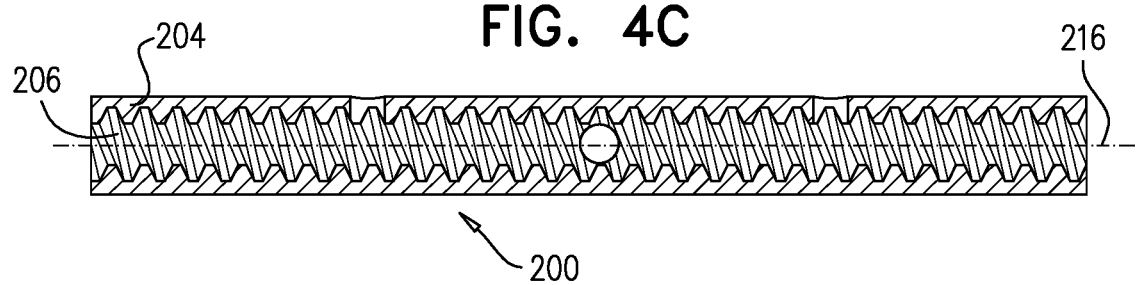
Figure 5A:
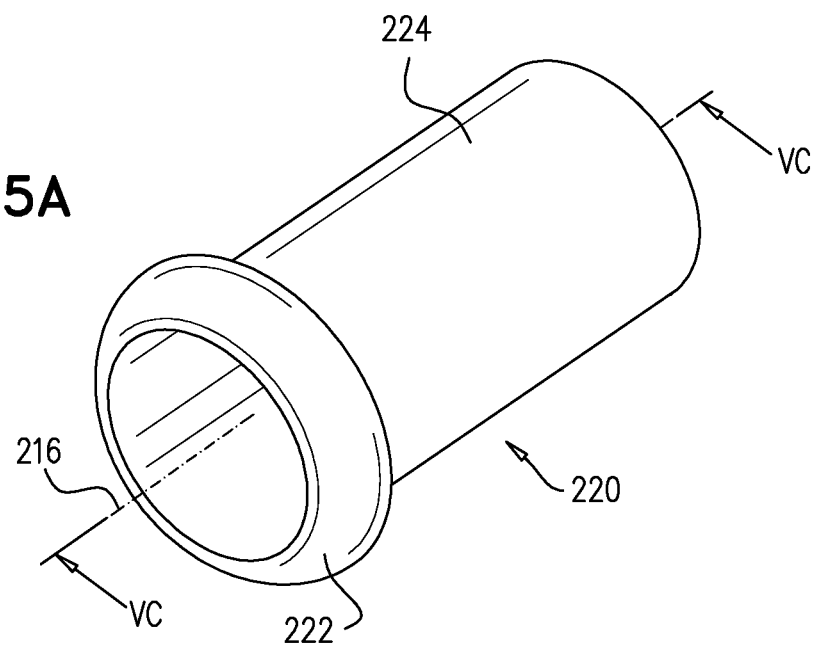
FIGS. 5A, 5B and 5C are simplified illustrations of an engagement element useful in the configured furl balloon assembly of FIG. 2A, FIG. 5C being a partially cut away view taken along lines VC-VC of FIG. 5A.
Figure 5B:
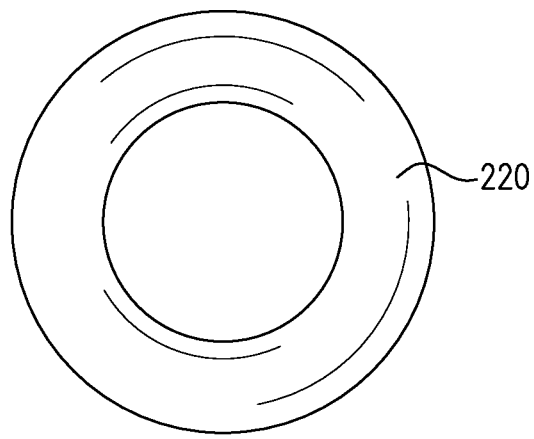
Figure 5C:
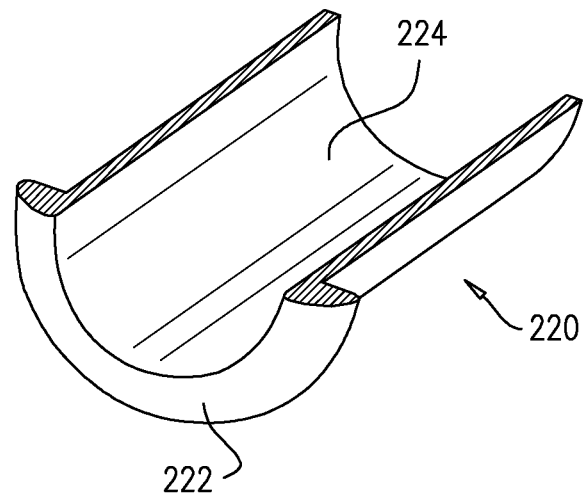

Reference is now made again to FIG. 1, which illustrates the furling/retraction controlling assembly 130 which forms part of the configured furl balloon assembly 102, and also to FIGS. 3A-3C, which are simplified illustrations of a cam element useful in the configured furl balloon assembly 102 of FIG. 2A, to FIGS. 4A-4C, which are simplified illustrations of a cam path defining element useful in the configured furl balloon assembly 102 of FIG. 2A, and to FIGS. 5A-5C, which are simplified illustrations of an engagement element useful in the configured furl balloon assembly 102 of FIG. 2A.

FIGS. 4A, 4B and 4C illustrate a cam path defining element 200, which is fixedly located inside of and near the forward end 202 of forward portion 116 of catheter tube 120. Cam path defining element 200 preferably comprises an elongate spiral cam path 204 surrounding a longitudinal passageway 206 extending therethrough, through which extends elongate furling driving element 105. Cam path defining element 200 is preferably formed of flexible material such as Teflon®. Alternatively, spiral cam path may be formed of a rigid material, such as stainless steel or polycarbonate.

FIGS. 3A, 3B and 3C illustrate a preferred cam element 210 having an aperture 212 and defining cam path engaging surfaces 214. Preferably, elongate furling driving element 105 is threaded through aperture 212 of cam element 210 and fixed thereto for both rotation and longitudinal displacement together therewith generally along a longitudinal axis 216.

FIGS. 5A, 5B and 5C are simplified illustrations of an engagement element 220, which is preferably adhesively retained at the forward end 202 of forward portion 116 of catheter tube 120. Engagement element 220 preferably includes a forward circumferential lip portion 222, which lies forwardly of forward end 202 and is integrally formed with a cylindrical portion 224 which is preferably tightly seated within forward portion 116 of catheter tube 120, forwardly of cam path defining element 200 and in engagement with a forward end thereof.

It is appreciated that the arrangement described above, whereby cam element 210, defining cam path engaging surfaces 214, is fixed to elongate furling driving element 105 for both rotation and longitudinal displacement together therewith generally along longitudinal axis 216 in engagement with elongate spiral cam path 204 of cam path defining element 200, is effective for limiting an extent of retraction of the elongate furling driving element 105 to be a function of an extent of furling of the balloon sheath 106, thereby limiting a maximum outer diameter of the balloon sheath 106 when furled and preventing stacking of the balloon sheath 106.

It is appreciated that the pitch of cam path defining element 200 defines the above function, namely the permitted relationship between the extent of furling of the balloon sheath 106 and the extent of elongate retraction of the elongate furling driving element 105. Establishing the relationship between the extent of furling of the balloon sheath 106 and the extent of elongate retraction of the elongate furling driving element 105 is effective to prevent at least one of the following effects:

premature retraction of the elongate furling driving element 105, which would lead to bunching of the balloon sheath 106;

excessive retraction of the elongate furling driving element 105, which would lead to bunching of the balloon sheath 106;

insufficient retraction of the elongate furling driving element 105, which would lead to bowing of the elongate furling driving element 105 and consequent difficulties in retraction of the configured furl balloon assembly 102 into and passage thereof through the instrument channel of an endoscope.

Reference is now made to FIGS. 6A, 6B, 6C, 6D, 6E, 6F, 6G, 6H, 6I, 6J, 6K, 6L, 6M, 6N, 6O and 6P, which are simplified pictorial illustrations of operation of an endoscope system including the user-operable controlled furling balloon assembly 100 of FIGS. 1-5C in accordance with a preferred embodiment of the present invention.

Figure 6A:
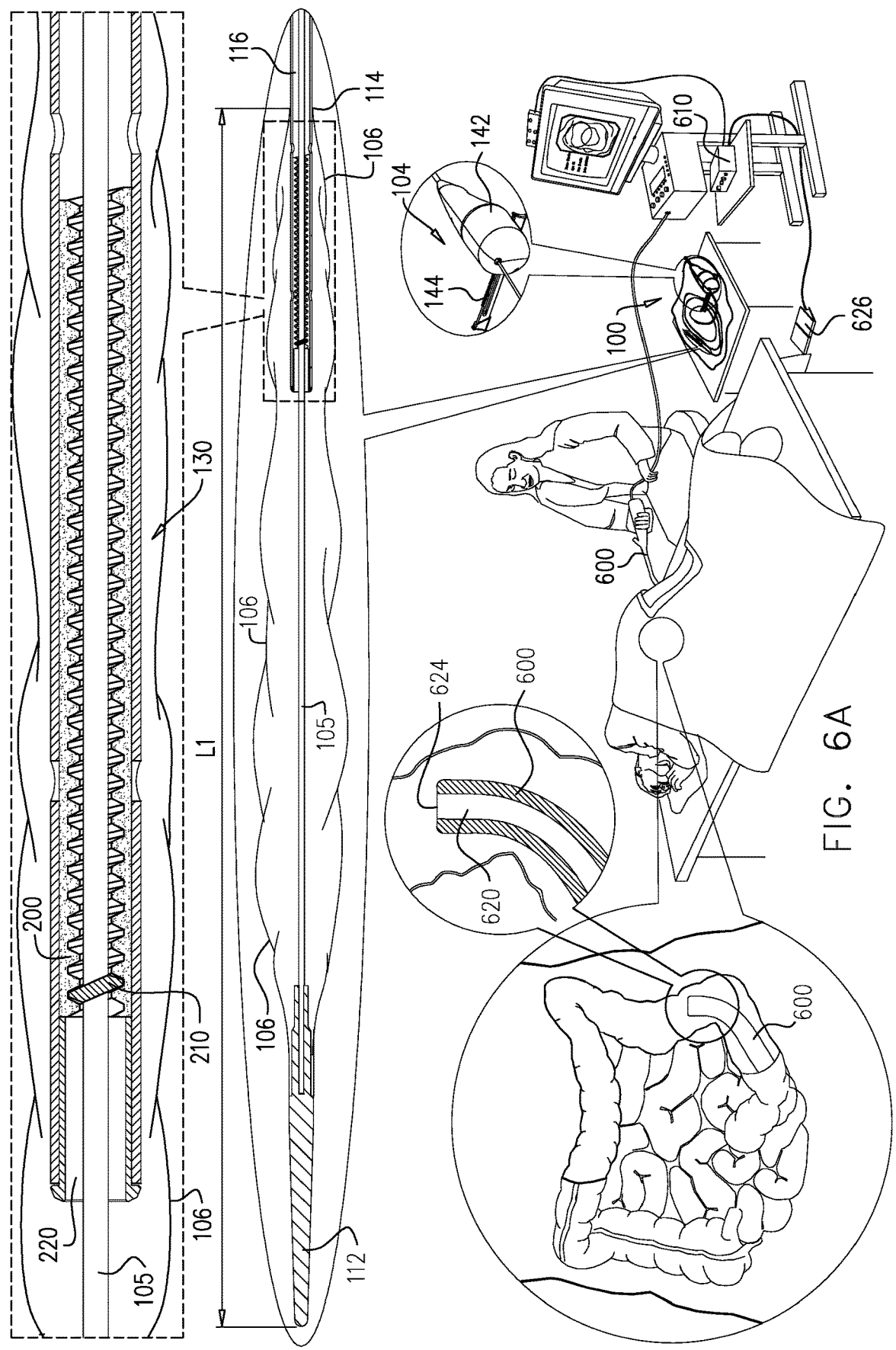

As seen in FIG. 6A, a conventional colonoscopy procedure is initiated, by insertion of a conventional endoscope 600 into operative engagement with a patient. The user-operable controlled furling balloon assembly 100 of the present invention may remain in a sealed package unless and until needed. The balloon sheath 106 in this operative state is seen to be fully unfurled. The longitudinal extent along elongate furling driving element 105 from the rearward end 114 of balloon sheath 106 to the forward end of tip element 112 is indicated to be L1 for this fully unfurled operational state. It is further seen that cam element 210 is at a forward position relative to cam path defining element 200.

Figure 6B:
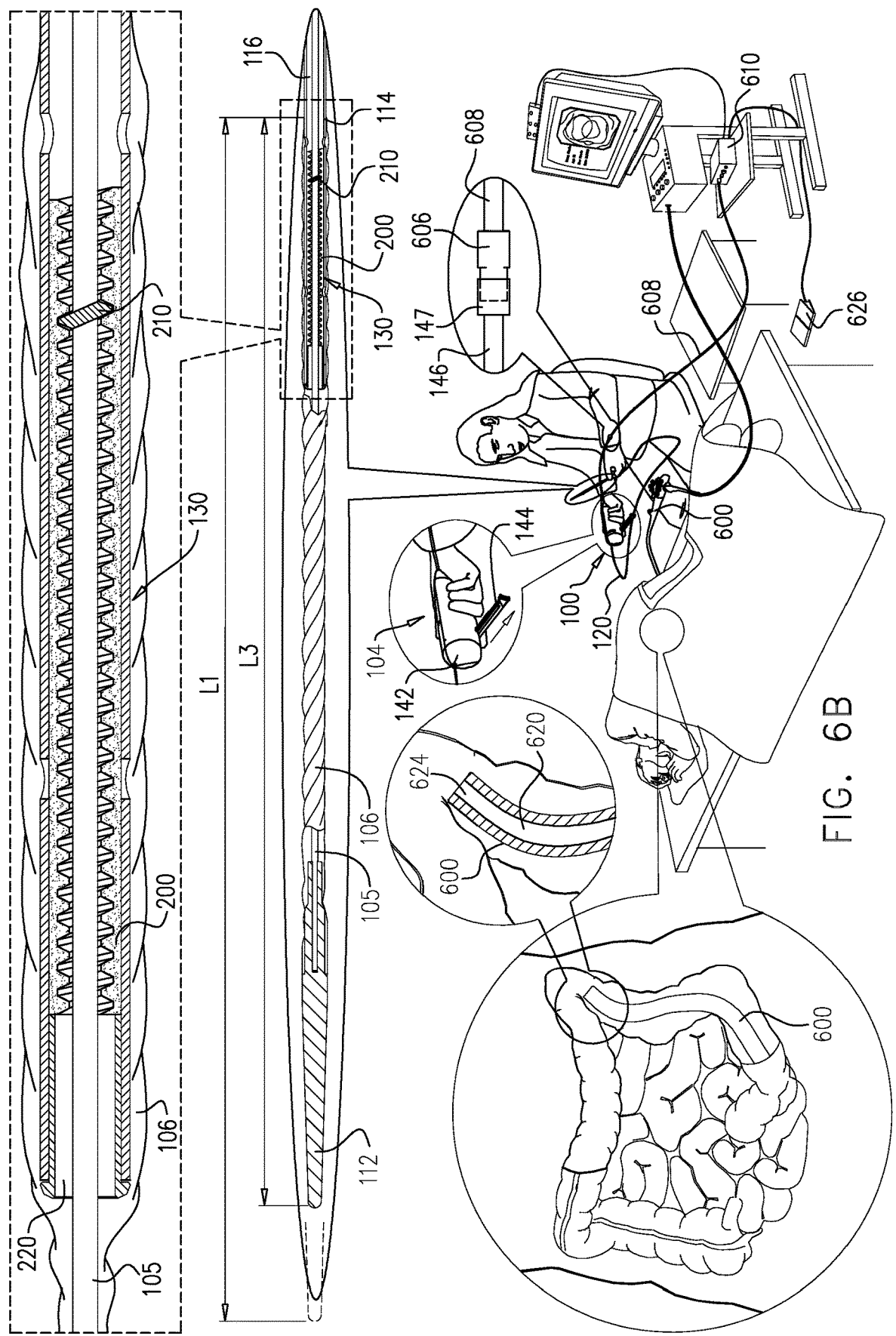

As seen in FIG. 6B, removal of the user-operable controlled furling balloon assembly 100 from its sealed package upon encountering a clinical difficulty in the course of the colonoscopy in which the operator is unable to successfully advance past a bend in the large intestine, typically at the splenic flexure. The operator connects the connector 147 of inflation/deflation connection tube 146 to a corresponding connector 606 of an inflation/deflation tube 608 of an inflation/deflation device 610, preferably a SPARK 2C commercially available from Smart Medical Systems Ltd. of Raanana, Israel.

The balloon sheath 106 is caused to be in a fully furled operative orientation by suitable positioning of manually-manipulatable linear driving element 144 relative to housing 142 of furling control assembly 104. The longitudinal extent along elongate furling driving element 105 from the rearward end 114 of balloon sheath 106 to the forward end of tip element 112 is indicated to be L3 for this fully furled operational state. It is appreciated that L3 is substantially shorter than L1. It is further seen that cam element 210 is at a rearward position relative to cam path defining element 200.

Figure 6C:
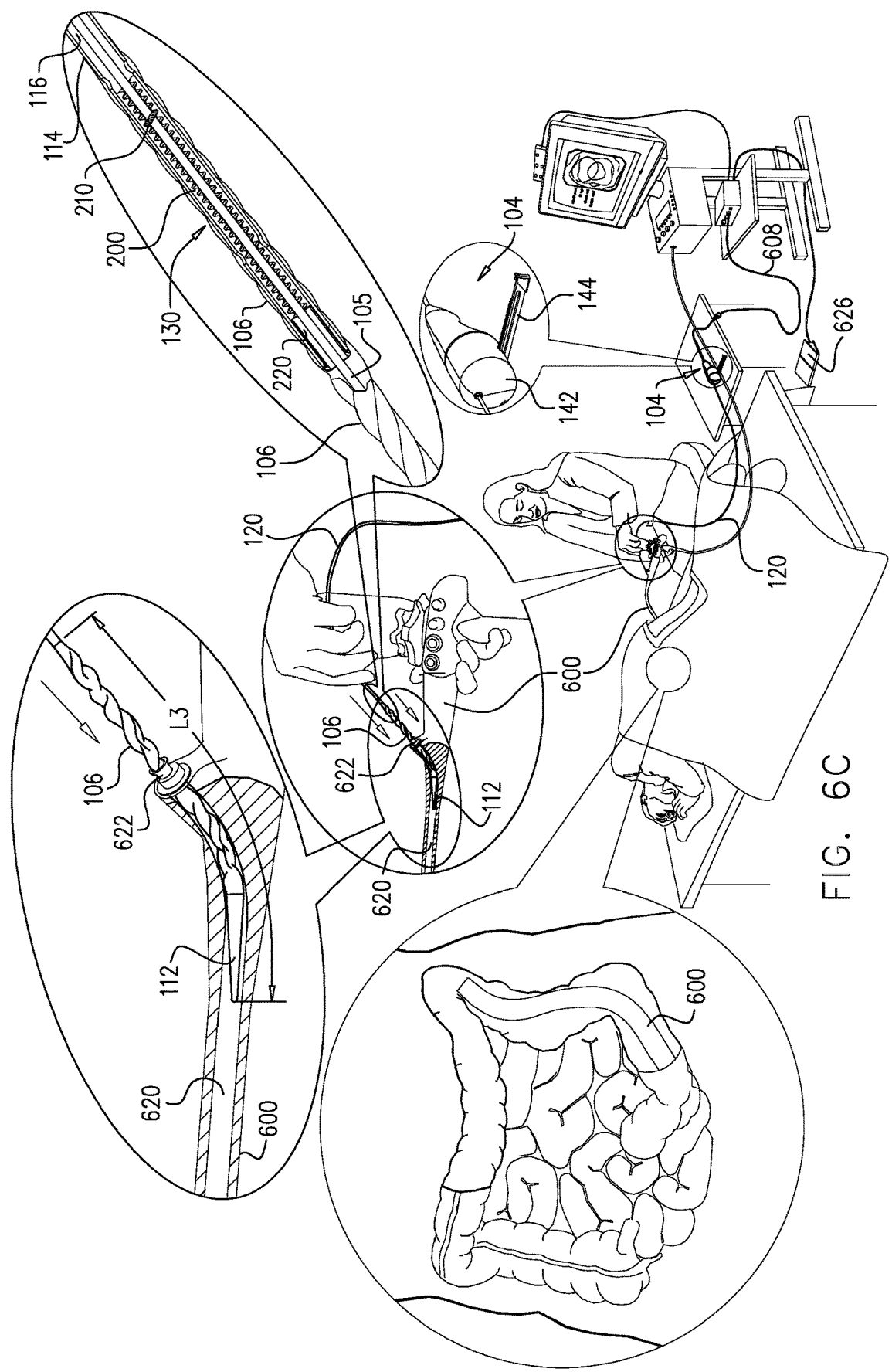

Reference is now made to FIG. 6C, which illustrates insertion of the fully-furled balloon sheath 106 into an instrument channel 620 of endoscope 600 via an instrument channel port 622. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Figure 6D:
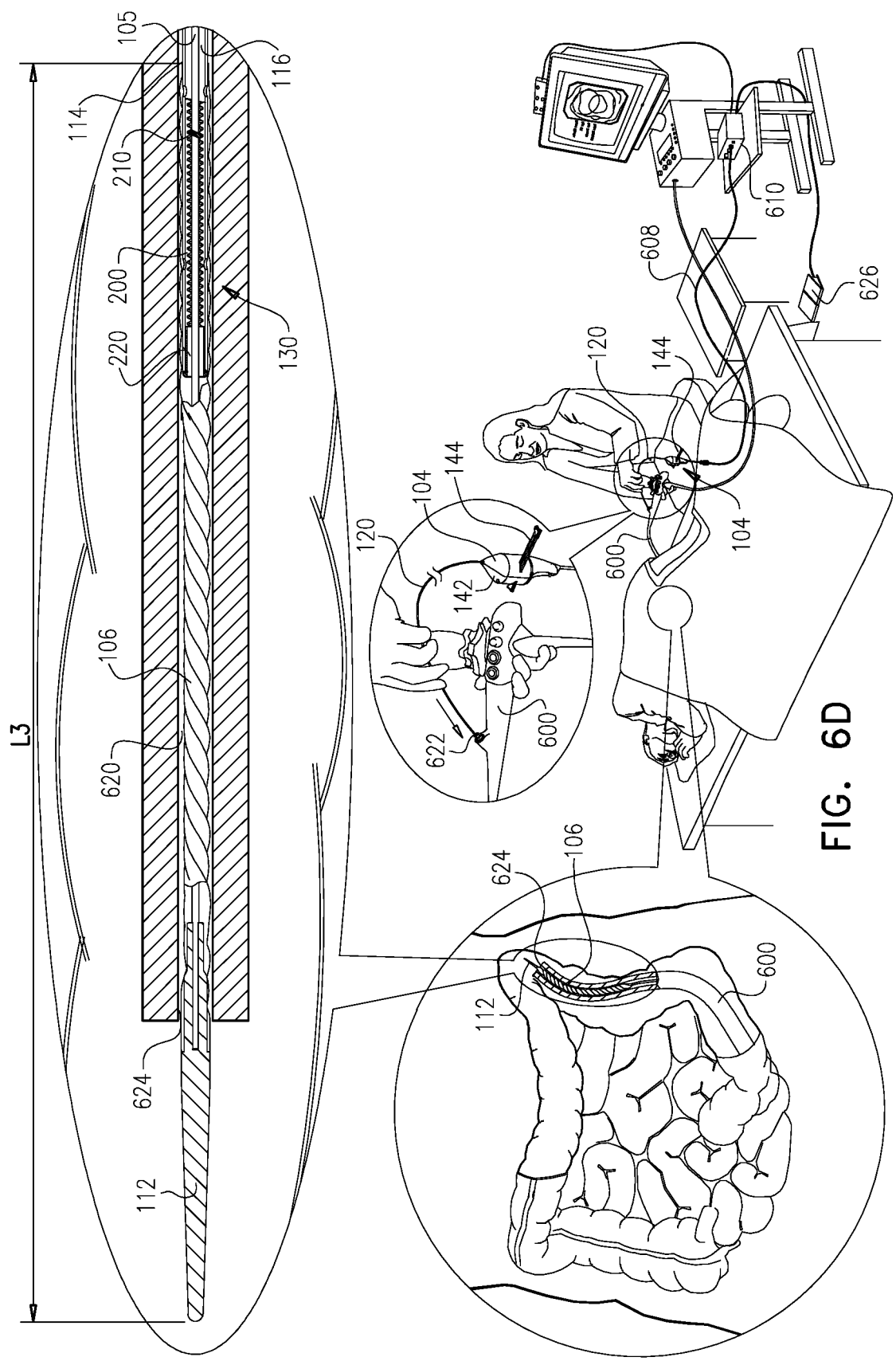

Reference is now made to FIG. 6D, which illustrates further insertion of the fully-furled balloon sheath 106 and the catheter tube 120 into instrument channel 620 of endoscope 600 via instrument channel port 622, such that the tip element 112 extends partially beyond a forward end 624 of the instrument channel 620. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Figure 6E:
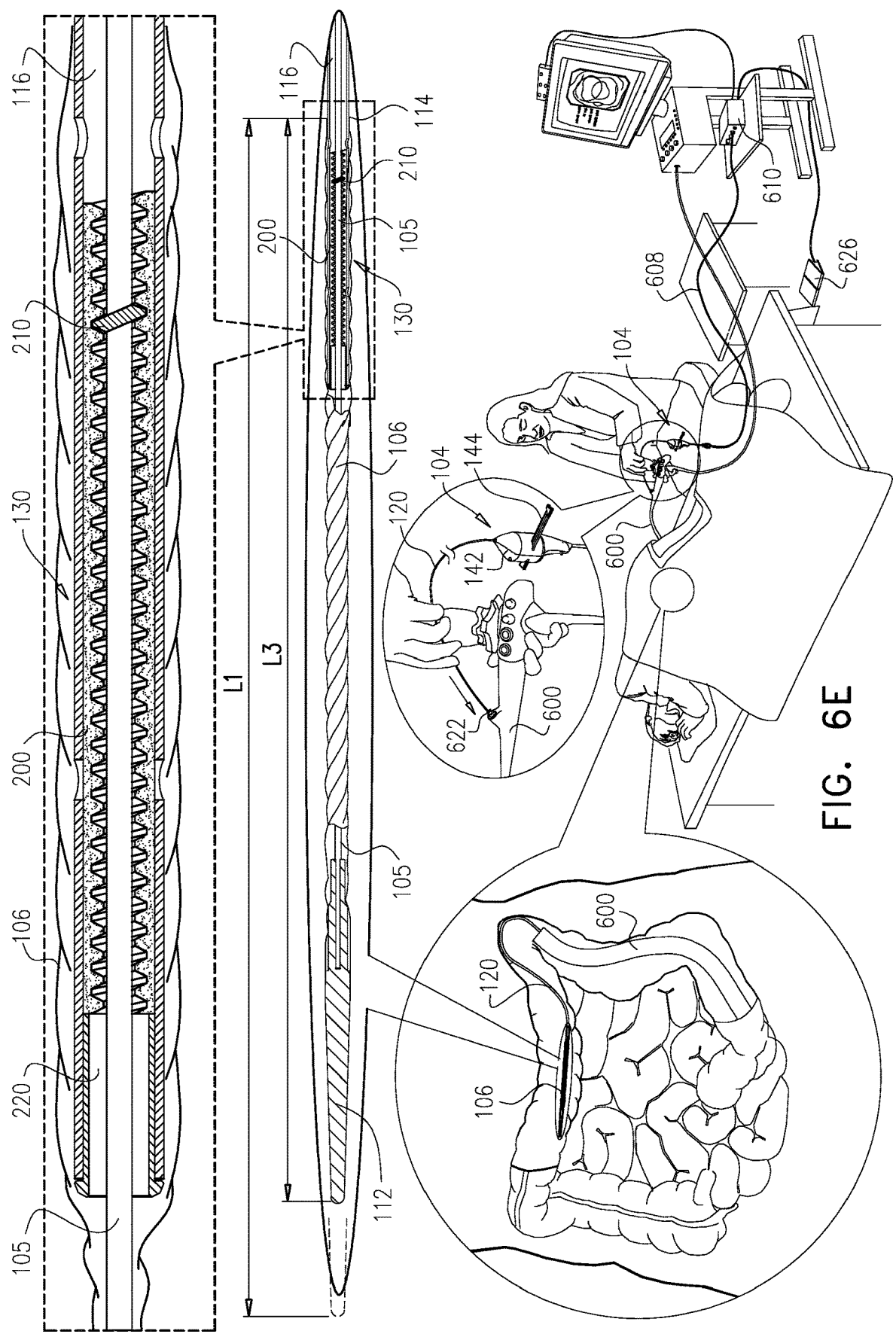

Reference is now made to FIG. 6E, which illustrates still further insertion of the fully-furled balloon sheath 106 and the catheter tube 120 into instrument channel 620 of endoscope 600 via instrument channel port 622, such that the balloon sheath 106 is located beyond a tight curve of the colon, here the splenic flexure. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Figure 6F:
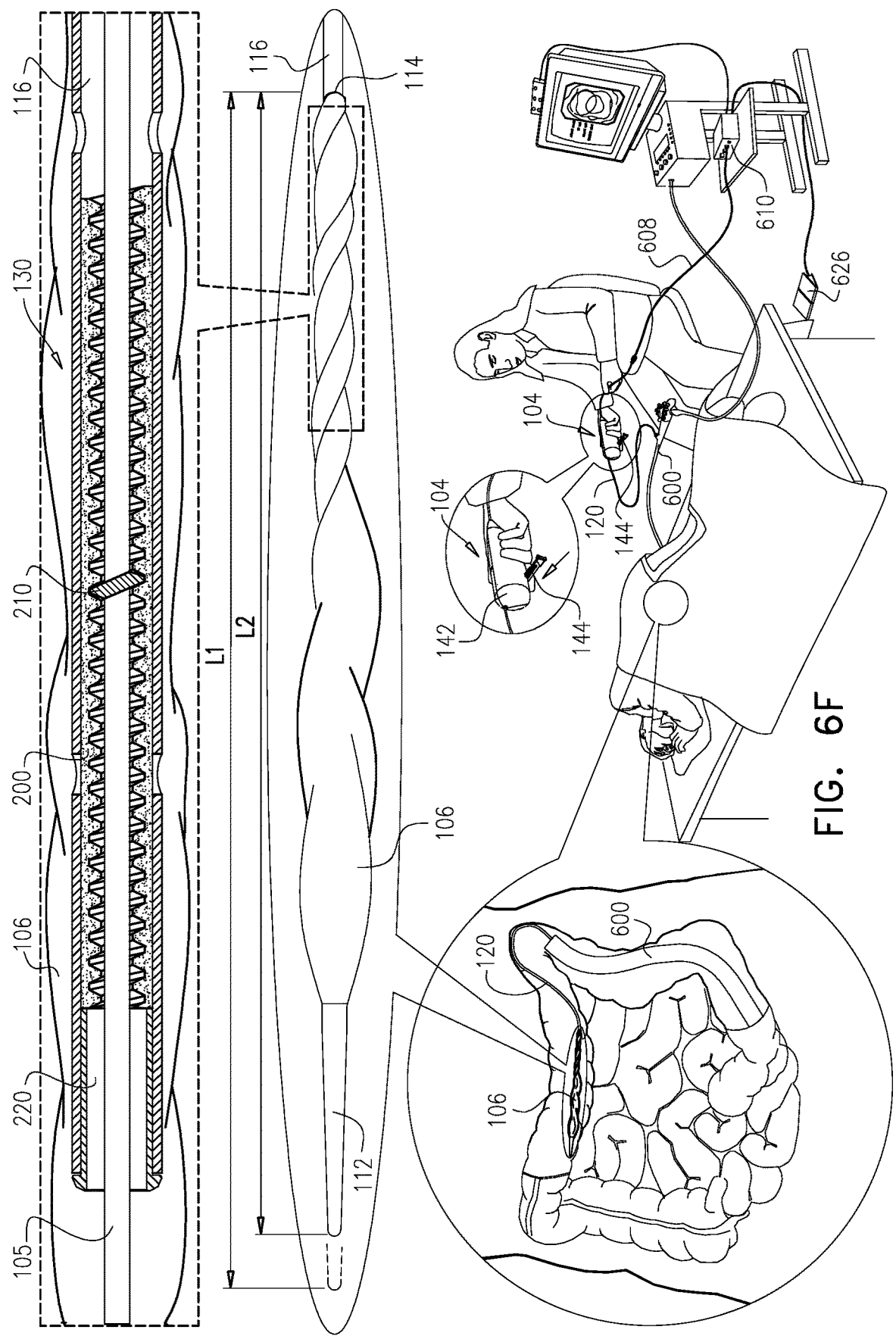

Reference is now made to FIG. 6F, which illustrates partial unfurling of the balloon sheath 106 by operation of furling control assembly 104. It is seen that the longitudinal extent along elongate furling driving element 105 from the rearward end 114 of balloon sheath 106 to the forward end of tip element 112 is L2 for this partially furled operational state, where L2 is shorter than L1 but longer than L3. It is further seen that cam element 210 is at an intermediate position relative to cam path defining element 200, between its forward position and its rearward position.

Figure 6G:
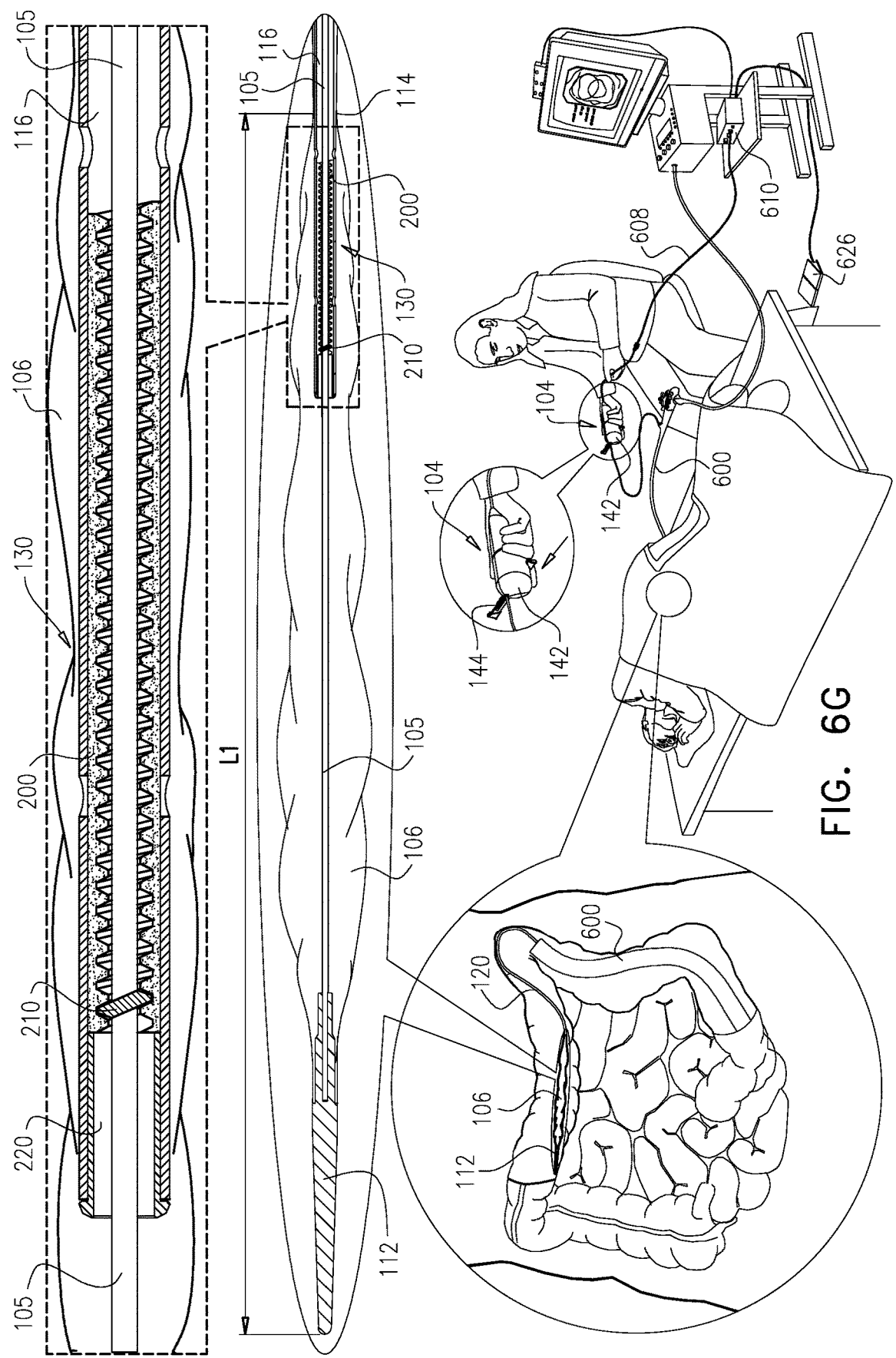

Reference is now made to FIG. 6G, which illustrates full unfurling of the balloon sheath 106 by operation of furling control assembly 104. It is seen that the longitudinal extent along elongate furling driving element 105 from the rearward end 114 of balloon sheath 106 to the forward end of tip element 112 is L1 for this fully unfurled operational state. It is further seen that cam element 210 is at its forward position relative to cam path defining element 200.

Figure 6H:
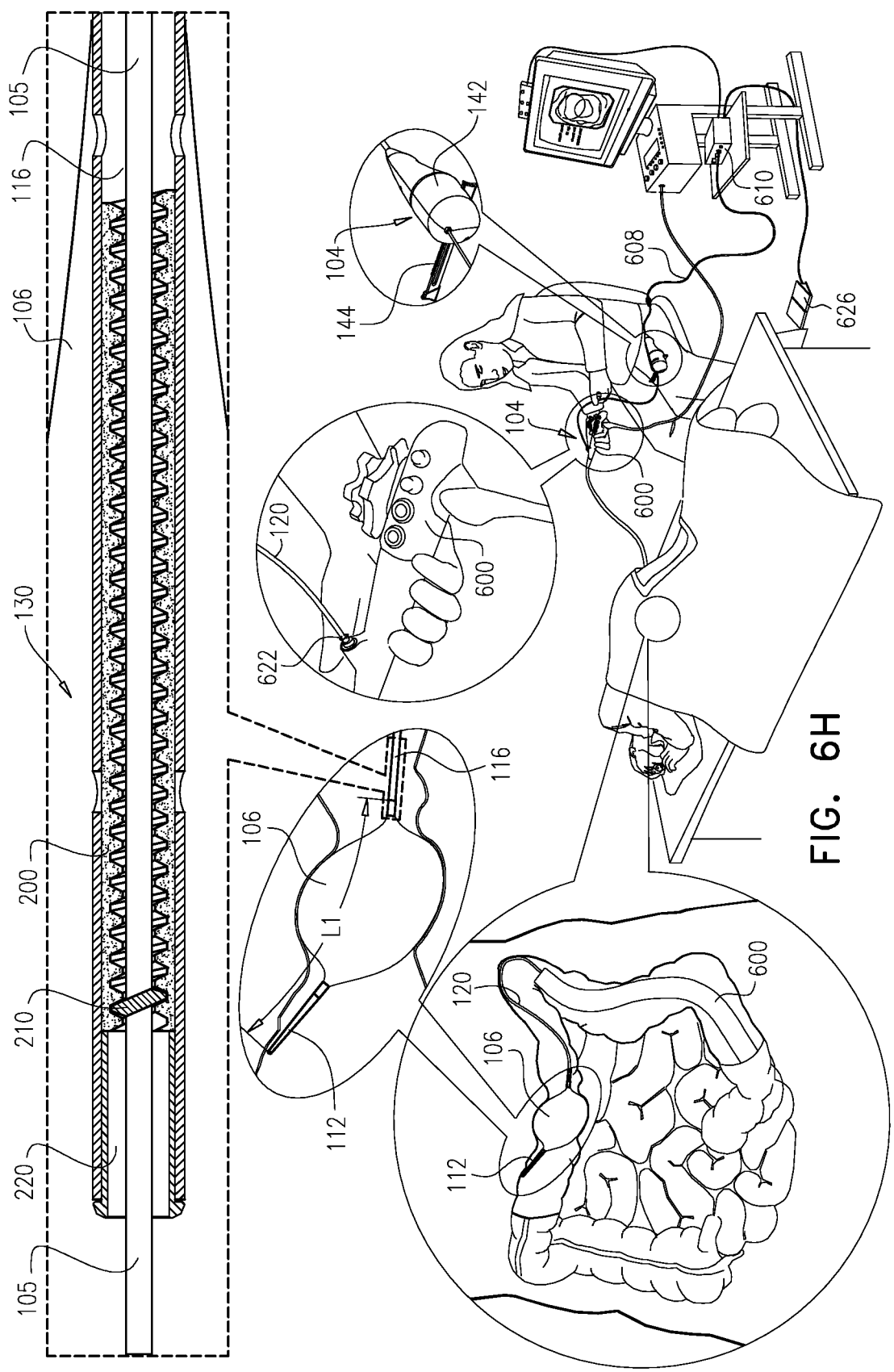
Figure 61:
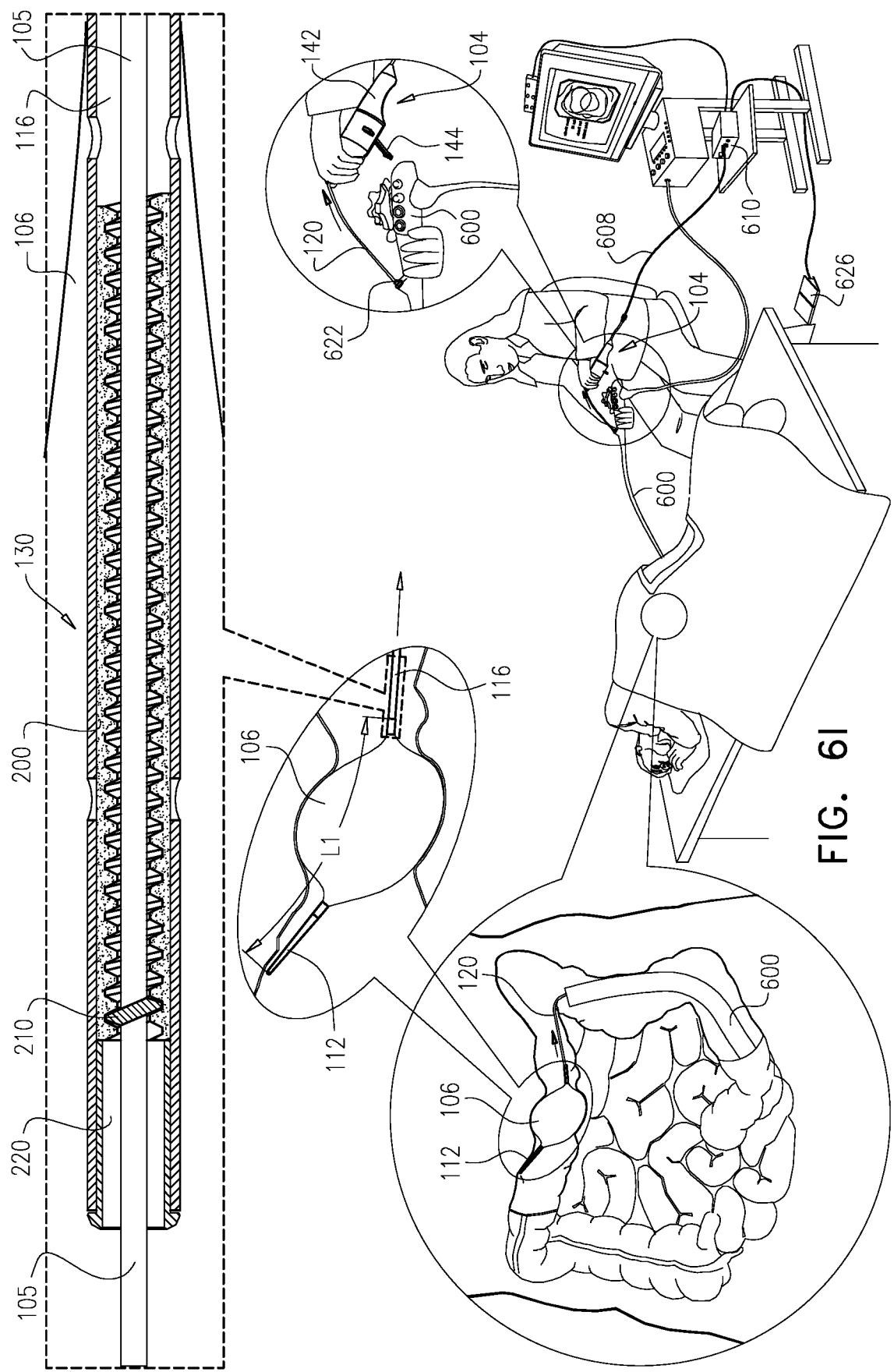

Reference is now made to FIG. 6H, which illustrates inflation of the balloon sheath 106 by operation of inflation/deflation device 610, as by the operator depressing a foot pedal 626. It is seen that the longitudinal extent along elongate furling driving element 105 from the rearward end 114 of balloon sheath 106 to the forward end of tip element 112 is L1 for this fully unfurled, inflated, operational state. It is further seen that cam element 210 is at its forward position relative to cam path defining element 200.

Reference is now made to FIG. 6I, which illustrates pulling back on the catheter tube 120 by the operator. It is seen that the longitudinal extent along elongate furling driving element 105 from the rearward end 114 of balloon sheath 106 to the forward end of tip element 112 is L1 for this fully unfurled, inflated, operational state. It is further seen that cam element 210 is at its forward position relative to cam path defining element 200.

Figure 6J:
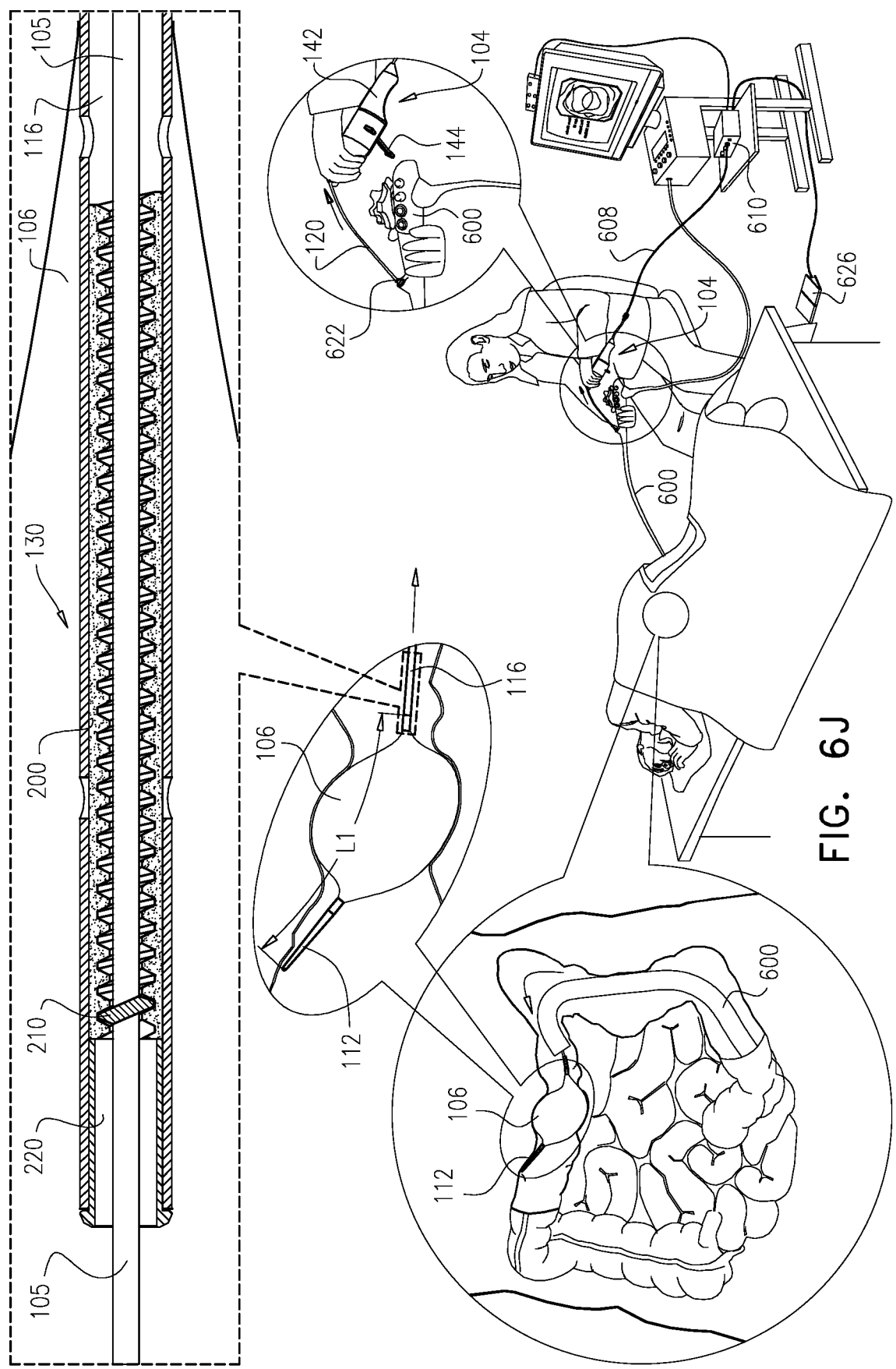

Reference is now made to FIG. 6J, which illustrates pushing the endoscope 600 forwardly using the catheter tube 120 as a guide until it reaches the rearward end 114 of balloon sheath 106. It is seen that the longitudinal extent along elongate furling driving element 105 from the rearward end 114 of balloon sheath 106 to the forward end of tip element 112 is L1 for this fully unfurled, inflated, operational state. It is further seen that cam element 210 is at its forward position relative to cam path defining element 200.

Figure 6K:
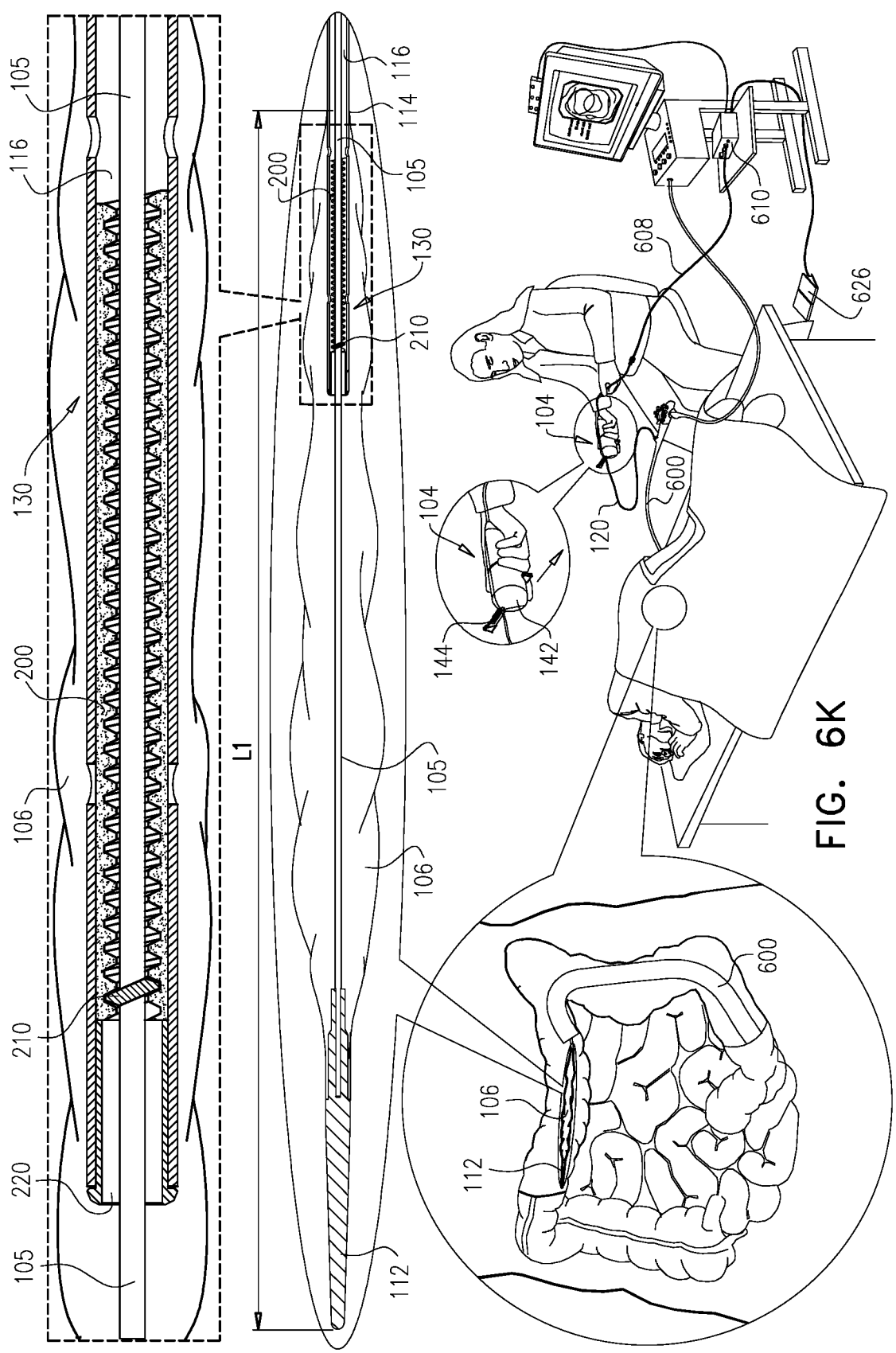

Reference is now made to FIG. 6K, which illustrates deflation of the fully unfurled balloon sheath 106. It is seen that the longitudinal extent along elongate furling driving element 105 from the rearward end 114 of balloon sheath 106 to the forward end of tip element 112 is L1 for this fully unfurled, deflated, operational state. It is further seen that cam element 210 is at its forward position relative to cam path defining element 200.

Figure 6L:
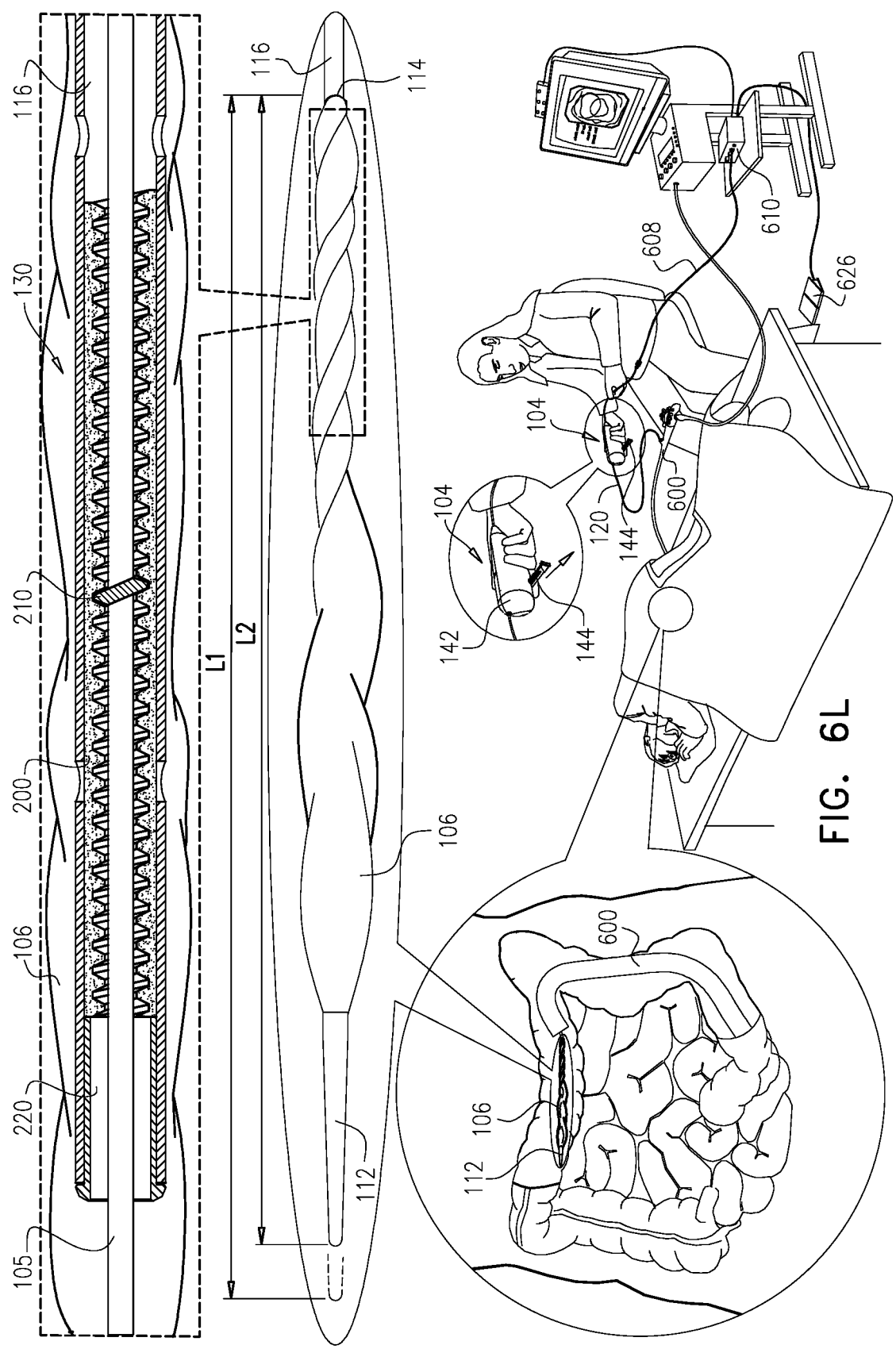

Reference is now made to FIG. 6L, which illustrates partial furling of balloon sheath 106. It is seen that the longitudinal extent along elongate furling driving element 105 from the rearward end 114 of balloon sheath 106 to the forward end of tip element 112 is L2 for this partially furled operational state, where L2 is shorter than L1 but longer than L3. It is further seen that cam element 210 is at an intermediate position relative to cam path defining element 200, between its forward position and its rearward position.

Figure 6M:
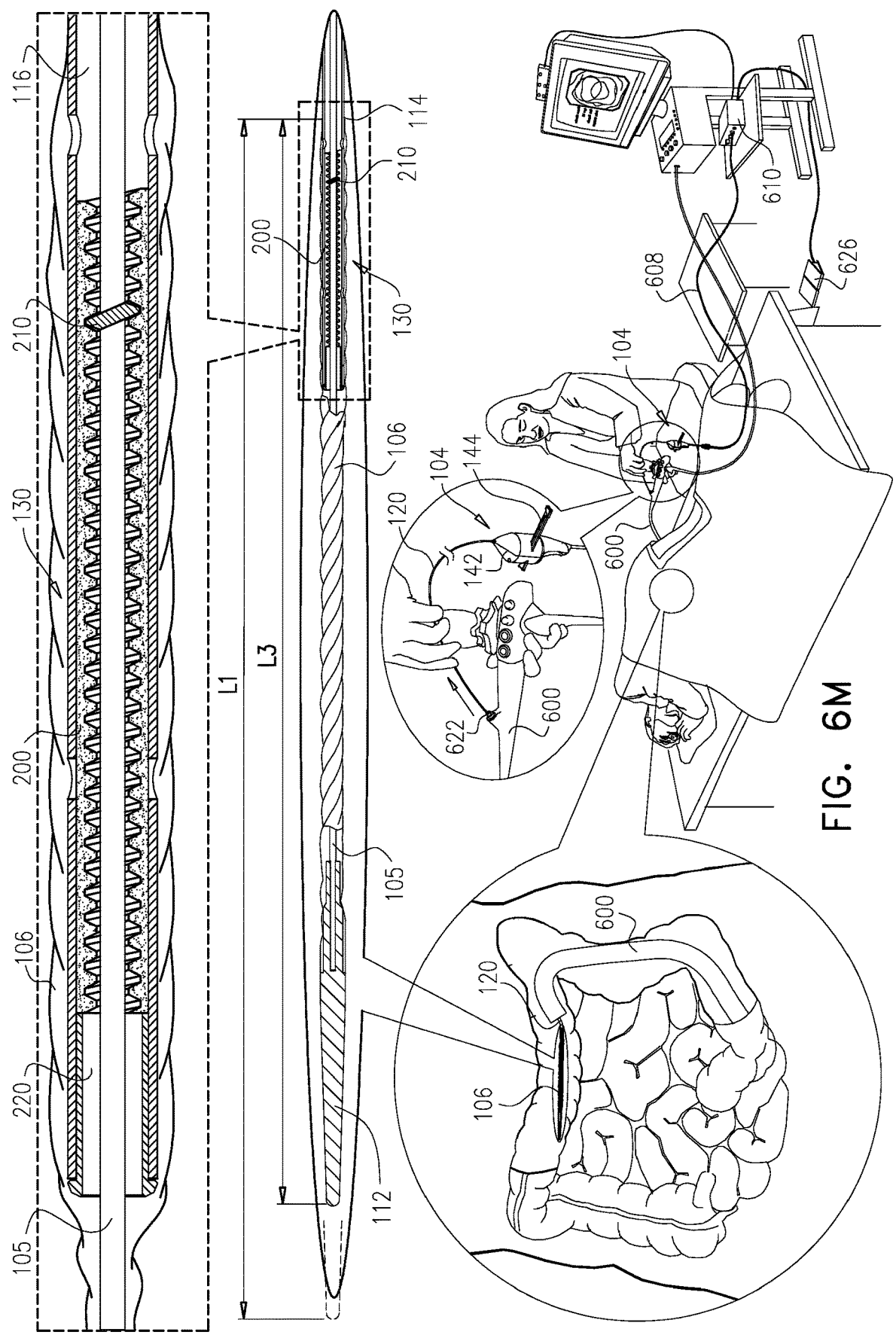

Reference is now made to FIG. 6M, which illustrates retraction and reinsertion of the fully furled balloon sheath 106 into instrument channel 620 via end 624. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200. It is a particular feature of an embodiment of the present invention that bunching of the balloon sheath 106 and consequent difficulty of retraction of the balloon sheath 106 into the instrument channel is obviated.

Figure 6N:
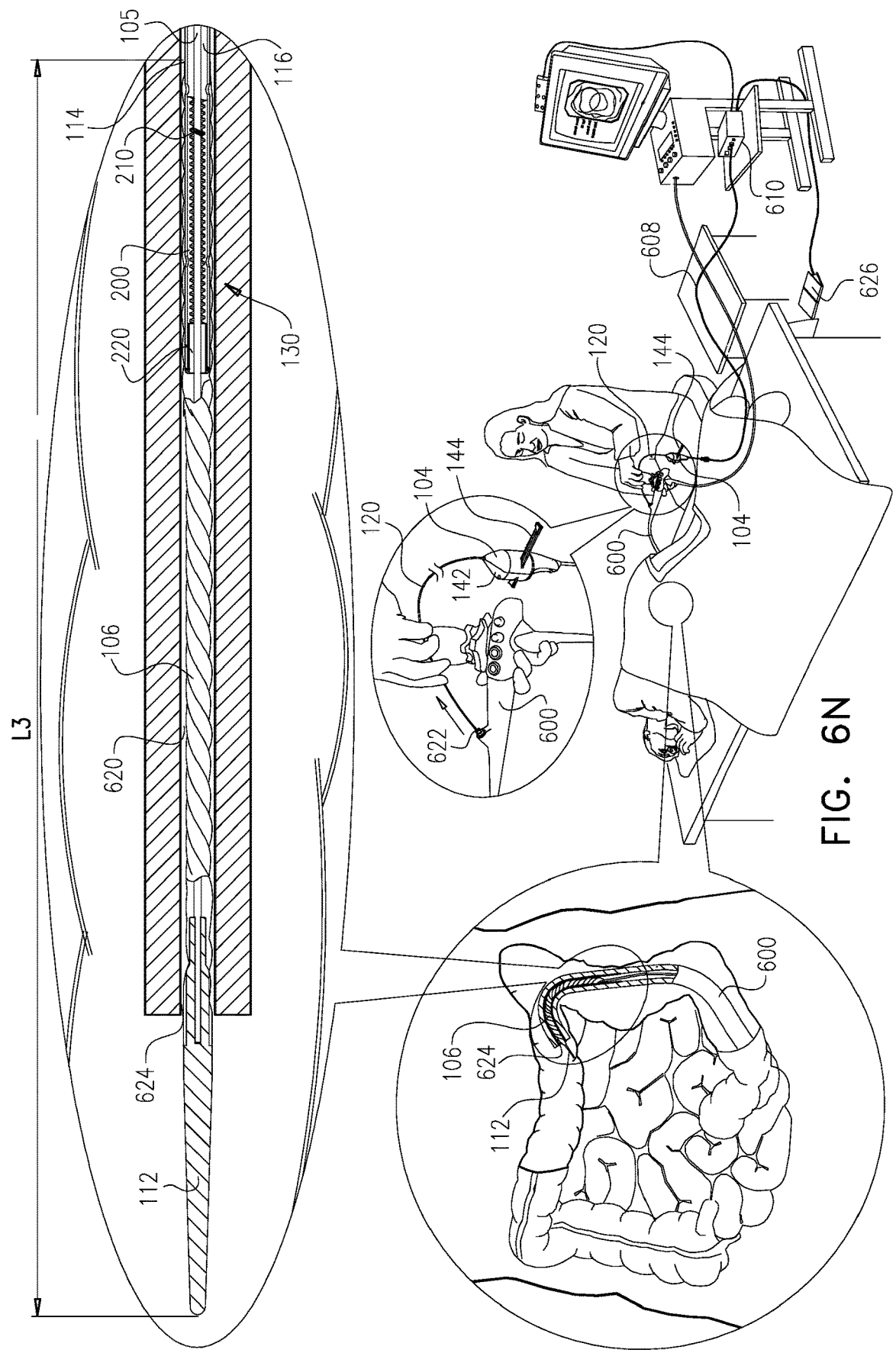
Figure 60:
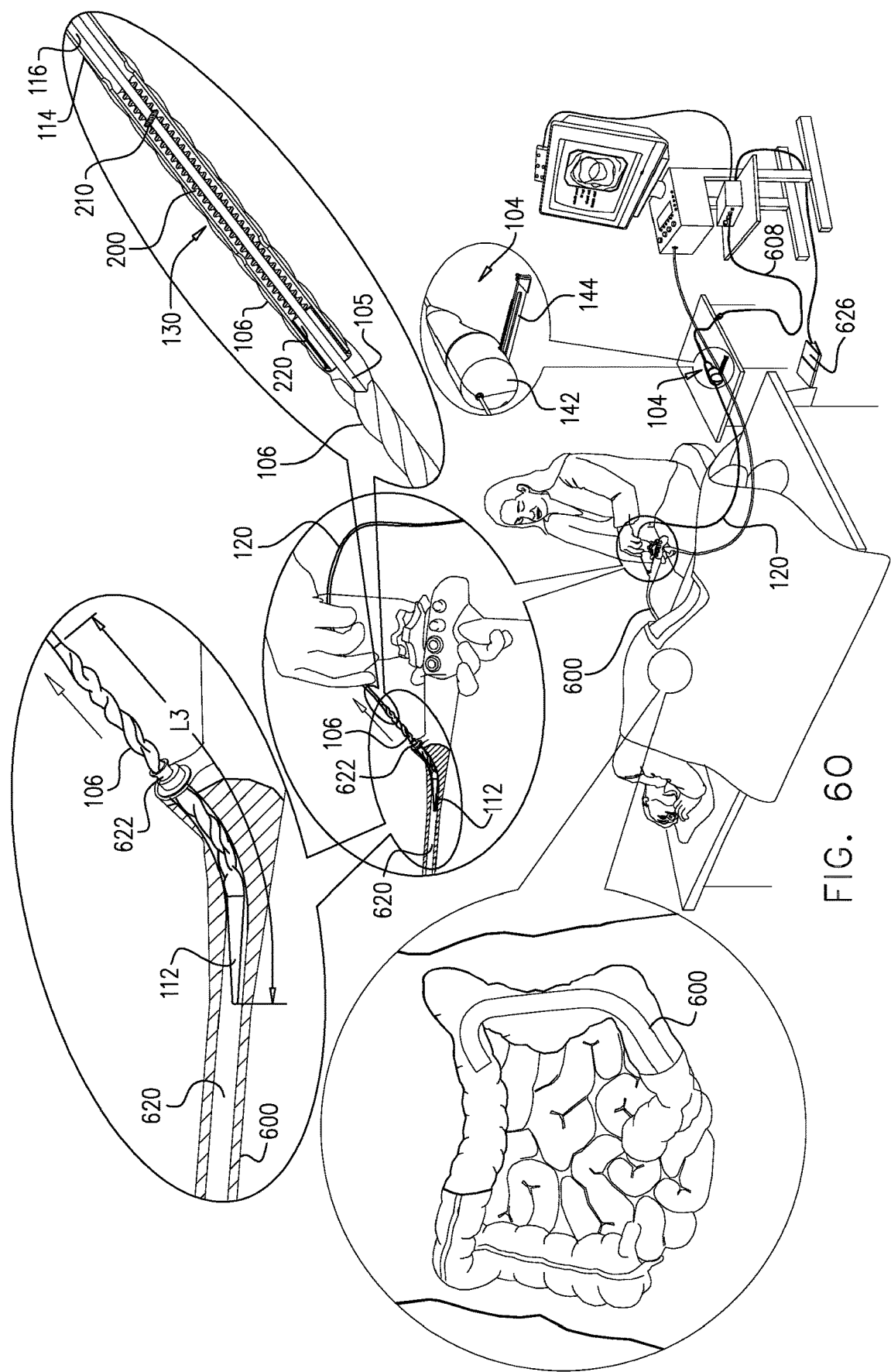

Reference is now made to FIG. 6N, which illustrates further retraction of the fully furled balloon sheath 106 into instrument channel 620. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Reference is now made to FIG. 6O, which illustrates removal of the fully furled balloon sheath 106 from instrument channel 620 via port 622. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Figure 6P:
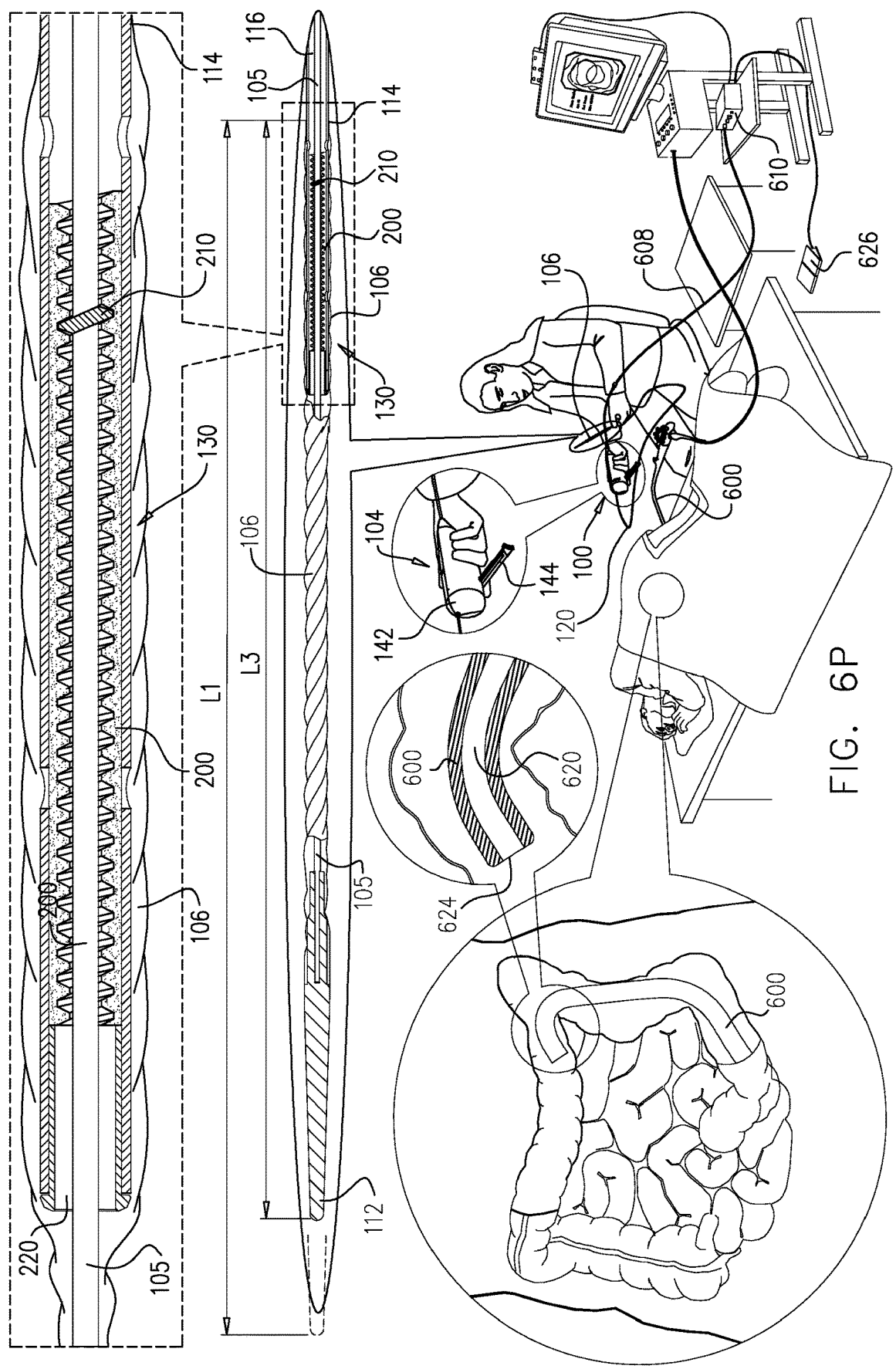

Reference is now made to FIG. 6P, which illustrates the endoscope system including the user-operable controlled furling balloon assembly 100 following removal of the fully furled balloon sheath 106 from instrument channel 620 via port 622. It is seen that the longitudinal extent along elongate furling driving element 105 from the rearward end 114 of balloon sheath 106 to the forward end of tip element 112 is L3 for this fully furled operational state. It is further seen that cam element 210 is at its rearward position relative to cam path defining element 200.

Figure 8:
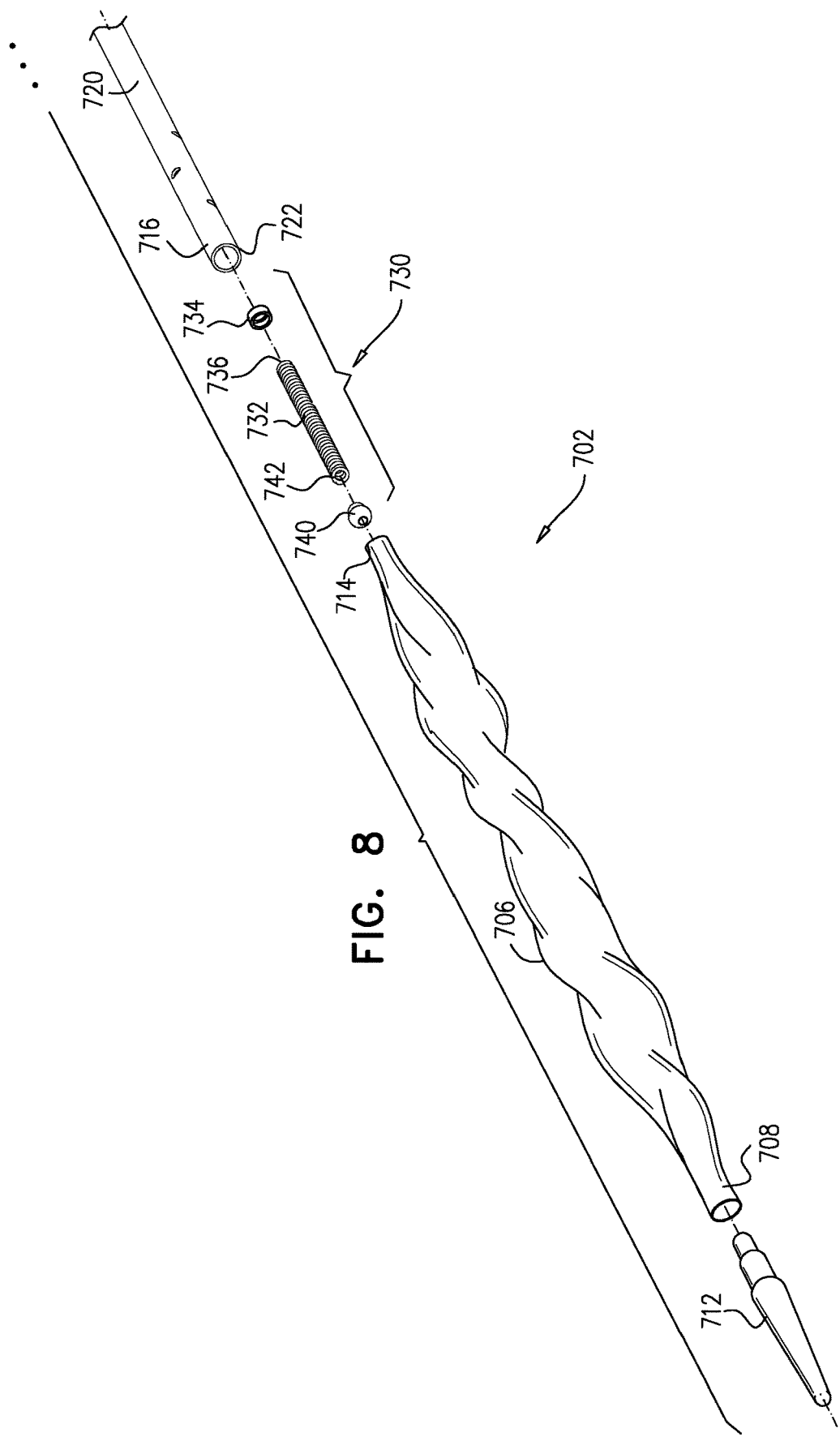
FIG. 8 is a simplified exploded view illustration of the configured furl balloon assembly of FIG. 7.

Reference is now made to FIG. 7, which is a simplified partially pictorial, partially sectional, illustration of a user-operable controlled furling balloon assembly 700, associatable with an endoscope in accordance with a preferred embodiment of the present invention, including a configured furl balloon assembly 702 and a furling control assembly 704, to FIG. 8, which is a simplified exploded view illustration of the configured furl balloon assembly 702 of FIG. 7, to FIG. 2B, which is a simplified exploded view illustration of the furling control assembly 704 of FIG. 7, and to FIG. 2C, which is a simplified partially cut away illustration of the furling control assembly 704 of FIGS. 7 and 2B. It is appreciated that the furling control assembly 704 is identical to furling control assembly 104 and accordingly, for the sake of conciseness, the description thereof is not repeated here.

In accordance with a preferred embodiment of the present invention, the user-operable controlled furling balloon assembly 700 includes an elongate furling driving element 705, preferably in the form of a wire, preferably formed of stainless steel, which is retractable and rotatable about an elongate axis thereof.

As seen in FIG. 8, the configured furl balloon assembly 702 preferably includes a furlable balloon sheath 706, which surrounds a forward portion of the elongate furling driving element 705 (FIG. 7) and is coupled at a forward end 708 thereof via a tip element 712 to the elongate furling driving element 705 (FIG. 7) and at a rearward end 714 thereof to a forward portion 716 of a catheter tube 720 having a forward end 722.

The configured furl balloon assembly 702 also comprises a furling/retraction controlling assembly 730. Furling/retraction controlling assembly 730 comprises an elongate compression coil spring 732 which is positioned about the elongate furling driving element 705 and whose rearward displacement relative to the catheter tube 720 is limited by a spring seat 734, which is fixedly coupled to the catheter tube 720, at a location forward of the rearward end 714 of the balloon sheath 706. Spring seat 734 is apertured to permit rotation and axial displacement of elongate furling driving element 705 relative thereto. A rearward end 736 of spring 732 is normally compressed against spring seat 734.

Furling/retraction controlling assembly 730 also comprises a spring engagement element 740, which is fixed to elongate furling driving element 705 for rotation and axial displacement thereof. Spring engagement element 740 normally is rotatably compressed against a forward end 742 of spring 732.

It is a particular feature of this embodiment that furling/retraction controlling assembly 730 is operative for limiting an extent of retraction of the elongate furling driving element 705 (FIG. 7) to be a function of an extent of furling of the balloon sheath 706, thereby limiting a maximum outer diameter of the balloon sheath 706 when furled and preventing stacking of the balloon sheath 706. In this embodiment, the limiting is achieved by the compressive force exerted by spring 732 which preferably generally linearly increases as a function of the extent of furling of balloon sheath 706 and consequent retraction of elongate furling driving element 705 relative to catheter tube 720.

Figure 9A:
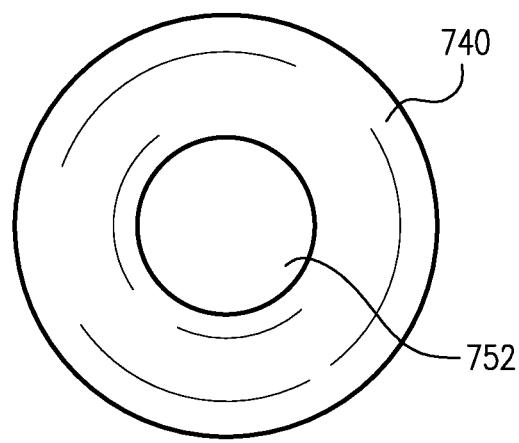
FIGS. 9A, 9B and 9C are simplified illustrations of a spring engaging element useful in the configured furl balloon assembly of FIG. 8.
Figure 9B:
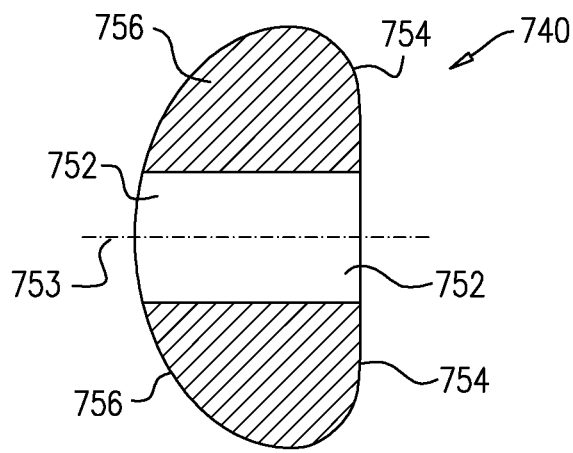
Figure 9C:
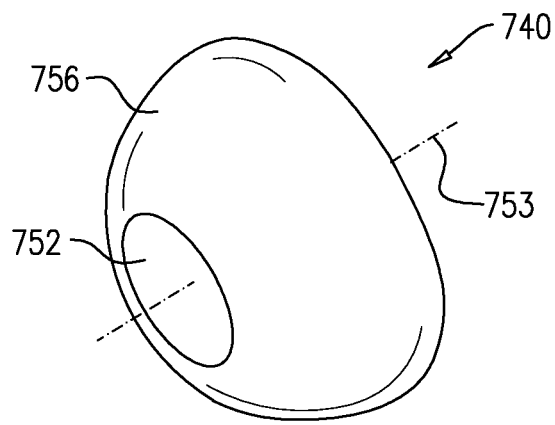
Figure 10A:
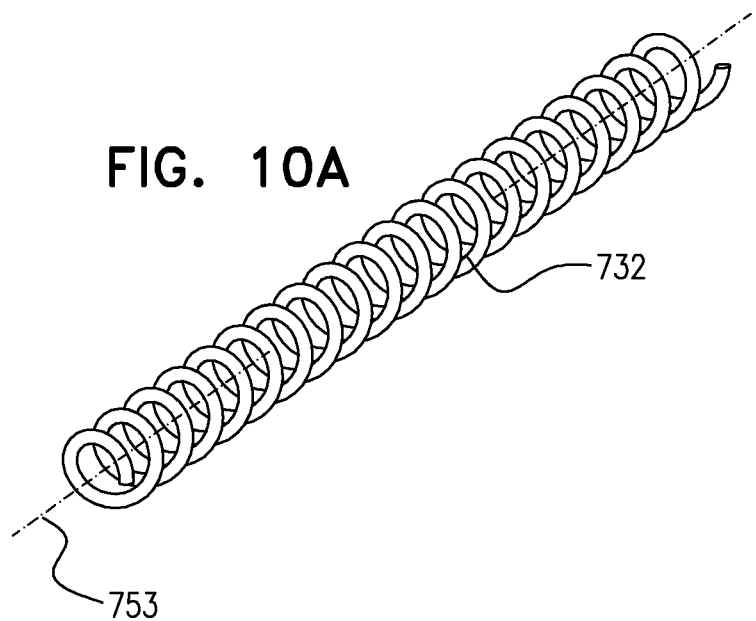
FIGS. 10A, 10B and 10C are simplified illustrations of a compression spring useful in the configured furl balloon assembly of FIG. 8.
Figure 10B:
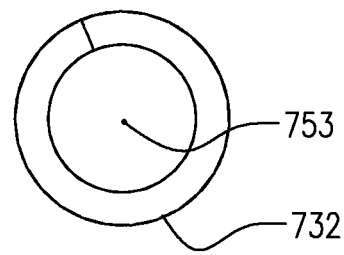
Figure 10C:
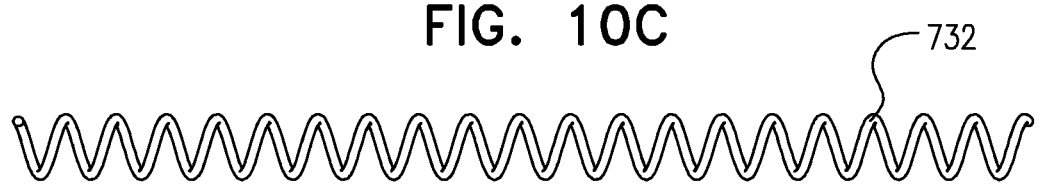
Figure 11A:
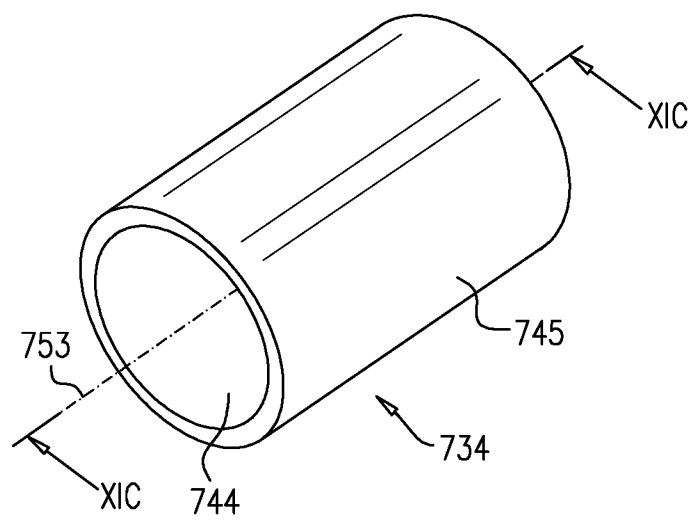
FIGS. 11A, 11B and 11C are simplified illustrations of a spring seat useful in the configured furl balloon assembly of FIG. 8, FIG. 11C being a partially cut away view taken along lines XIC-XIC of FIG. 11A.
Figure 11B:
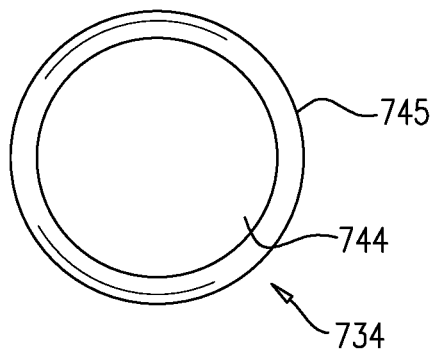
Figure 11C:
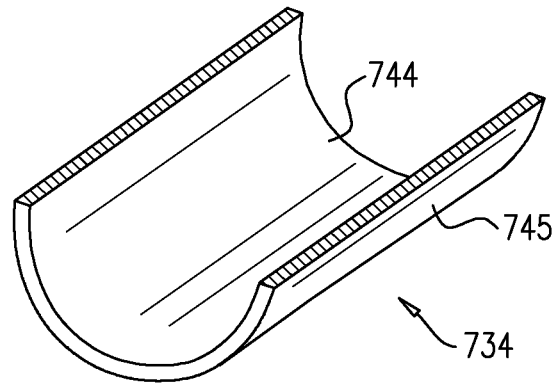

Reference is additionally made to FIGS. 9A-9C, which are simplified illustrations of spring engagement element 740, to FIGS. 10A-10C, which are simplified illustrations of spring 732, and to FIGS. 11A-11C, which are simplified illustrations of spring seat 734.

As seen in FIGS. 10A-10C, spring 732 is a conventional linear coil spring, which is wholly or partially seated within forward end 716 of catheter tube 720. Rearward axial displacement of spring 732 is limited by spring seat 734, which, as seen in FIGS. 11A-11C, is preferably a hollow cylindrical element, having a throughgoing bore 744, which is fixed, as by an adhesive on an outer cylindrical surface 745 thereof, to an interior circumferential wall surface of catheter tube 720 at a location forward of the rearward end 714 of the balloon sheath 706.

Spring engagement element 740, seen in FIGS. 9A-9C, is preferably a generally annular element having a central aperture 752, at which it is fixedly attached to elongate furling driving element 705 at a location therealong which is preferably selected such that at all times it generally applies a linear compressive force to spring 732 against spring seat 734, along a longitudinal axis 753 defined by elongate furling driving element 705. Spring engagement element 740 preferably has a generally flat spring engagement outer surface 754 and a generally curved remaining outer surface 756.

It is appreciated that the arrangement described above, whereby spring engagement element 740 is fixed to elongate furling driving element 705 for both rotation and longitudinal displacement together therewith generally along longitudinal axis 753 in linear compressive engagement with spring 732, is effective for limiting an extent of retraction of the elongate furling driving element 705 to be a function of an extent of furling of the balloon sheath 706, thereby limiting a maximum outer diameter of the balloon sheath 706 when furled and preventing stacking of the balloon sheath 706.

It is appreciated that force/compression characteristic of the spring 732 defines the above function, namely the permitted relationship between the extent of furling of the balloon sheath 706 and the extent of elongate retraction of the elongate furling driving element 705. Establishing the relationship between the extent of furling of the balloon sheath 706 and the extent of elongate retraction of the elongate furling driving element 705 is effective to prevent at least one of the following effects:

premature retraction of the elongate furling driving element 705, which would lead to bunching of the balloon sheath 706; excessive retraction of the elongate furling driving element 705, which would lead to bunching of the balloon sheath 706;

insufficient retraction of the elongate furling driving element 705, which would lead to bowing of the elongate furling driving element 705 and consequent difficulties in retraction of the configured furl balloon assembly 700 into and passage thereof through the instrument channel of an endoscope.

Reference is now made to FIGS. 12A, 12B, 12C, 12D, 12E, 12F, 12G, 12H, 12I, 12J, 12K, 12L, 12M, 12N, 12O and 12P, which are simplified pictorial illustrations of operation of an endoscope system including the user-operable controlled furling balloon assembly 700 of FIGS. 7-11C in accordance with a preferred embodiment of the present invention.

Figure 12A:
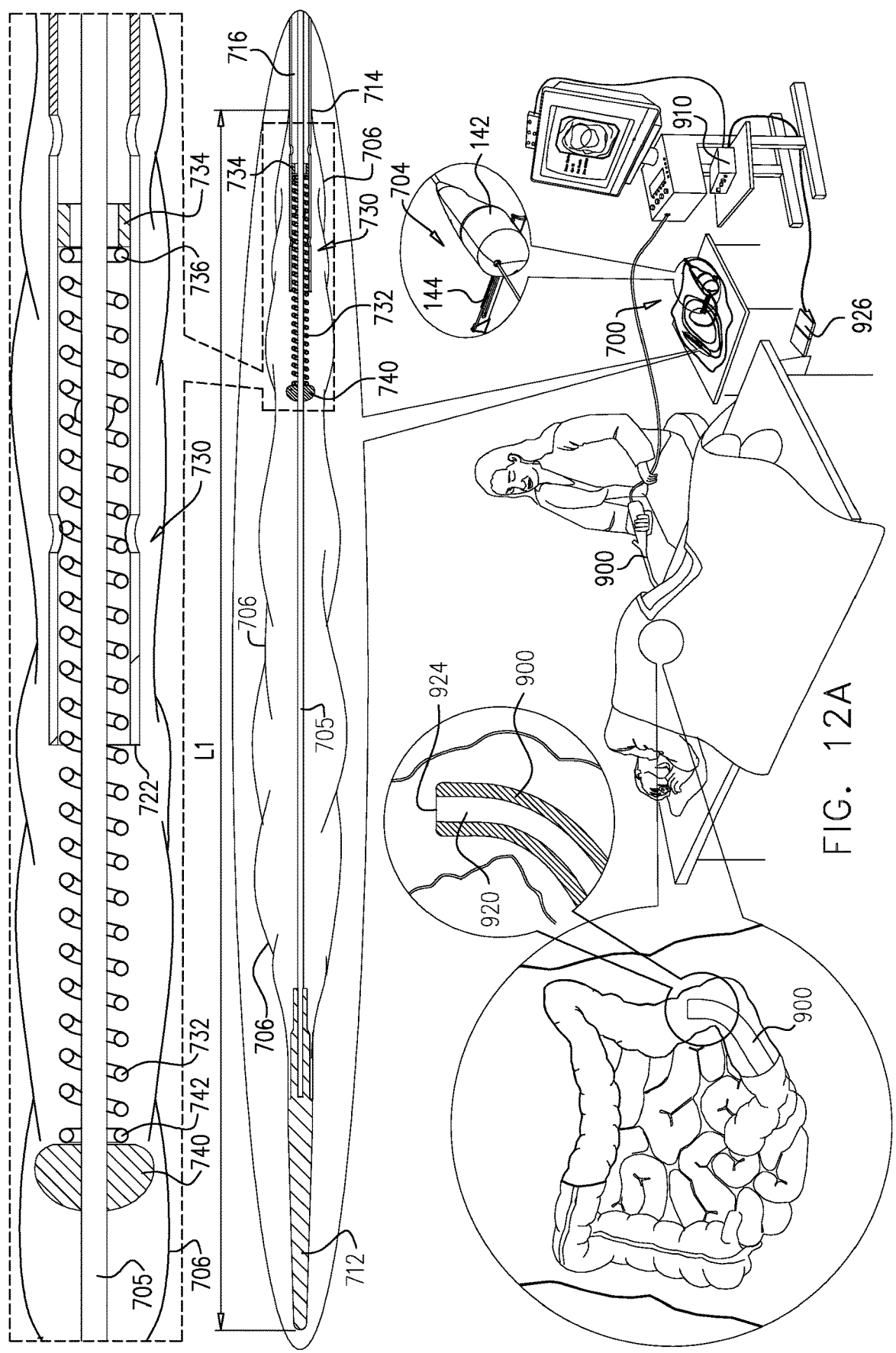

As seen in FIG. 12A, a conventional colonoscopy procedure is initiated, by insertion of a conventional endoscope 900 into operative engagement with a patient. The user-operable controlled furling balloon assembly 700 of the present invention may remain in a sealed package unless and until needed. The balloon sheath 706 in this operative state is seen to be fully unfurled. The longitudinal extent along elongate furling driving element 705 from the rearward end 714 of balloon sheath 706 to the forward end of tip element 712 is indicated to be L1 for this fully unfurled operational state. It is further seen that spring engagement element 740 is at a forward position relative to forward end 722 of catheter tube 720.

As seen in FIG. 12B, removal of the user-operable controlled furling balloon assembly 700 from its sealed package upon encountering a clinical difficulty in the course of the colonoscopy in which the operator is unable to successfully advance past a bend in the large intestine, typically at the splenic flexure. The operator connects the connector 147 of inflation/deflation connection tube 146 of furling control assembly 704 to a corresponding connector 906 of an inflation/deflation tube 908 of an inflation/deflation device 910, preferably a SPARK 2C, commercially available from Smart Medical Systems Ltd. of Raanana, Israel.

The balloon sheath 706 is caused to be in a fully furled operative orientation by suitable positioning of manually-manipulatable linear driving element 144 relative to housing 142 of furling control assembly 704. The longitudinal extent along elongate furling driving element 705 from the rearward end 714 of balloon sheath 706 to the forward end of tip element 712 is indicated to be L3 for this fully furled operational state. It is appreciated that L3 is substantially shorter than L1. It is further seen that spring engagement element 740 is at a rearward position, abutting forward edge 722 of catheter tube 720 and spring 732 is fully compressed.

Figure 12C:
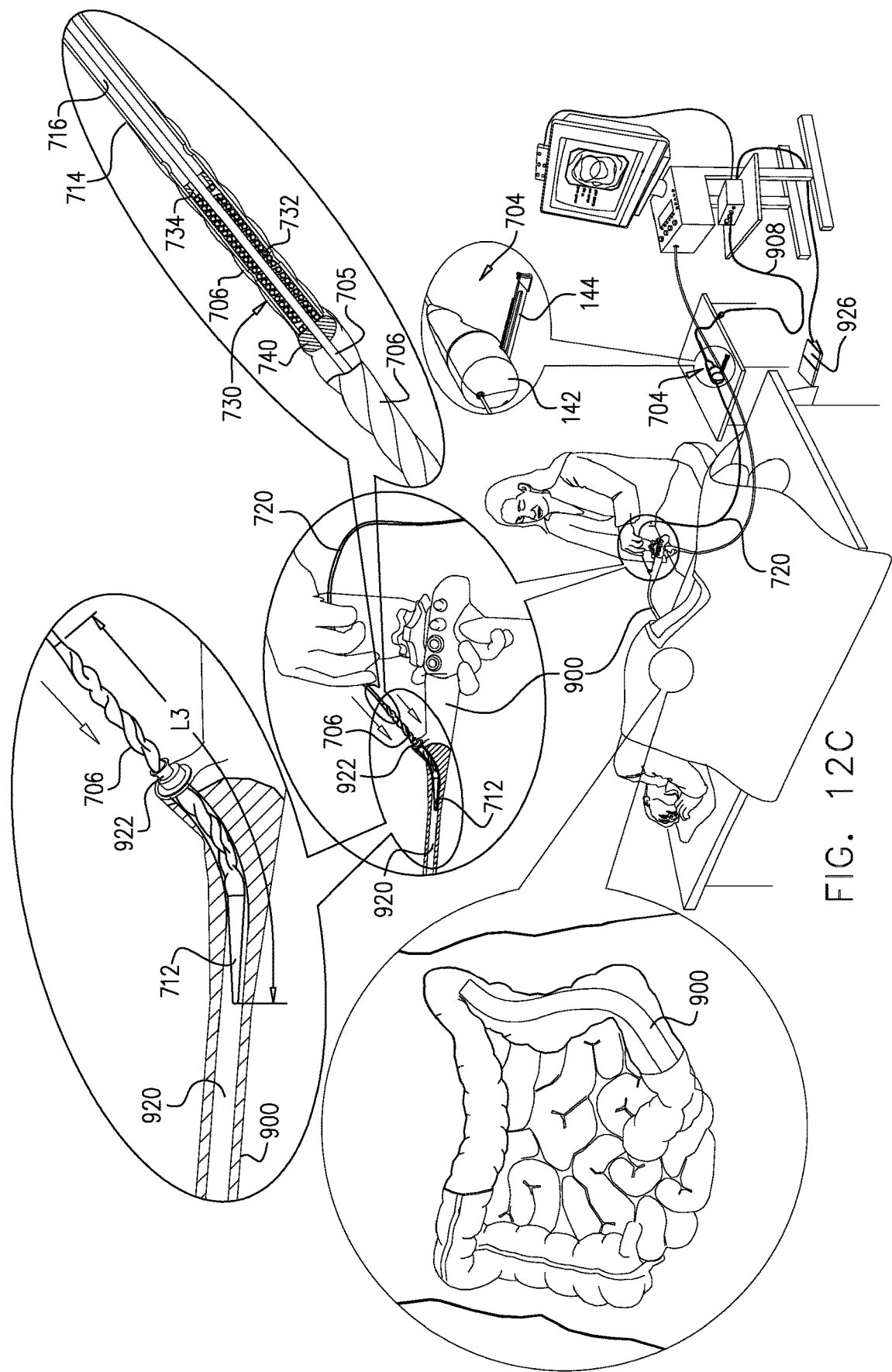

Reference is now made to FIG. 12C, which illustrates insertion of the fully-furled balloon sheath 706 into an instrument channel 920 of endoscope 900 via an instrument channel port 922. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Figure 12D:
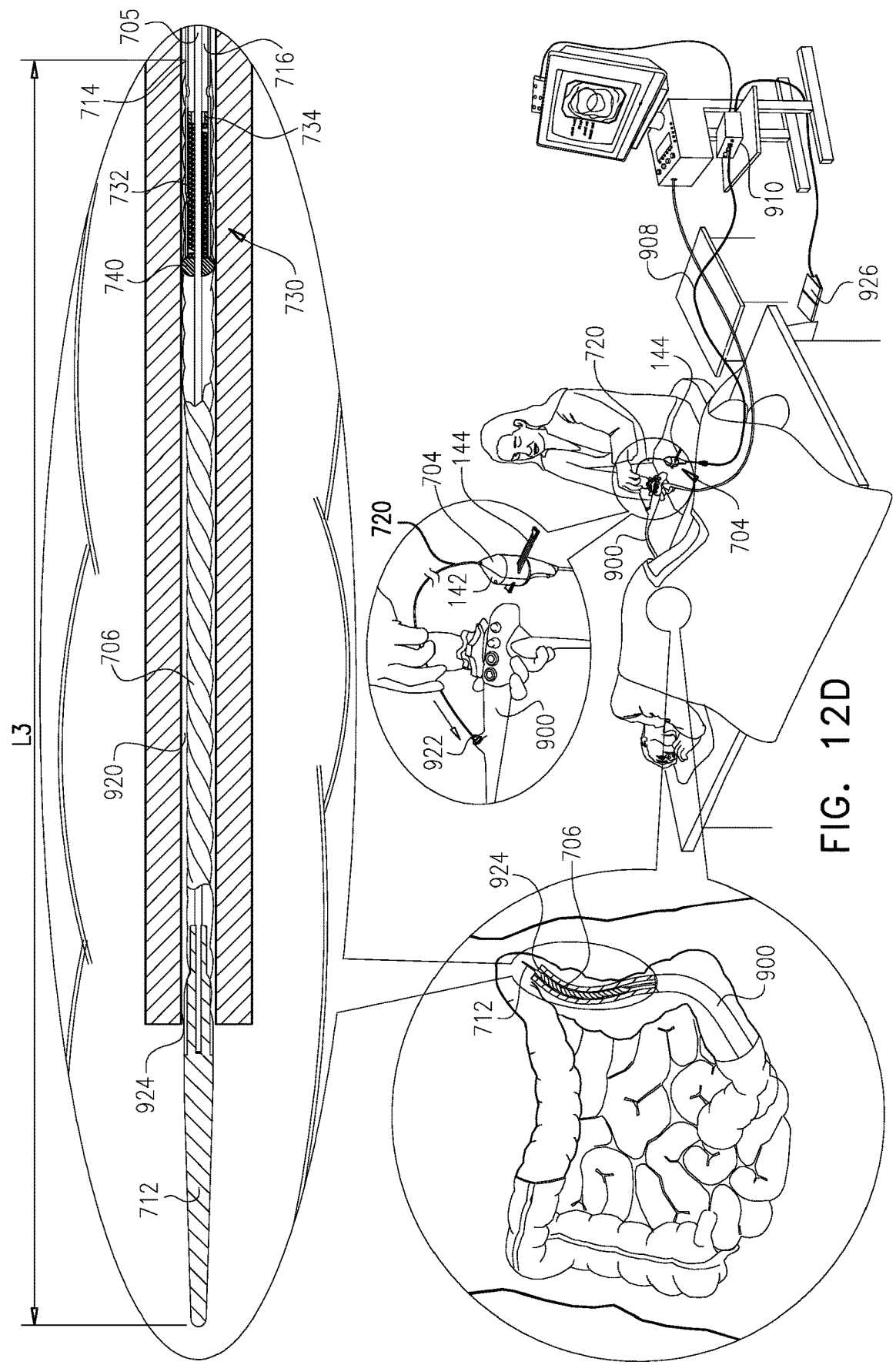

Reference is now made to FIG. 12D, which illustrates further insertion of the fully-furled balloon sheath 706 and the catheter tube 720 into instrument channel 920 of endoscope 900 via instrument channel port 922, such that the tip element 712 extends partially beyond a forward end 924 of the instrument channel 920. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Figure 12E:
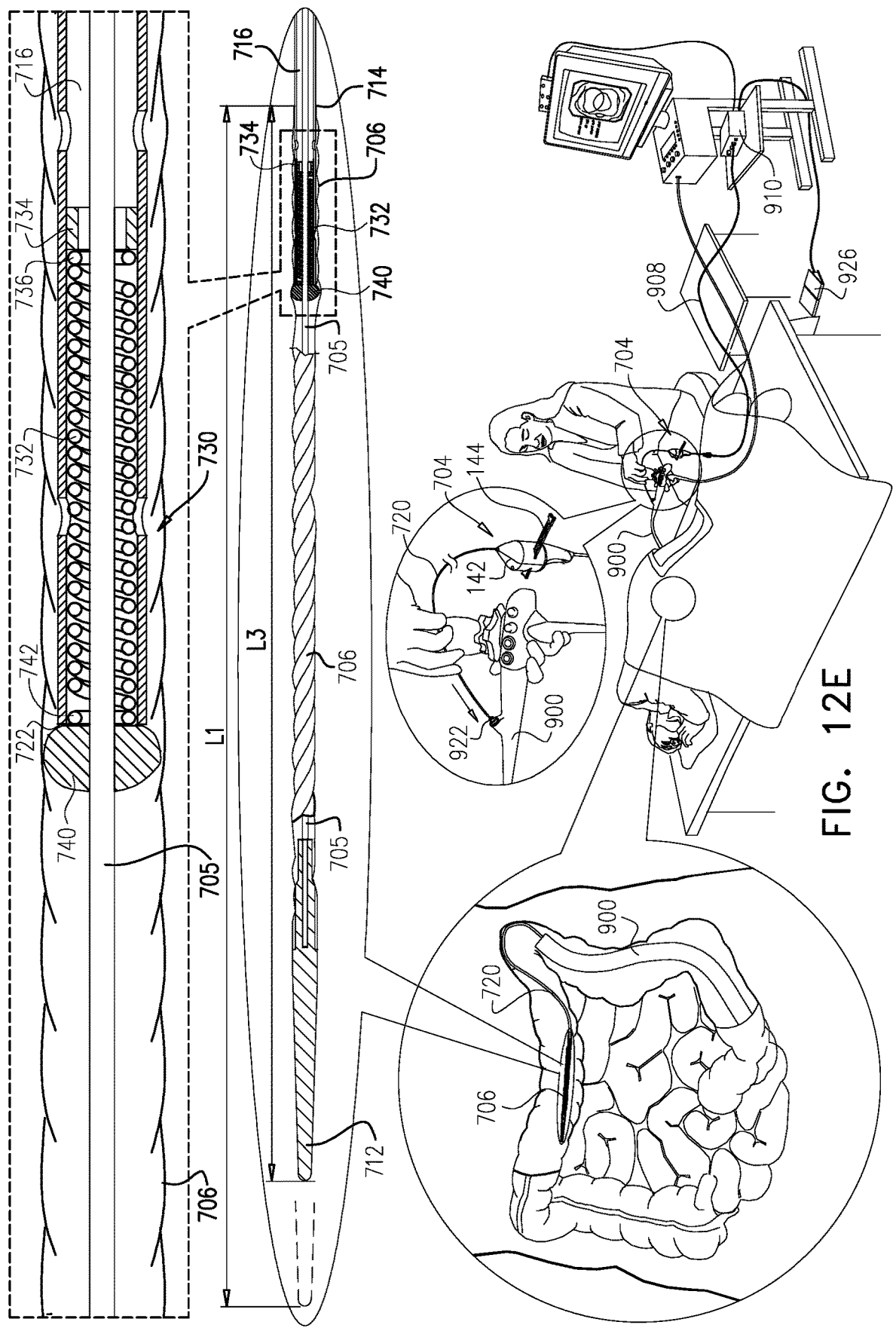

Reference is now made to FIG. 12E, which illustrates still further insertion of the fully-furled balloon sheath 706 and the catheter tube 720 into instrument channel 920 of endoscope 900 via instrument channel port 922, such that the balloon sheath 706 is located beyond a tight curve of the colon, here the splenic flexure. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Figure 12F:
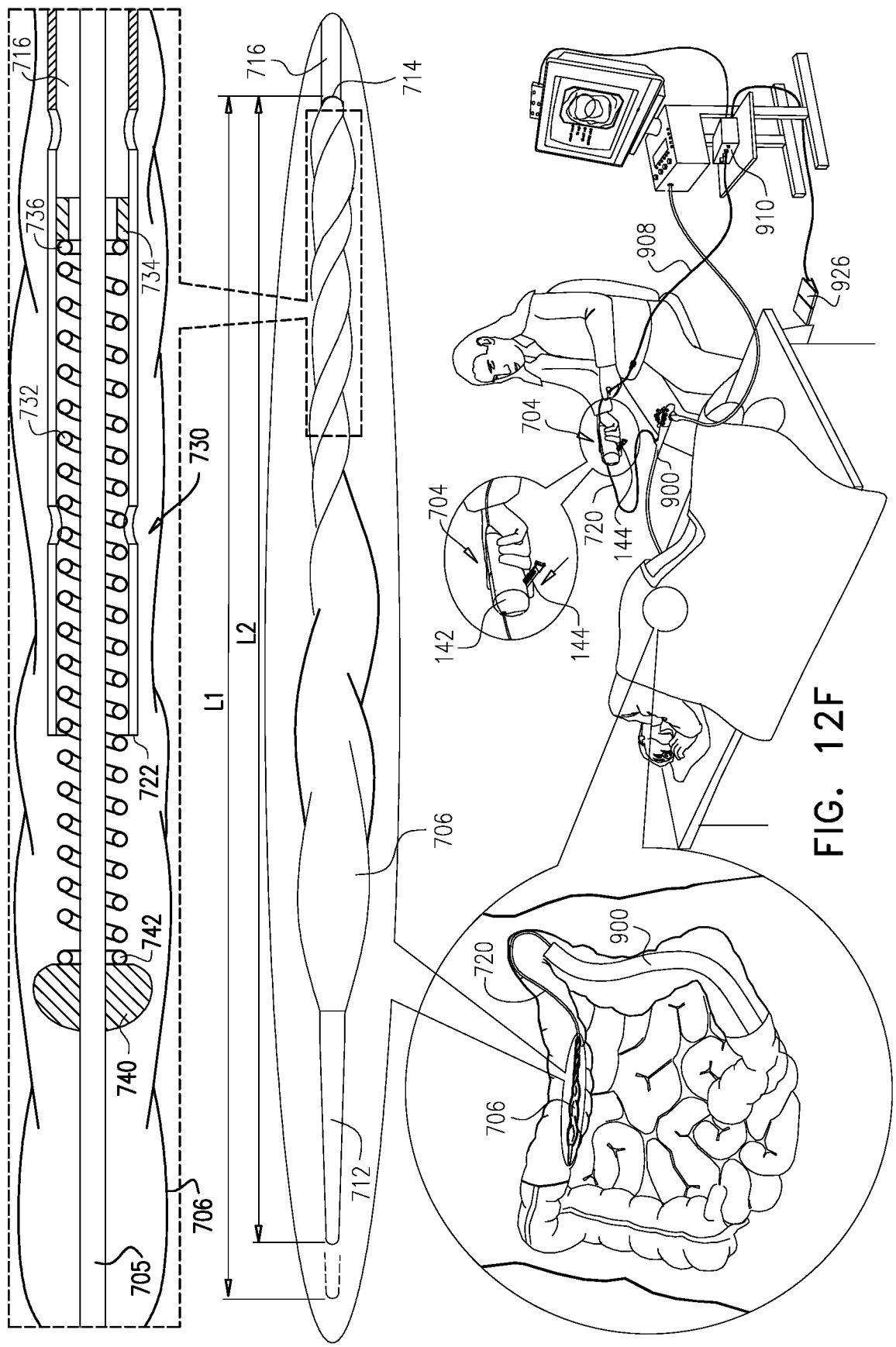

Reference is now made to FIG. 12F, which illustrates partial unfurling of the balloon sheath 706 by operation of furling control assembly 704. It is seen that the longitudinal extent along elongate furling driving element 705 from the rearward end 714 of balloon sheath 706 to the forward end of tip element 712 is L2 for this partially furled operational state, where L2 is shorter than L1 but longer than L3. It is further seen that spring engagement element 740 is at an intermediate position, spaced forwardly from forward edge 722 of catheter tube 720 but rearward of its position as seen in FIG. 12A. Spring 732 is no longer fully compressed but is more compressed than seen in FIG. 12A.

Figure 12G:
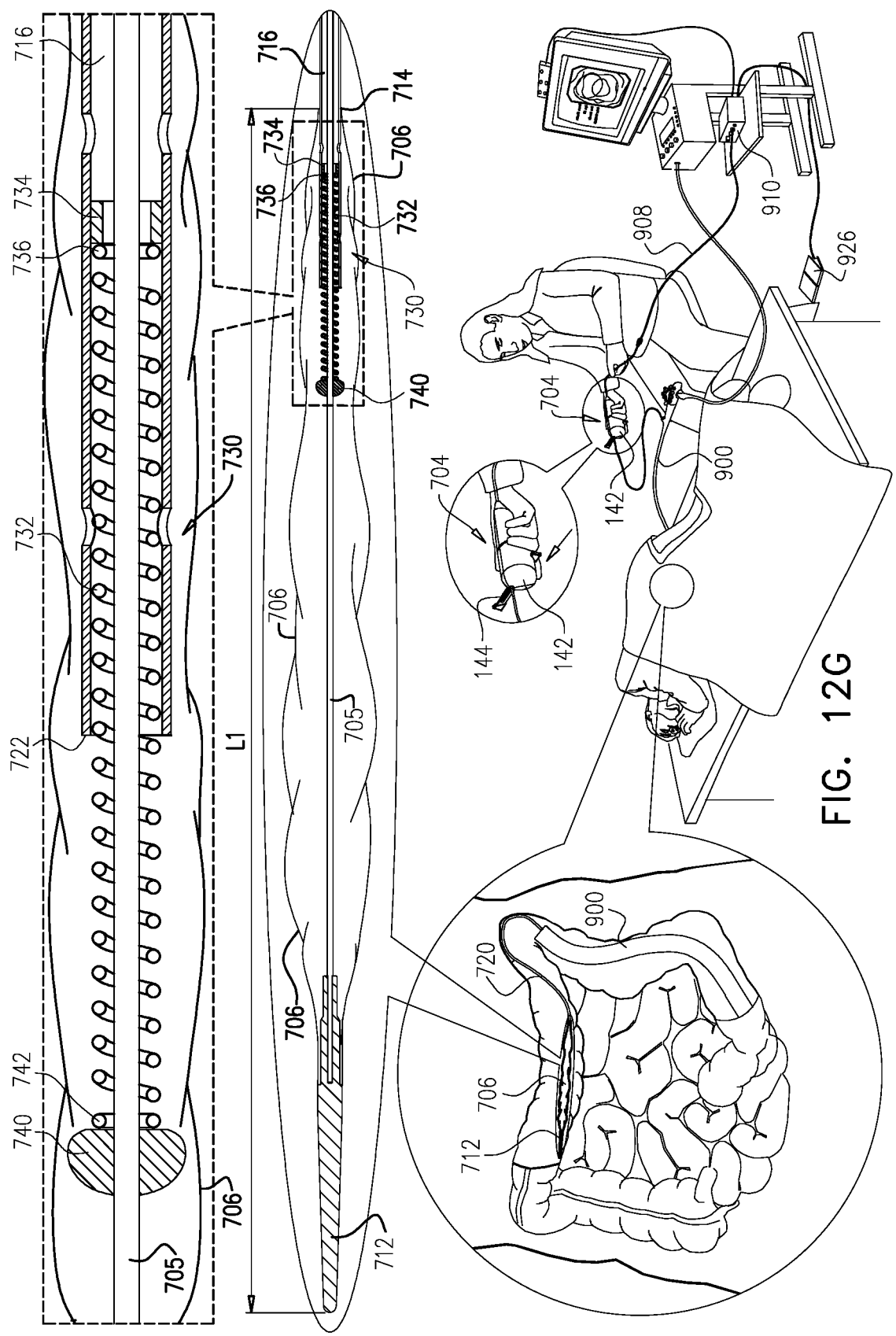

Reference is now made to FIG. 12G, which illustrates full unfurling of the balloon sheath 706 by operation of furling control assembly 704. It is seen that the longitudinal extent along elongate furling driving element 705 from the rearward end 714 of balloon sheath 706 to the forward end of tip element 712 is L1 for this fully unfurled operational state. It is further seen that spring engagement element 740 is at a forward position relative to forward end 722 of catheter tube 720, as also seen in FIGS. 12A & 12F.

Figure 12H:
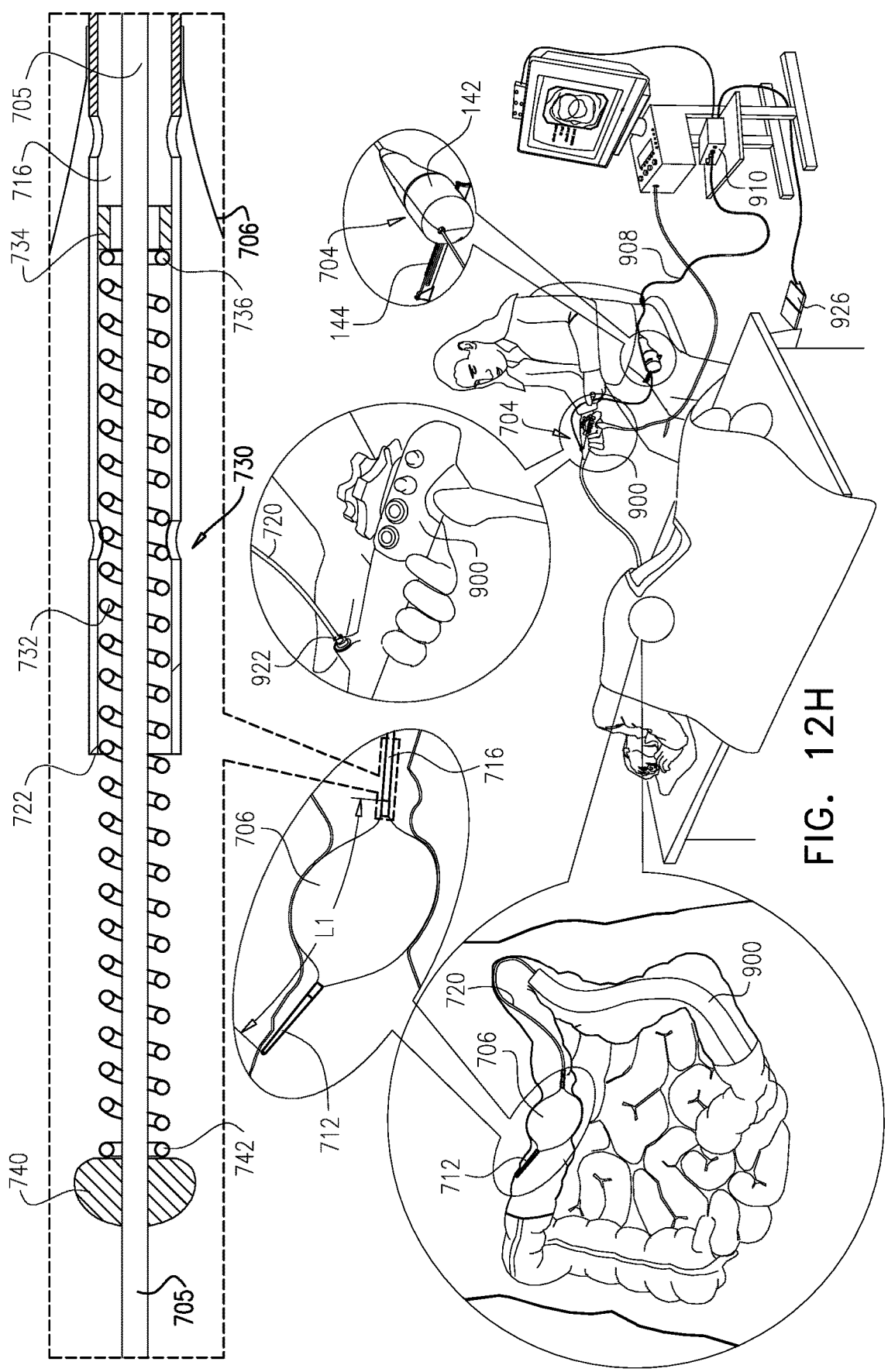

Reference is now made to FIG. 12H, which illustrates inflation of the balloon sheath 706 by operation of inflation/deflation device 910, as by the operator depressing a foot pedal 926. It is seen that the longitudinal extent along elongate furling driving element 705 from the rearward end 714 of balloon sheath 706 to the forward end of tip element 712 is L1 for this fully unfurled, inflated, operational state. It is further seen that spring engagement element 740 is at a forward position relative to forward end 722 of catheter tube 720, as also seen in FIGS. 12A, 12F & 12G.

Figure 12I:
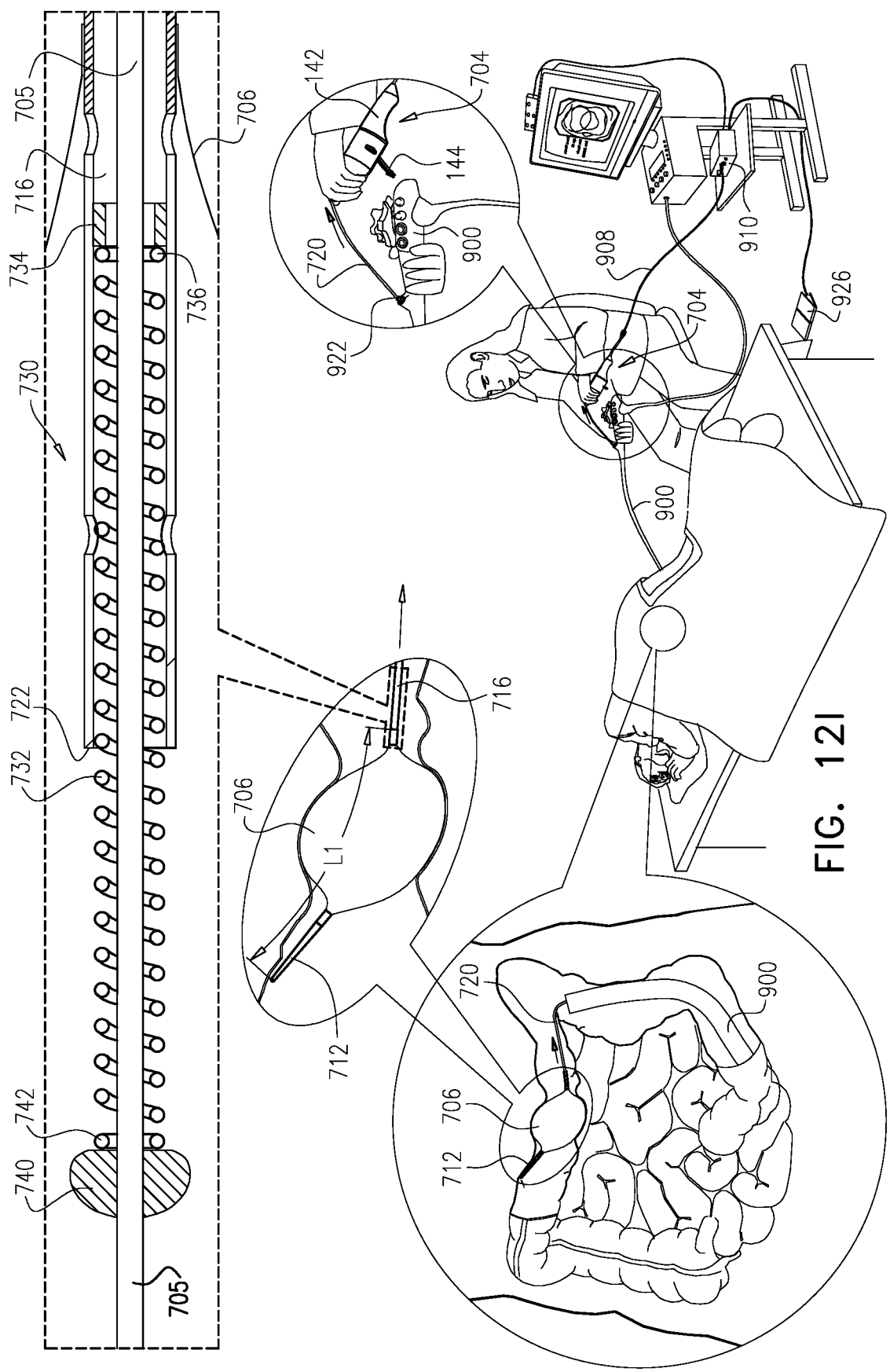

Reference is now made to FIG. 12I, which illustrates pulling back on the catheter tube 720 by the operator. It is seen that the longitudinal extent along elongate furling driving element 705 from the rearward end 714 of balloon sheath 706 to the forward end of tip element 712 is L1 for this fully unfurled, inflated, operational state. It is further seen that spring engagement element 740 is at a forward position relative to forward end 722 of catheter tube 720, as also seen in FIGS. 12A & 12F-12H.

Figure 12J:
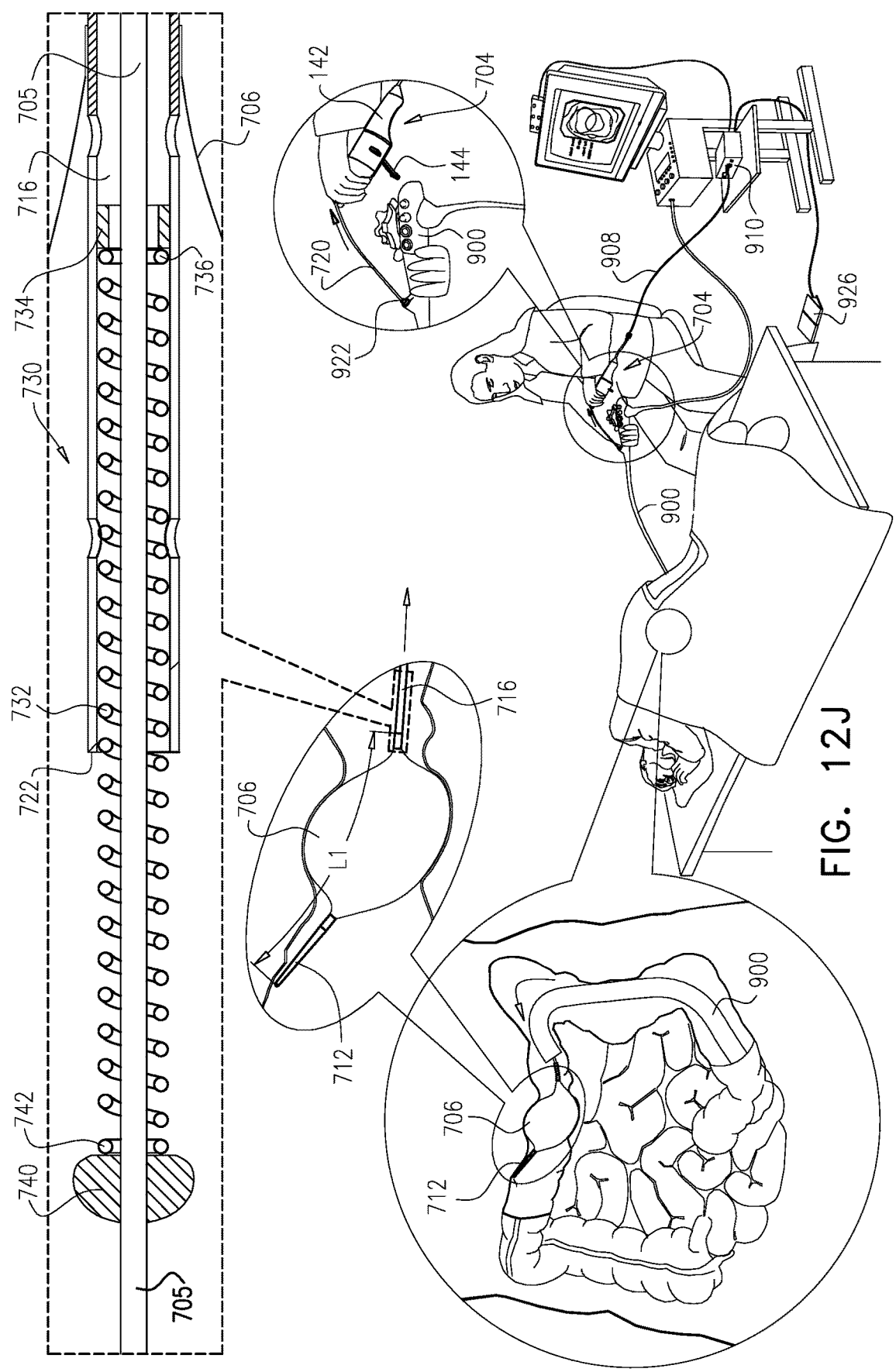

Reference is now made to FIG. 12J, which illustrates pushing the endoscope 900 forwardly using the catheter tube 720 as a guide until it reaches the rearward end 714 of balloon sheath 706. It is seen that the longitudinal extent along elongate furling driving element 705 from the rearward end 714 of balloon sheath 706 to the forward end of tip element 712 is L1 for this fully unfurled, inflated, operational state. It is further seen that spring engagement element 740 is at a forward position relative to forward end 722 of catheter tube 720, as also seen in FIGS. 12A & 12F-12I.

Figure 12K:
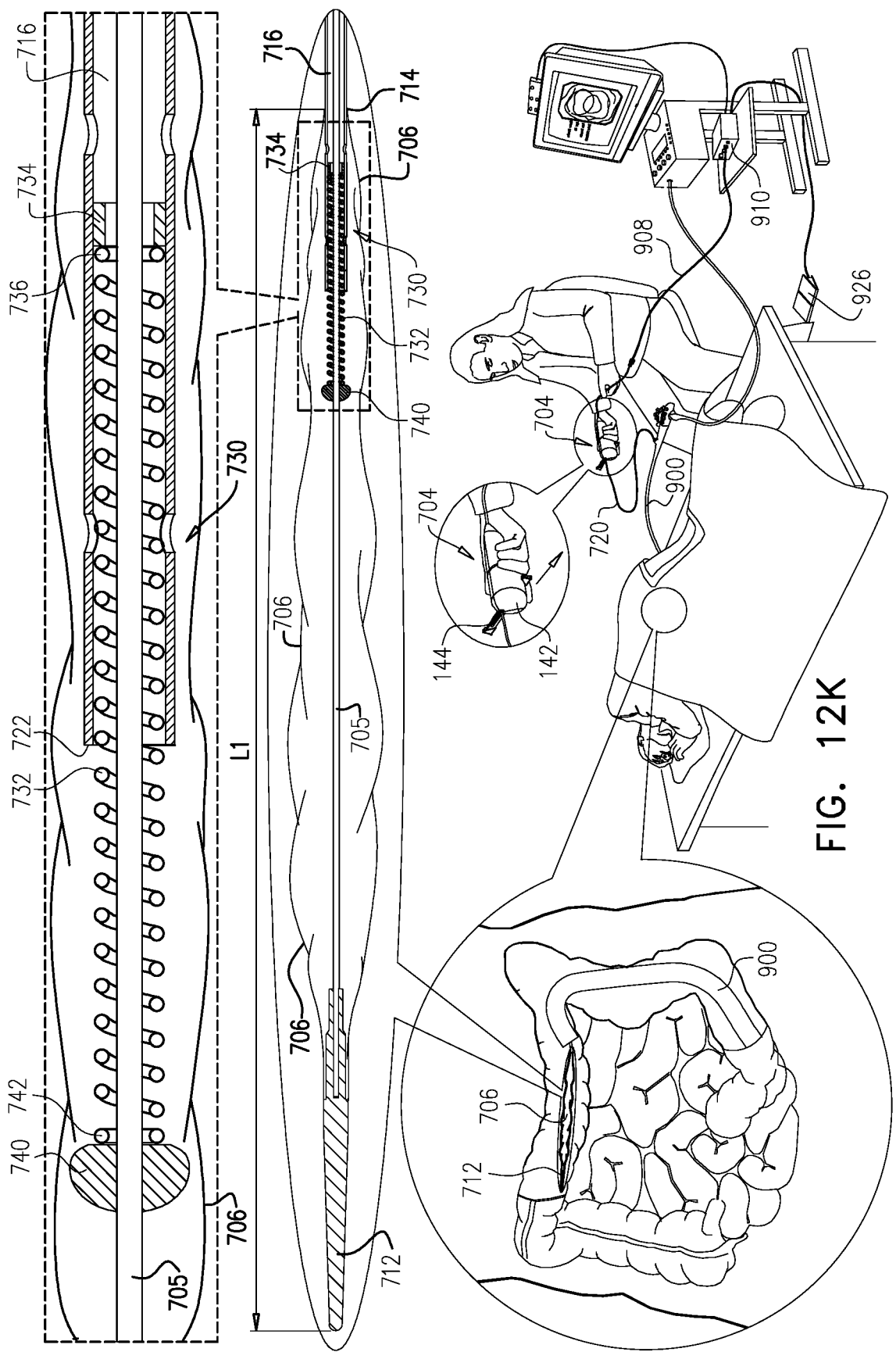

Reference is now made to FIG. 12K, which illustrates deflation of the fully unfurled balloon sheath 706. It is seen that the longitudinal extent along elongate furling driving element 705 from the rearward end 714 of balloon sheath 706 to the forward end of tip element 712 is L1 for this fully unfurled, deflated, operational state. It is further seen that spring engagement element 740 is at a forward position relative to forward end 722 of catheter tube 720, as also seen in FIGS. 12A & 12F-12J.

Figure 12L:
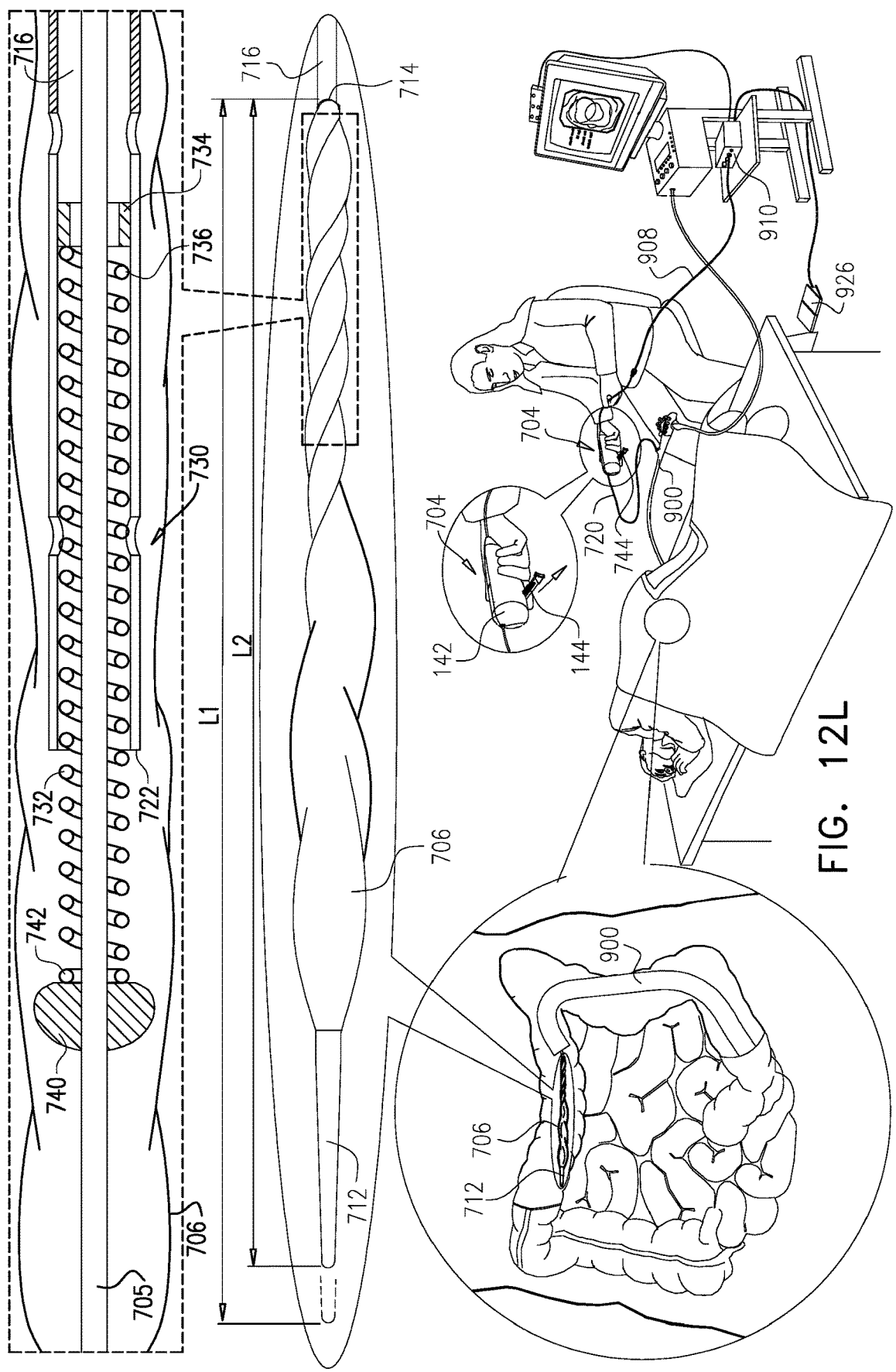

Reference is now made to FIG. 12L, which illustrates partial furling of balloon sheath 706. It is seen that the longitudinal extent along elongate furling driving element 705 from the rearward end 714 of balloon sheath 706 to the forward end of tip element 712 is L2 for this partially furled operational state, where L2 is shorter than L1 but longer than L3. It is further seen that spring engagement element 740 is at an intermediate position, similar to that shown in FIG. 12F, spaced forwardly from forward edge 722 of catheter tube 720 but rearward of its position as seen in FIG. 12A. Spring 732 is no longer fully compressed but is more compressed than seen in FIG. 12A.

Figure 12M:
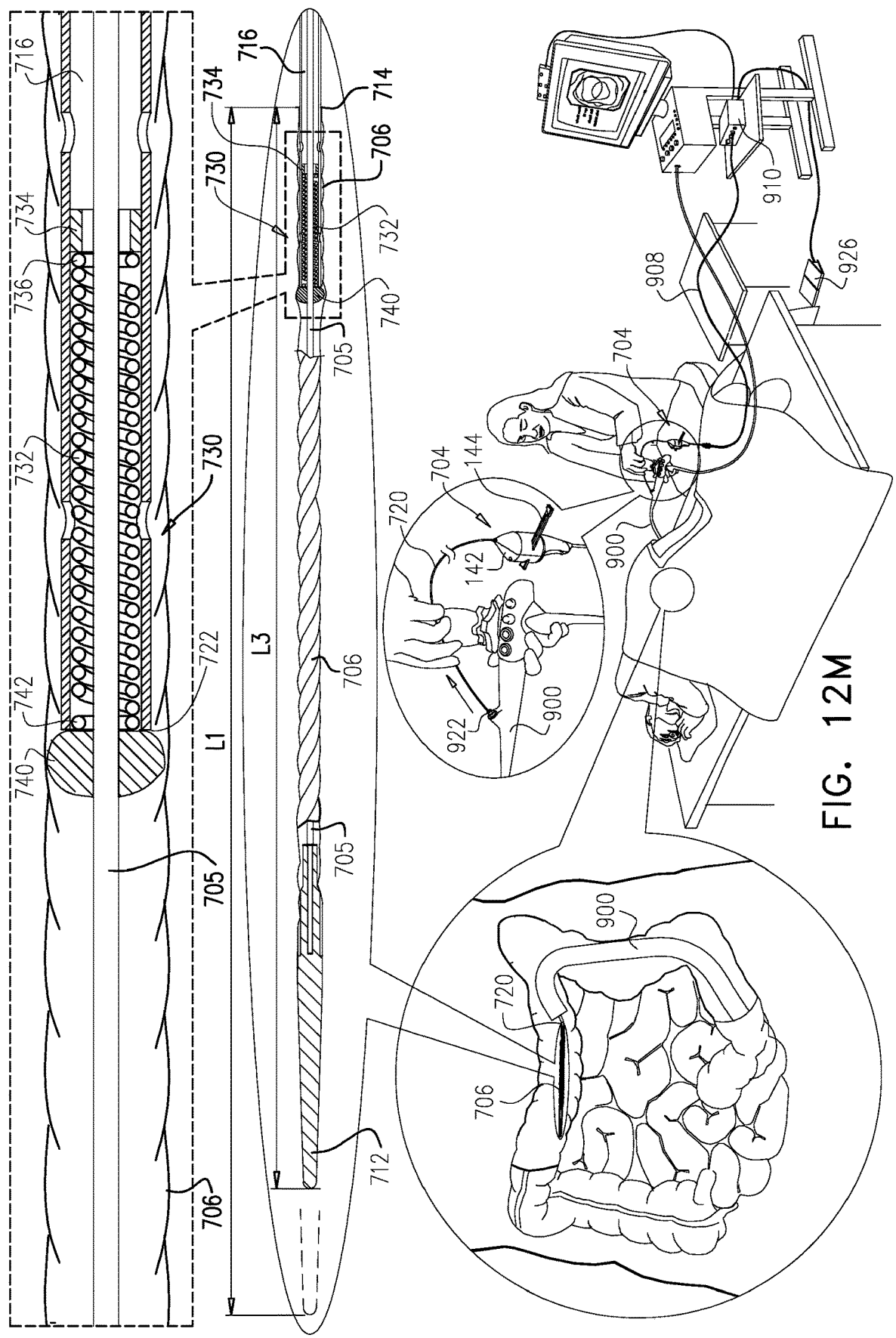

Reference is now made to FIG. 12M, which illustrates retraction and reinsertion of the fully furled balloon sheath 706 into instrument channel 920 via end 924. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed. It is a particular feature of an embodiment of the present invention that bunching of the balloon sheath 706 and consequent difficulty of retraction of the balloon sheath 706 into the instrument channel is obviated.

Figure 12N:
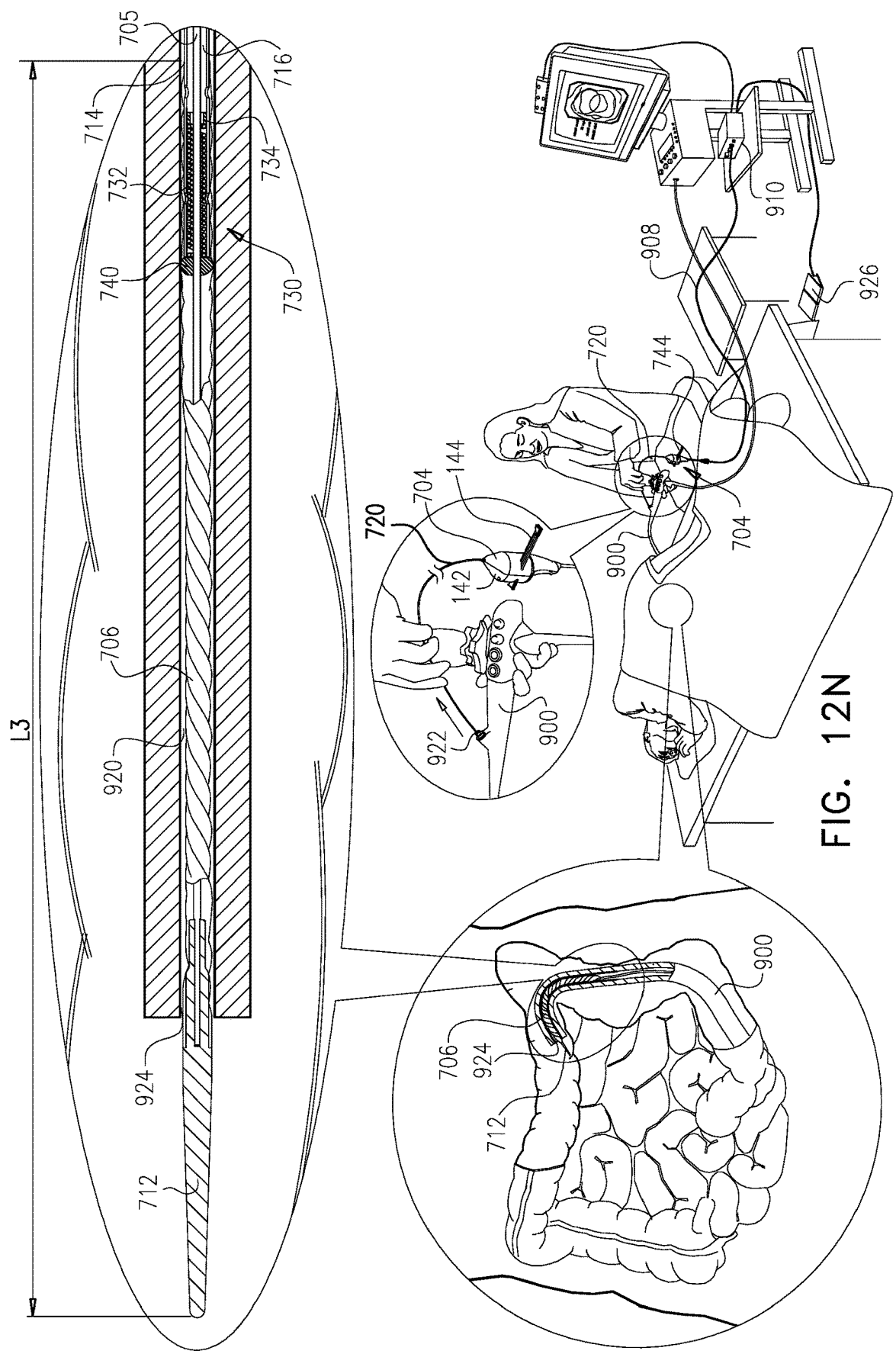

Reference is now made to FIG. 12N, which illustrates further retraction of the fully furled balloon sheath 706 into instrument channel 920. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Figure 12O:
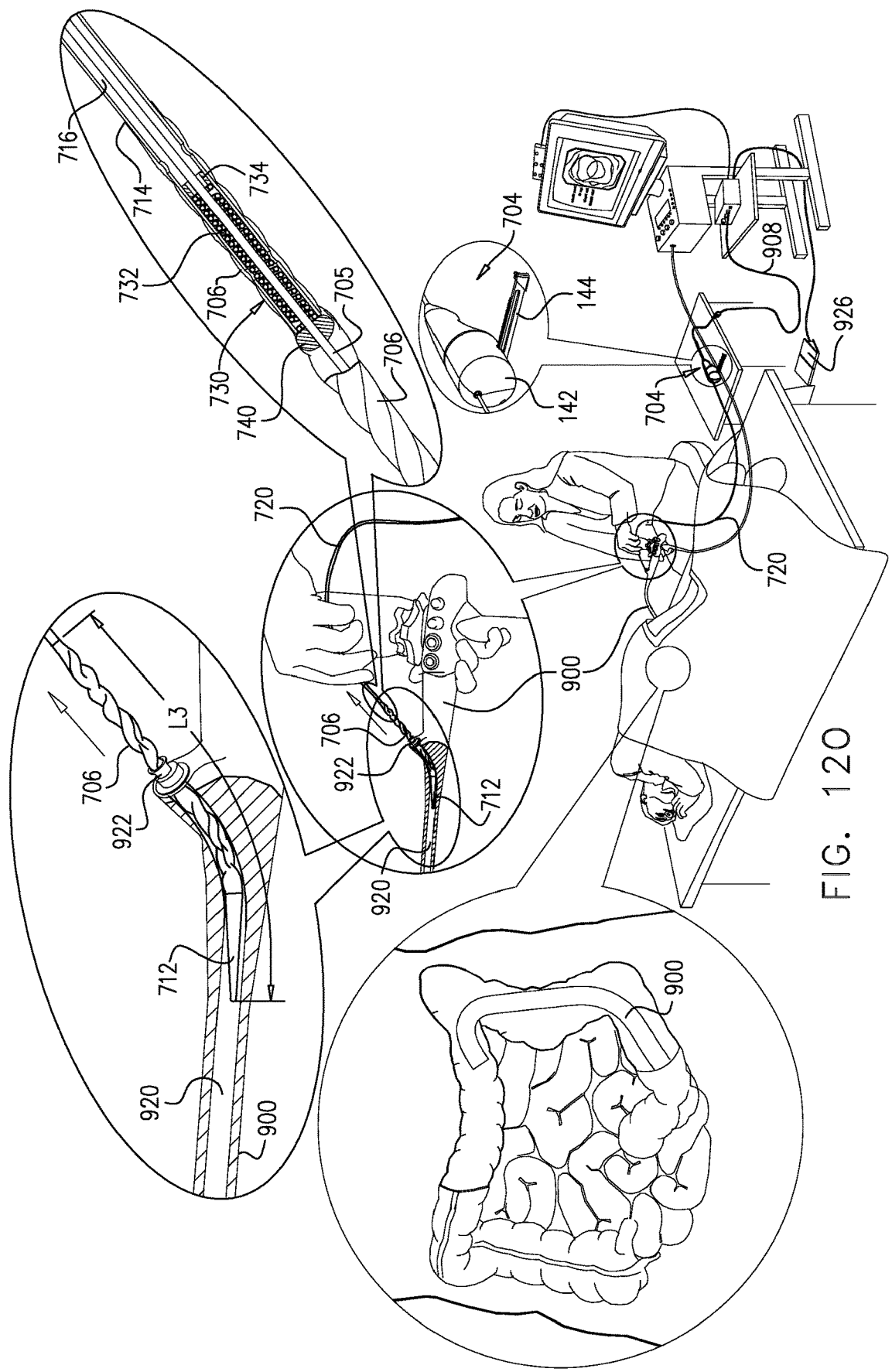

Reference is now made to FIG. 12O, which illustrates removal of the fully furled balloon sheath 706 from instrument channel 920 via port 922. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Figure 12P:
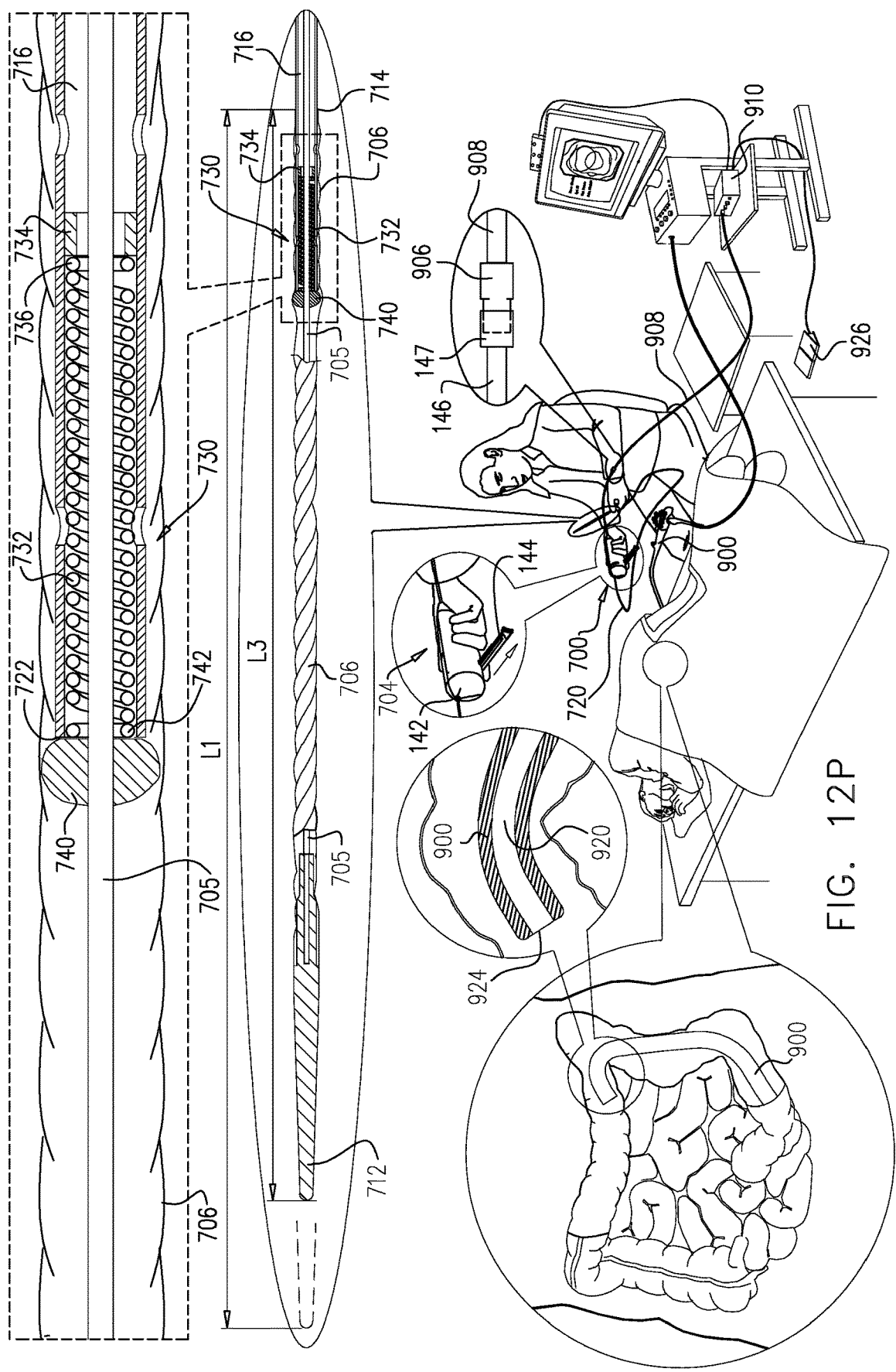

Reference is now made to FIG. 12P, which illustrates the endoscope system including the user-operable controlled furling balloon assembly 700 following removal of the fully furled balloon sheath 706 from instrument channel 920 via port 922. It is seen that the longitudinal extent along elongate furling driving element 705 from the rearward end 714 of balloon sheath 706 to the forward end of tip element 712 is L3 for this fully furled operational state. It is further seen that spring engagement element 740 is at a rearward position, abutting forward edge 722 of catheter tube 720, and spring 732 is fully compressed.

Reference is now made to FIGS. 13A, 13B, 13C and 13D, which are simplified comparative illustrations illustrating the operation of the embodiments of FIGS. 1-6P and 7-12P as compared with the prior art.

Figure 13A:
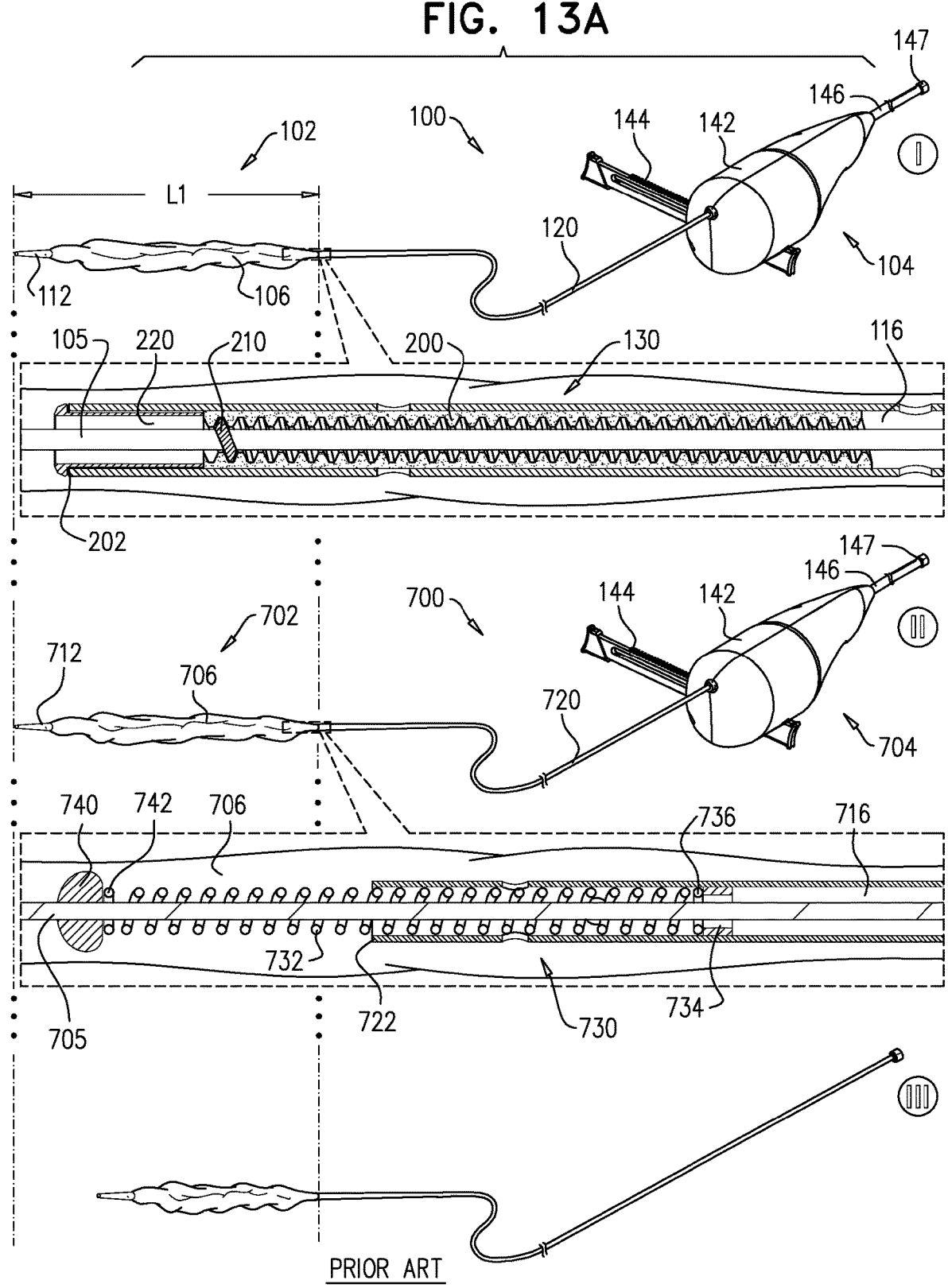
FIGS. 13A, 13B, 13C and 13D are simplified comparative illustrations illustrating the operation of the embodiments of FIGS. 1-6P and 7-12P as compared with the prior art.

Reference is initially made to FIG. 13A, which illustrates the operative orientation shown in FIGS. 6K and 12K of the embodiments of FIGS. 1-6P and 7-12P as compared with the prior art.

It is seen that in the embodiment of FIGS. 1-6P, denoted by I in FIG. 13A, the balloon sheath 106 in this operative state is seen to be fully unfurled. The longitudinal extent along elongate furling driving element 105 from the rearward end 114 of balloon sheath 106 to the forward end of tip element 112 is indicated to be L1 for this fully unfurled operational state. It is further seen that elongate furling driving element 105 is fully extended by virtue of cam element 210, fixed thereto, being at a forward position relative to cam path defining element 200.

It is seen that in the embodiment of FIGS. 7-12P, denoted by II in FIG. 13A, the balloon sheath 706 in this operative state is seen to be fully unfurled. The longitudinal extent along elongate furling driving element 705 from the rearward end 714 of balloon sheath 706 to the forward end of tip element 712 is indicated to be L1 for this fully unfurled operational state. It is further seen that elongate furling driving element 705 is fully extended by virtue of spring engagement element 740 being at a forward position relative to forward end 722 of catheter tube 720 and spring 732 being in its least compressed state.

It is seen that in the prior art, denoted by III in FIG. 13A, the balloon sheath is seen to be fully unfurled.

Figure 13B:
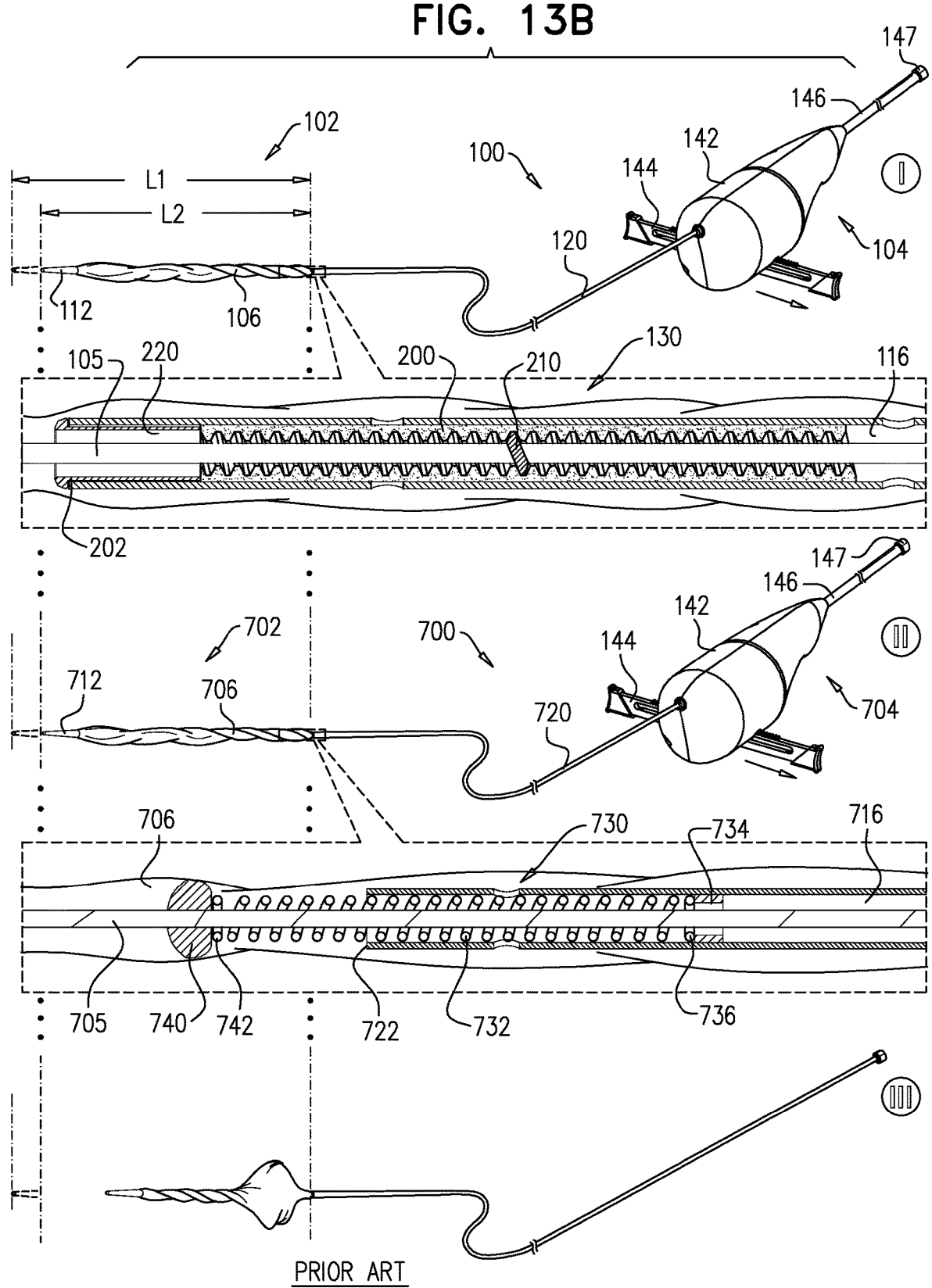

Reference is now made to FIG. 13B, which illustrates the operative orientation shown in FIGS. 6L and 12L of the embodiments of FIGS. 1-6P and 7-12P as compared with the prior art.

It is seen that in the embodiment of FIGS. 1-6P, denoted by I in FIG. 13B, the balloon sheath 106 is partially furled by operation of furling control assembly 104. It is additionally seen that the longitudinal extent along elongate furling driving element 105 from the rearward end 114 of balloon sheath 106 to the forward end of tip element 112 is L2 for this partially furled operational state, where L2 is shorter than L1 but longer than L3. It is further seen that elongate furling driving element 105 is partially retracted as permitted by virtue of cam element 210, fixed thereto, being an intermediate position relative to cam path defining element 200, between its forward position and its rearward position.

It is seen that in the embodiment of FIGS. 7-12P, denoted by II in FIG. 13B, balloon sheath 706 is partially furled by operation of furling control assembly 704. It is further seen that the longitudinal extent along elongate furling driving element 705 from the rearward end 714 of balloon sheath 706 to the forward end of tip element 712 is L2 for this partially furled operational state, where L2 is shorter than L1 but longer than L3. It is further seen that elongate furling driving element 705 is partially retracted as permitted by virtue of spring engagement element 740 being at an intermediate position, spaced forwardly from forward edge 722 of catheter tube 720 but rearward of its position as seen in FIG. 12A and by virtue of spring 732 being no longer fully compressed but more compressed than seen in FIG. 12A.

It is seen that in the prior art, denoted by III in FIG. 13B, part of the balloon sheath is bunched.

Figure 13C:
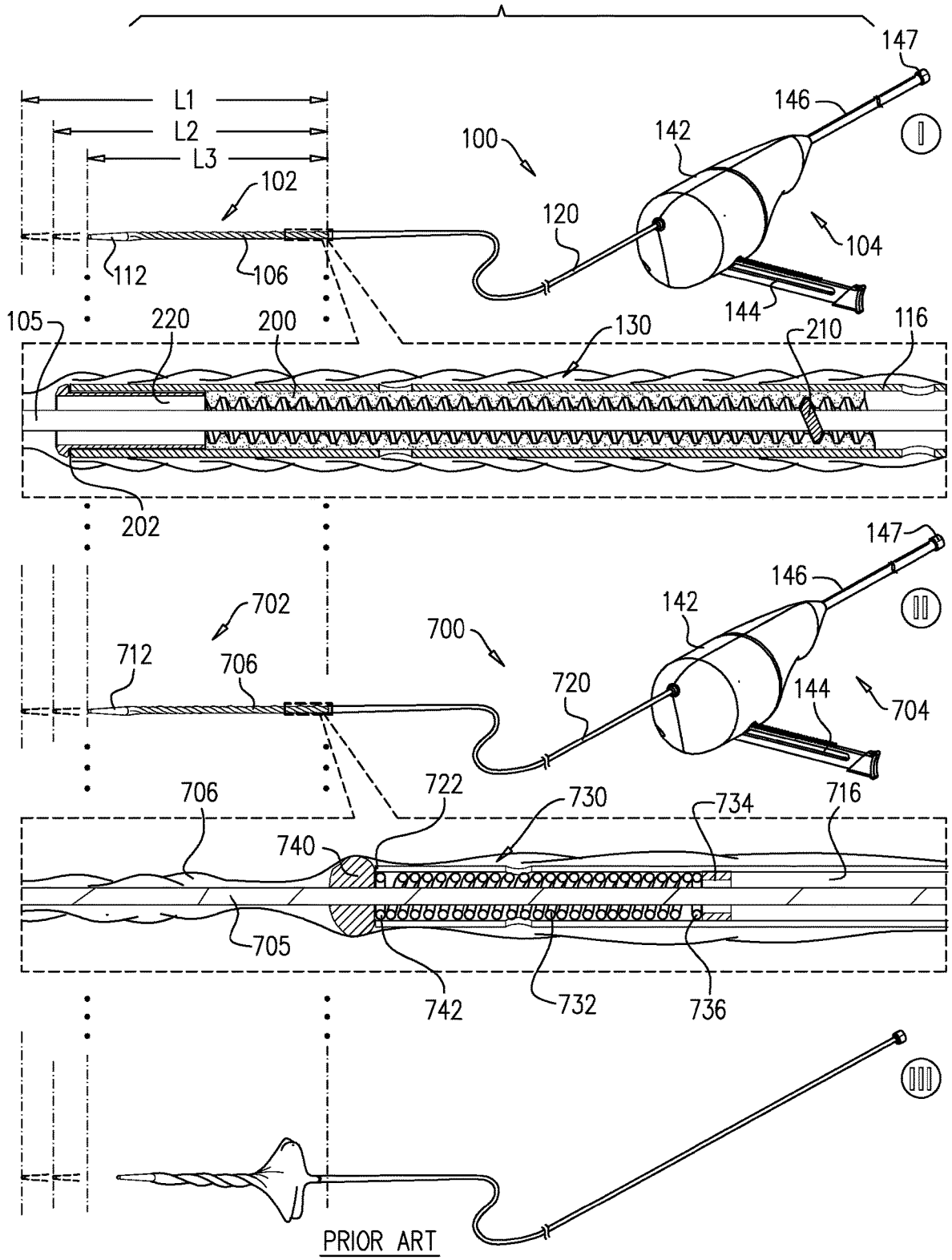

Reference is now made to FIG. 13C, which illustrates the operative orientation shown in FIGS. 6M and 12M of the embodiments of FIGS. 1-6P and 7-12P as compared with the prior art.

It is seen that in the embodiment of FIGS. 1-6P, denoted by I in FIG. 13C, the balloon sheath 106 is fully furled. It is seen that the longitudinal extent along elongate furling driving element 105 from the rearward end 114 of balloon sheath 106 to the forward end of tip element 112 is L3 for this fully furled operational state. It is further seen that elongate furling driving element 105 is fully retracted as permitted by virtue of cam element 210, fixed thereto, being at its rearward position relative to cam path defining element 200.

It is seen that in the embodiment of FIGS. 7-12P, denoted by II in FIG. 13C, balloon sheath 706 is fully furled. It is further seen that the longitudinal extent along elongate furling driving element 705 from the rearward end 714 of balloon sheath 706 to the forward end of tip element 712 is L3 for this fully furled operational state. It is further seen that elongate furling driving element 705 is fully retracted as permitted by virtue of spring engagement element 740 being at a rearward position, abutting forward edge 722 of catheter tube 720, and spring 732 being fully compressed. In the prior art, denoted by III in FIG. 13C, at least part of the balloon sheath 706 is seen to be bunched.

Figure 13D:
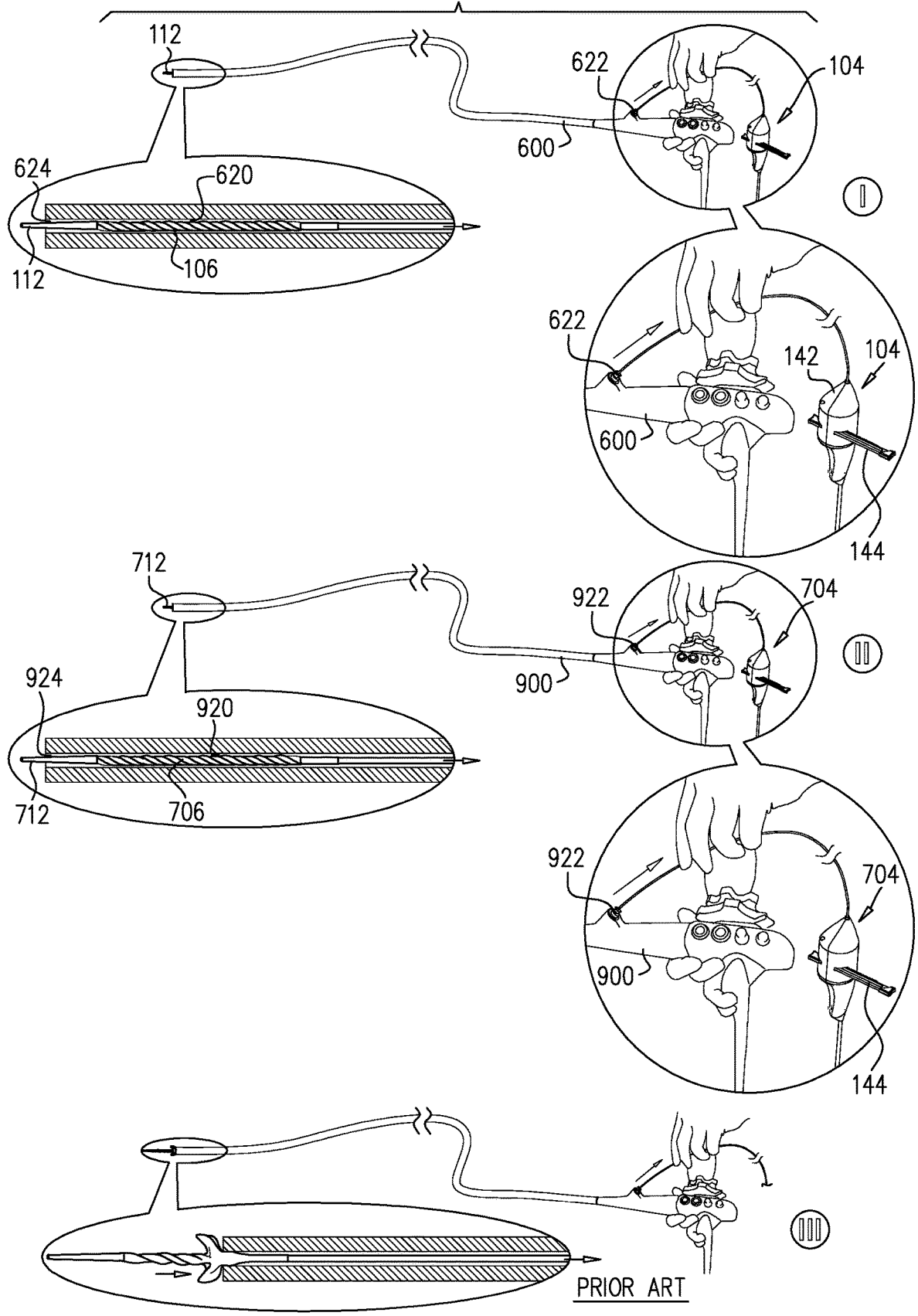

Reference is now made to FIG. 13D, which illustrates the operative orientation shown in FIGS. 6N and 12N of the embodiments of FIGS. 1-6P and 7-12P as compared with the prior art.

It is seen that in the embodiment of FIGS. 1-6P, denoted by I in FIG. 13D, the fully furled balloon sheath 106 is fully retracted into instrument channel 620. As seen in FIG. 13C, the longitudinal extent along elongate furling driving element 105 from the rearward end 114 of balloon sheath 106 to the forward end of tip element 112 is L3 for this fully furled operational state. It is further seen in FIG. 13C that cam element 210 is at its rearward position relative to cam path defining element 200.

It is seen that in the embodiment of FIGS. 7-12P, denoted by II in FIG. 13D, balloon sheath 706 is fully furled and is fully retracted into instrument channel 920. As seen in FIG. 13C, the longitudinal extent along elongate furling driving element 705 from the rearward end 714 of balloon sheath 706 to the forward end of tip element 712 is L3 for this fully furled operational state. It is further seen in FIG. 13C that spring engagement element 740 is at a rearward position, abutting forward edge 722 of catheter tube 720, and spring 732 is fully compressed.

It is additionally seen that in the prior art, denoted by III in FIG. 13D, the balloon sheath 706 cannot be retracted into the instrument channel due to bunching.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

The invention claimed is:

1. A user-operable controlled furling balloon assembly comprising:
   a furlable balloon sheath;
   an elongate furling driving element which is retractable and rotatable about an elongate axis thereof within, and relative to, a catheter tube, for furling said furlable balloon sheath about said elongate axis, said furlable balloon sheath surrounding a forward portion of said elongate furling driving element and coupled at a first end thereof to said elongate furling driving element and at a second end thereof to a forward portion of said catheter tube;
   a furling/retraction controlling assembly directly coupled to said elongate furling driving element and to said forward portion of said catheter tube and comprising a cam element fixed to said elongate furling driving element and engaging a spiral cam path defining element attached to said forward portion of said catheter tube, said cam element being led by said spiral cam path defining element to rotate and retract relative to said forward portion of said catheter tube upon rotation of said elongate furling driving element and furling of said furlable balloon sheath, thereby limiting an extent of retraction of said elongate furling driving element to be a function of an extent of furling of said balloon sheath, thereby limiting a maximum outer diameter of said balloon sheath when furled;
   a furling control assembly, directly coupled to said elongate furling driving element and to said catheter tube at rearward portions thereof, and operable to rotate said elongate furling driving element relative to said catheter tube; and
   a tip element coupling said balloon sheath to said elongate furling driving element and wherein a longitudinal extent along said elongate furling driving element from a rearward end of said balloon sheath to a forward end of said tip element is a first length when said balloon sheath is unfurled, a second length, less than said first length, when said balloon sheath is partially furled and a third length, less than said first length and less than said second length, when said balloon sheath is fully furled.

2. A user-operable controlled furling balloon assembly according to claim 1 and wherein said furling control assembly comprises:
   a housing; and
   a manually-manipulatable linear driving element, manually linearly positionable relative to said housing for controlling the extent of furling of said furlable balloon sheath.

3. A user-operable controlled furling balloon assembly according to claim 2
   and wherein:
   linear displacement of said manually-manipulatable linear driving element in a first linear direction provides furling of said furlable balloon sheath; and linear displacement of said manually-manipulatable linear driving element in a second linear direction, opposite said first linear direction, provides unfurling of said furlable balloon sheath.

* * * * *